United States Patent [19]
Sun

[11] Patent Number: 6,002,251
[45] Date of Patent: Dec. 14, 1999

[54] ELECTROMAGNETIC-FIELD-FOCUSING REMOTE-FIELD EDDY-CURRENT PROBE SYSTEM AND METHOD FOR INSPECTING ANOMALIES IN CONDUCTING PLATES

[76] Inventor: Yu-shi Sun, 1209 Northwestern Ave., Ames, Iowa 50010

[21] Appl. No.: 08/647,310

[22] Filed: May 9, 1996

Related U.S. Application Data

[60] Provisional application No. 60/008,679, Dec. 15, 1995.

[51] Int. Cl.⁶ .................................................. G01N 27/82
[52] U.S. Cl. ..................... 324/240; 324/235; 324/232; 324/233; 324/262
[58] Field of Search ..................................... 324/240, 239, 324/229, 228, 232, 236, 237, 238, 242, 243, 217, 235, 262, 233; 174/35 R, 35 CE

[56] References Cited

U.S. PATENT DOCUMENTS

| | | |
|---|---|---|
| 2,573,799 | 11/1951 | MacClean . |
| 4,797,614 | 1/1989 | Nelson ..................................... 324/236 |
| 5,264,733 | 11/1993 | Tigges ..................................... 324/236 |
| 5,648,721 | 7/1997 | Wincheski et al. ..................... 324/209 |

FOREIGN PATENT DOCUMENTS

| | | | |
|---|---|---|---|
| 1208291 | 7/1986 | Canada ........................... G01N 27/90 |
| 24232 | 7/1990 | China . | |

OTHER PUBLICATIONS

Y.S. Sun, et al., "Progress in Developing RFEC Probe for Tank Bottom Inspection", presented on ASNT's 1996 Spring Conference ASNT, Norfolk, VA, Mar. 19–21, 1996.

Y. S. Sun, et al., "Inspection of Metallic Plates Using A Novel Remote Field Eddy Current NDT Probe", Review of Progress in QNDE, vol. 15A, 1996, pp. 1137–1144.

Y. S. Sun, et al., "Efforts Towards Gaining a Better Understanding of The Remote Field Eddy Current Phenomenon and Expanding its Applications", IEEE Transaction on Magnetics, vol. 32, 1996, pp. 1589–1592.

Y. Sun, S. Udpa, W. Lord and D. Cooley, "A Remote Field Eddy Current NDT Probe for the Inspection of Metallic Plates", *Topical Conference Paper Summaries Book—ASNT's International Chemical and Petroleum Industry Inspection Technology (ICPIIT) IV Topical Conference*, 1995 and Materials Evaluation, vol. 54/No. 4, Apr. 1996(Appendix–09).

Y. S. Sun, et al., "Motion Induced Remote Field Eddy Current Effect in a Magnetostatic Non–destructive Testing Tool", IEEE Transaction on Magnetics, vol. 30, pp. 3304–3307, Sep. 1994.

(List continued on next page.)

*Primary Examiner*—Jay Patidar
*Attorney, Agent, or Firm*—Schwegman, Lundberg, Woessner & Kluth, P.A.

[57] ABSTRACT

An electromagnetic-field-focusing remote-field eddy-current probe for inspecting anomalies in a conducting plate. The probe is designed to have the electromagnetic energy released from an excitation coil penetrate through the plate twice, so that the signals received by one or more receiver units (pickup coils, magneto-resistors or SQUIDs) have passed twice through the plate wall; from one side of the plate at the excitation coil to the other side, then back to the original side at the receiver units. The probe detects flaws, with good and substantially equal sensitivity, irrespective of their depth in the plate. It can detect, from one side of a plate, flaws located on the other side of the plate, which is useful for inspecting the bottom plate of a huge tank which is sitting on the ground. The thickness of inspected plates can go up to one inch for aluminum plates and to ⅜" for ferromagnetic plates. The probe generates a periodic magnetic field. The excitation coil and an auxiliary device direct the electromagnetic field into the plate being inspected. In one embodiment, the auxiliary device is a coil driven by a signal having a phase and amplitude relationship to the excitation coil's signal. The excitation and the receiver units are covered by one or more shields made of highly conducting materials, or of highly conducting materials laminated with alternating layers of ferromagnetic materials.

55 Claims, 55 Drawing Sheets

OTHER PUBLICATIONS

Y. S. Sun, et., "Finite Element Modeling and Physics of Remote Field Eddy Current Responses for Axially Aligned Cracks", IEEE Transaction on Magnetics, vol. 28, pp. 1941–1947, Jul. 1992.

Y. S. Sun, et., "Improvement in Remote–Field Eddy Current Probe Structure", Materials Evaluation, vol. 50, pp. 600–604, May, 1992. (Appendix –12).

M. Chen, Y. Sun, et al., "Pulsed RFEC Response", IEEE Transaction on Magnetics, vol. 28, No. 2, pp. 1430–1433, Mar. 1992.

Y. S. Sun, at al., "Computer Animated Presentation Visualizing The Phenomena in Remote Field Eddy Current Nondestructive Test Technique", *Electromagnetic Forces and Applications*, edited by J. Tani and T. Takagi, pp. 203–206, *Elsevier Science Publishers*, 1992.

Y. S. Sun, at al., "Crack Modeling Problem in Eddy Current Nondestructive Testing", Electromagnetic Phenomena and Computation Techniques, edited by M. Enokizono and J. P. Nowaski, pp. 173–182, *Elsevier*.

M. J. Chen and Y. S. Sun, "A Finite Element Prediction of Possible Application of Pulse Excitation in Remote Field Eddy Current Nondestructive Inspection Devices", International Journal of Applied Electromagnetics in Materials, vol. 2, pp. 217–220, 1991.

Y. Sun, at al., "3–D Finite Element Modeling of the Remote Field Eddy current Effect", Review of Progress in QNDE, vol. 9A, pp. 319–326, 1990.

H. Y. Lin and Y. S. Sun, Application of "Zoom–In" Technique in 3D Remote Field Eddy.

Y. –S. Sun, "Finite Element Study of Diffusion Energy Flow in Low–Frequency Eddy Current Fields", Materials Evaluation, vol. 47, pp. 87–92, 1989.

W. Lord, Y. S. Sun, S. U. Udpa, "Physics of Remote Field Eddy Current Effect", Review of Progress in Quantitative Nondestructive Evaluation, vol. 7A, pp. 165–172, 1988.

W. Lord, Y. Sun, S. Udpa, "A Finite Element Study of the Remote Field Eddy Current Phenomenon", IEEE Transaction on Magnetics, vol. 24, pp. 435–438, Jan. 1988.

T.R. Schmidt, "The Remote Field Eddy Current Technique", *Materials Evaluation*, vol. 42, pp. 225–230, Feb. 1984.

D.A. Atherton, et al., "Finite–Element Calculation for Shields in Remote–Field Eddy Current Tools", *Materials Evaluation*, vol. 47, pp. 1084–1088, Sep. 1989.

E. von Rosen and David Atherton, "Effect of Shielding and Exciter Coil Tilt on the Remote–Field Effect", *Materials Evaluation*, vol. 51, pp. 66–71, Jan. 1993.

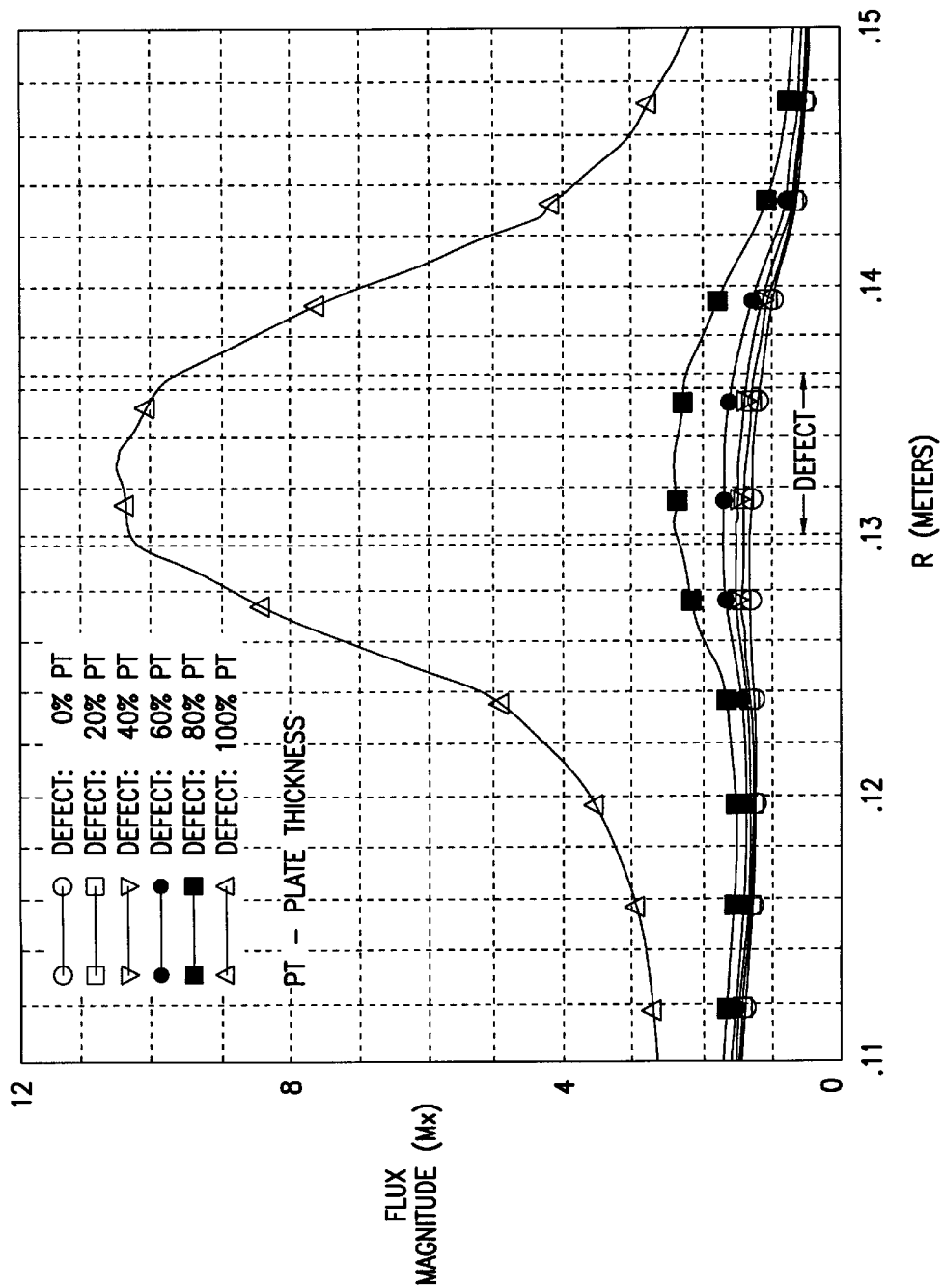

ELECTROMAGNETIC-FIELD-FOCUSING REMOTE-FIELD EDDY-CURRENT PROBE SYSTEM AND METHOD FOR INSPECTING ANOMALIES IN CONDUCTING PLATES

This application claims benefit of U.S. Provisional Application No. 60/008,679 filed Dec. 15, 1995.

TECHNICAL FIELD OF THE INVENTION

The present invention pertains generally to non-destructive testing and more particularly to a remote-field eddy-current probe and methods for using same for non-destructive testing of metallic plates.

BACKGROUND OF THE INVENTION

The need and demand for inspection of metallic plates in an aging infrastructure has been increasing within the last decade due to an increase in both public awareness and concern for the environment. The non-destructive evaluation ("NDE") techniques currently in use do not meet all the requirements for such inspections. Recent market research indicates that there is a call for better inspection techniques. The technique and apparatus described herein provide for improved inspections of flat-shaped conducting structures.

Inspection of Above-Ground Storage Tanks ("ASTs") is one exemplary use for the present invention. Newspaper headlines have reported about AST failures and leakage plumes from some older structures. ASTs have the possible hazard of (and have actually caused) contaminating underground water supplies or generating run-off contamination into streams and rivers used as water supplies. The brittle fracture of a large AST near Pittsburgh, Pa., in January 1988, serves as a prime example of such catastrophes. About one million gallons (see Moore, Patrick O., "Report on Oil Spill Affirms Importance of Material Identification NDT", *Materials Evaluation*, Vol. 46, August 1988, P. 1128.) of petroleum products were discharged into the Monongahela River. A 1993 report from Environmental Defense Fund (see EDF Report, "Last But Not Least: Leaking Aboveground Storage Tank Threats, Costs, and Answers", Environment Defense Fund, Washington, D.C., Mar. 16, 1993.) indicated that a bulk fuel tank farm in spark, Nev., had 4–40 millon gallons of petroleum plumes and that there had been petroleum releases estimated to be from 80–252 millon gallons from a single California refinery.

There are approximately 300,000 (see EDF Report, "Last But Not Least: Leaking Aboveground Storage Tank Threats, Costs, and Answer", Environment defense Fund, Washington, D.C., Mar. 16. 1993.) to 1.2 millon (see Cater, Will, "Keynote and Overview of API653 Conference Proceedings", at API653 Conference, Jun. 10–11, 1993, sponsored by CEEM Information Services, Fairfax, Va.) tanks within the United States. This also includes tanks in chemical and other industries. Seventy percent of these tanks are twenty or more years old. Assuming each tank is inspected only once every twenty years, there is a need for inspecting 15,000–60,000 tanks per year in United States alone!

There are three NDE techniques that are popular and used for tank inspections:

(1) Acoatstic Emission ("AE").

AE work well for leak detection, but does anaiot tell the tank wall thickness, which is important for advanced awareness of possible impending leaks and for the prevention of any such leaks before they occur.

(2) Ultrasonic Technique ("UT").

UT measures wall thickness accurately; however, manual UT is too slow for large area 100% coverage scanning. Automatic UT is able to inspect up to 500 $ft^2/h$, but it does not work well with bad surface conditions in the area to be scanned. Also, there are problems of using couplant (the material used to couple the ultrasonic energy from the probe to the plate under test) in the working site.

(3) Magnetic-Flux-Leakage ("MFL") Method.

This method provides a high scan speed up to 1500 $ft^2/h$, so it is currently the most popular technique used for tank bottom inspection. However, as this method is sensitive to lift-off and has different sensitivity to near-side and far-side defects, it is used only as a tool for qualitative flow detection.

One remote field eddy current ("RFEC") technique was invented in 1951 (see MacClean, W. R., U.S. Pat. N0. 2,573,799, Nov. 1951, and Schmidt, T. R., "The Remote Field Eddy Current Inspection Technique.", *Materials Evaluation*, 42, pp. 225–230, February 1984) and is widely used as a nondestructive evaluation tool for inspecting metallic pipes and tubing. Essentially, the RFEC phenomenon can be observed when a coil is AC excited inside a conducting tube (see RFEC system 90 in prior-art Figure 1, in which excitation coil 91 is driven with an AC signal and creates direct signal path 95 and indirect signal path 96 which are detected by pick-up coil 94; defects in tubing 99 having center line 92 create signal changes as coil 91 and 94 are moved in tandem down the tubing 99). The RFEC signal can be sensed by a pick-up coil located 2–3 diameters away (i.e., 2 to 3 times the inner diameter dimension of the tubing) from the excitation coil. FIG. 1 shows a schematic of a prior-art RFEC probe system 90 for tube inspection and two signal paths 95 and 96, between the excitation coil 91 and the pick-up coil 94. The pick-up signal is closely related to the tube wall condition, thickness, permeability, and conductivity. The signal phase, especially, has approximately linear relationship with the tube wall thickness.

For tubing inspection, the RFEC technique is characterized by its substantially equal sensitivity to either an inner diameter ("ID") or an outer diameter ("OD") defect, its insensitivity to probe wobble or lift-off, and not being limited by the penetration depth, which has traditionally been a major disadvantage for conventional eddy-current techniques, especially in ferromagnetic material inspection. However, RFEC applications have been restricted to inspection of metallic tubing, although there is a need and demand for accurate and fast inspection for many flat-shaped metals, such as tank bottoms and vessel walls.

FIG. 2 shows the basic characteristics of the RFEC effect in a tubular product. Shown are two curves representing the logarithm of signal magnitude and the signal phase angle, respectively, as functions of the distance between the excitation and the pick-up coils. There are apparently two distinct regions, a near-field region and a remote-field region, separated by a transition zone. In the near field region, the signal magnitude attenuates exponentially, while the phase keeps approximately a constant value close to −90°. In the remote-field region, the magnitude attenuation rate is significantly reduced, while the phase keeps a constant value, but on which is different from that in the near-field region. The phase difference is approximately proportional to twice the wall thickness. In the region between the two regions, the transition zone, there is a rapid change in the magnitude attenuation rate and the phase value.

Users desire probes and techniques that are fast, reliable, accurate, easy to operate, and not expensive. One purpose of the present invention is to extend the RFEC technique to planar metallic plates. The proposed plate remote field eddy current ("PRFEC") technique herein meets all of the above requirements.

There is also a need therefore for an analysis of the PRFEC effect to be observed on metallic plates, and for a PRFEC probe for inspection of objects with flat geometry, or objects with approximately flat geometry in a least a local area.

SUMMARY OF THE INVENTION

The present invention provides a novel remote field eddy current probe, PRFEC probe, which has been developed for the non-destructive inspection of metallic (or other conducting), ferromagnetic and non-ferromagnetic, plates. Examples of such plates include petroleum storage tanks and aircraft wing skins, respectively. The probe detects, with good and substantially equal sensitivity, flaws irrespective of their locations and depth in the plate. It can detect, from one side of a plate, flaws located on the other side of the plate. This property makes it possible, using the novel probe, for non-destructive inspection of objects having restricted access, (e.g., access to only one side), such as the bottom plate of a huge tank which is sitting on the ground and thus has no access to the entire bottom of the tank.

The probe system has one or more excitation units and one or more receiver units. Each excitation unit includes an excitation coil and core which is driven with an alternating current (AC) signal to generate a magnetic field, and an auxiliary unit coupled to the excitation core. The function of the auxiliary unit is to guide the magnetic field into the conductive plate being inspected, and to minimize the field which leaks to the receiver unit(s) without passing through the plate being inspected. In one embodiment, the excitation unit has two excitation coils, namely a primary excitation coil and an auxiliary coil (which provides an adjustable control for the auxiliary unit). In one embodiment, there are one or more shielding covers made of a highly conducting material or of highly conducting materials. In one such embodiment, the highly conducting materials are laminated with alternating layers of ferromagnetic materials. In one embodiment, the remote-field eddy-current probe system has an excitation unit shielding cover which is separate from the shielding cover of the receiver unit. In another embodiment, the remote-field eddy-current probe system has a single shield in which the excitation unit shielding cover is part of a shielding cover for both the excitation unit and the pick-up unit. Each receiver unit includes a magnetic field detector capable of detecting weak magnetic fields, such as a receiver coil having a high number of turns about a shaped magnetic core, or a magneto-resistive element, or a superconducting quantum interference device (SQUID). In one embodiment, the receiver unit is located in a remote-field region relative to the excitation unit, and measures the magnitude, phase, or both, of the which penetrated and spread along the plate surface of the plate-under-inspection from the excitation unit. Defects in the plate cause the field to deflect from its normal path in the plate, and thus be detected by the receiver unit(s).

The probe system is designed to have the electromagnetic energy released from the excitation coils penetrate through the plate twice, so that the signal received by one of the pickup coils has passed twice through the plate wall, from one side of the plate at the excitation unit to the other side and from the other side back to the original side at the receiver unit. The specially designed magnetic core for excitation unit, along with carefully chosen magnitude and phase parameters for the primary and auxiliary excitation currents in their respective coils, enable the probe to detect flaws and other features without being overloaded with directly-coupled signal. A highly conducting cover, or several highly conducting covers, minimize the energy leakage around the plate. Since the receiver unit, or units, sense the electromagnetic field that has penetrated the plate twice, the magnitude and phase of the received signal(s) are responsive to the plate wall conditions (the plate's thickness, permeability and conductivity). Especially, the phase delay, relatively to the phase of the primary excitation current, is proportional to the total wall thickness. As the result, the signal phase is linearly related to the depth of a flaw irrespective to the flaw's location.

BRIEF DESCRIPTION OF THE DRAWINGS

The features of the invention as well as objects and advantages will be best understood by reference to the appended claims, detailed description of particular embodiments and accompanying drawings where:

FIG. 9A is a graph of flux magnitude as a function of distance comparing zero defect and five defect sizes; entitled "Basic Characteristics of Model EZ42:2", Flux Magnitude Distribution Under Detector for Circumferential Defects of Different Depths.

Primary Coil 102=C–Main coil, about 1000 ampere-turns,

Auxiliary Coil 103=F–Compensation coil, about 50–100 ampere turns (adjustable) and shifted (10–30 degrees) in phase (adjustable), Cover 208=S–Steel, relative initial permeability $\mu_r$–70, conductivity s–$0.7 \times 10^7$s, Excitation Core 101 and Pick-Up Core 204=T–Ferrite, soft, relative permeability $\mu_r=1000$ Shield 106=R–Aluminum, conductivity s=$3.5 \times 10^7$s.

Figure 13:
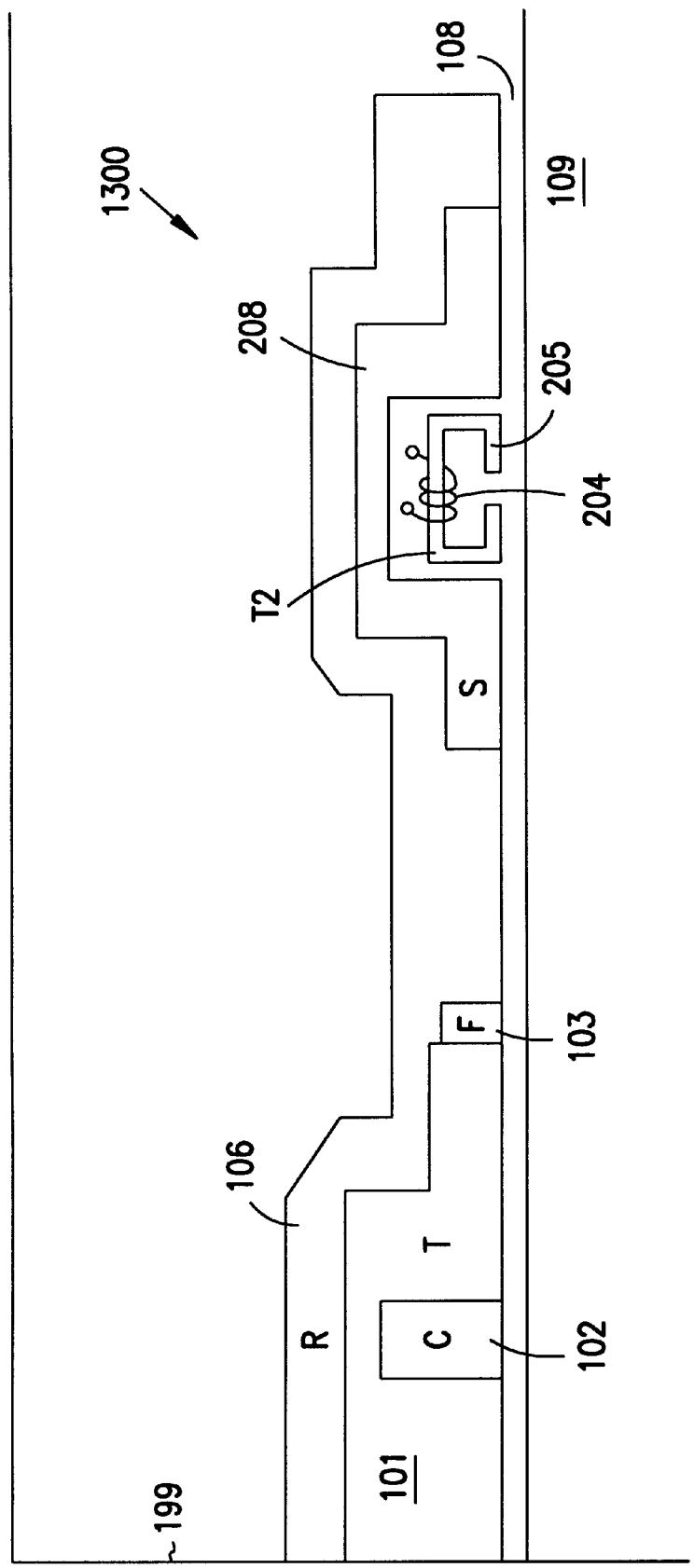
FIG. 13 shows a radial cross section, starting at centerline 199 and extending in a vertical plane, of another exemplary PRFEC probe 1300 according to the present invention; entitled "RFEC Prove for Steel Plates Model EZ00: An Overview" and annotated.
Figure 14:
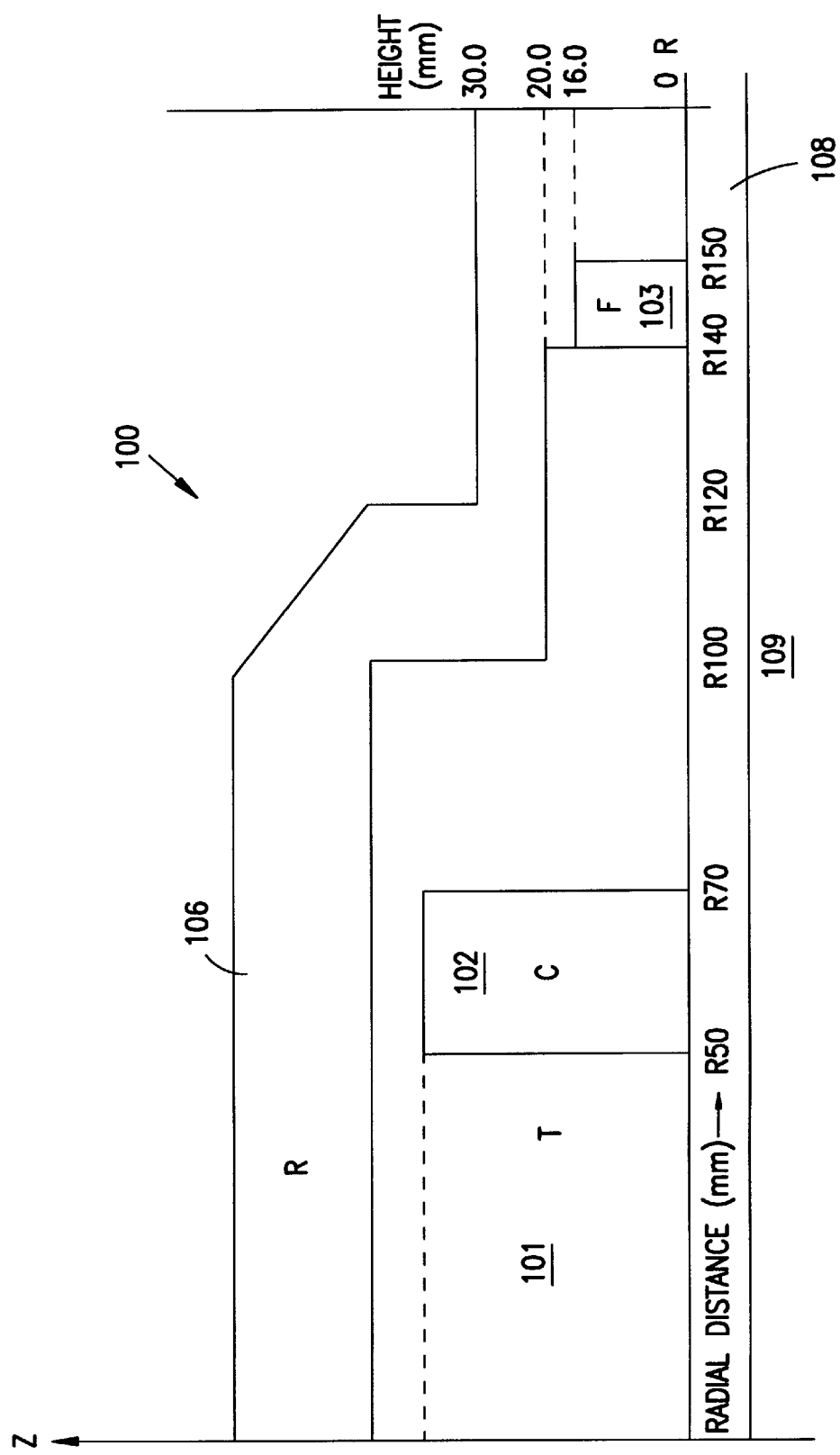

FIG. 14 shows a radial cross section of the excitation part 100 of PRFEC probe 1300 as shown in FIG. 13; entitled "RFEC Probe for Steel Plates Model EZ00: Primary Part."

Figure 15:
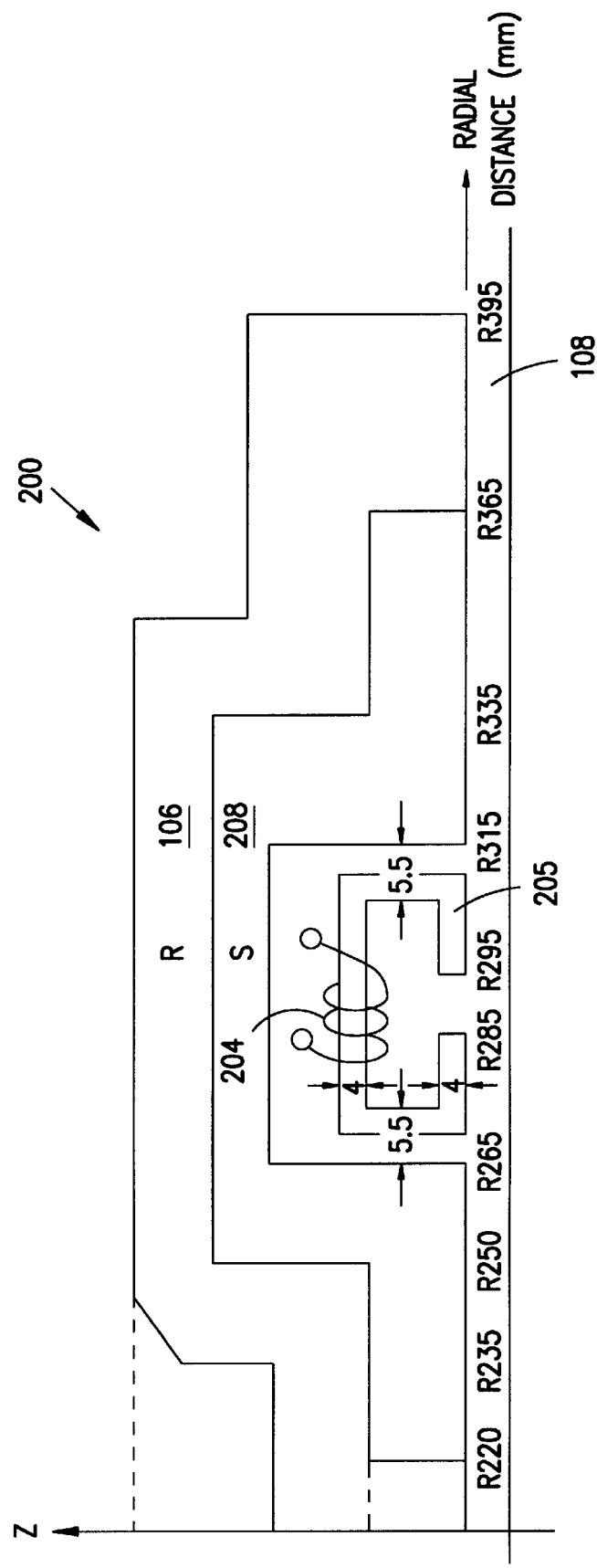

FIG. 15 shows a radial cross section of the pick-up part 200 of PRFEC probe 1300 as shown in FIG. 13; entitled "RFEC Probe for Steel Plates Model EZ00: Secondary Part."

Figure 16:
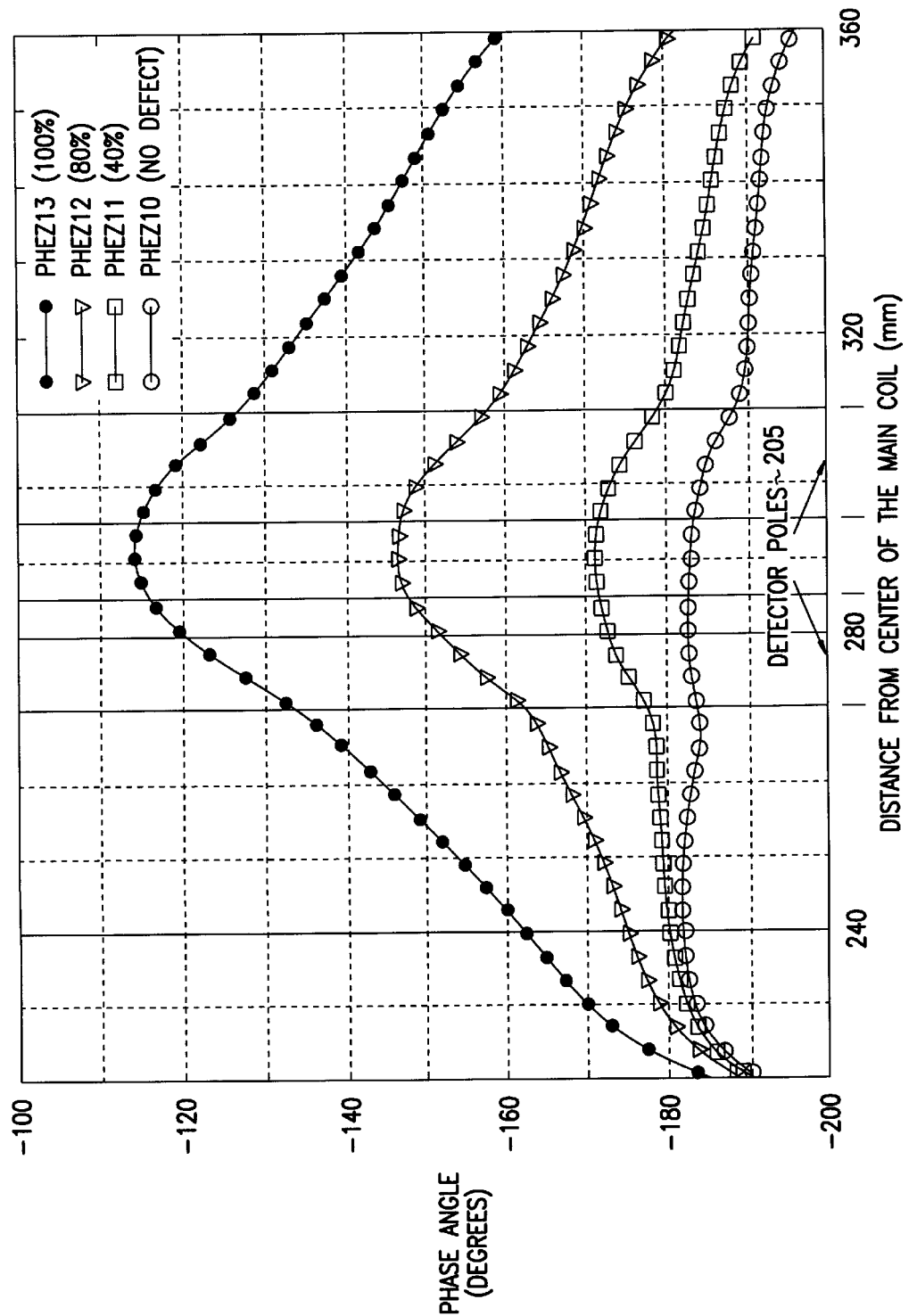

FIG. 16 shows a graph of flux phase variation under the pick-up part 200 of PRFEC probe 1300 due to a defect of different depths in the steel plate 109 under inspection: defect under the detector 200; entitled "Flux Phase Variation Due to a Defect Under the Detector."

Figure 17:
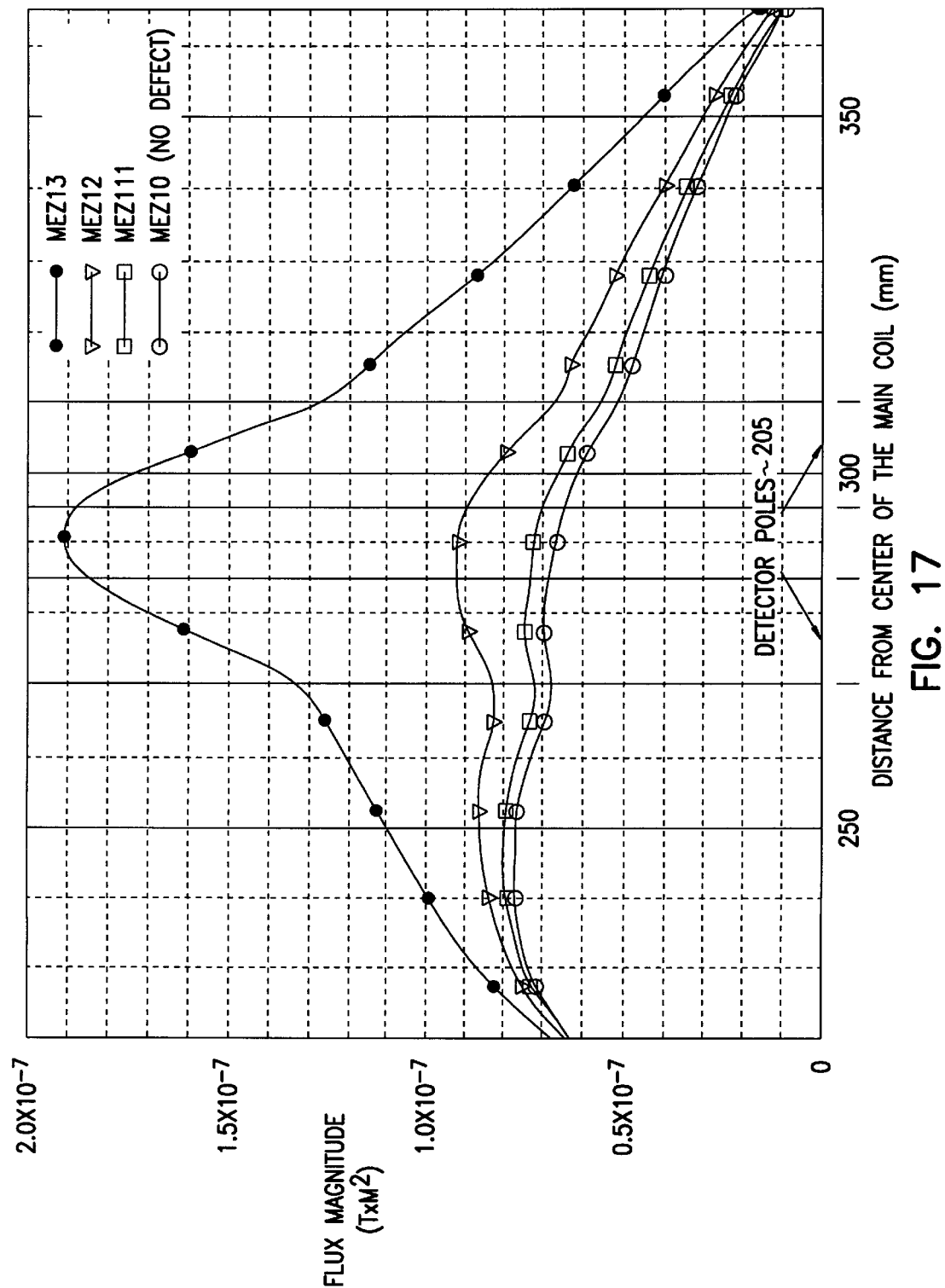

FIG. 17 shows a graph of flux magnitude variation under the pick-up part 200 of PRFEC probe 1300 due to a defect of different depths in the steel plate 109 under inspection: defect under the detector 200; entitled "Flux Magnitude Variation Due to a Defect Under the Detector."

Figure 18:
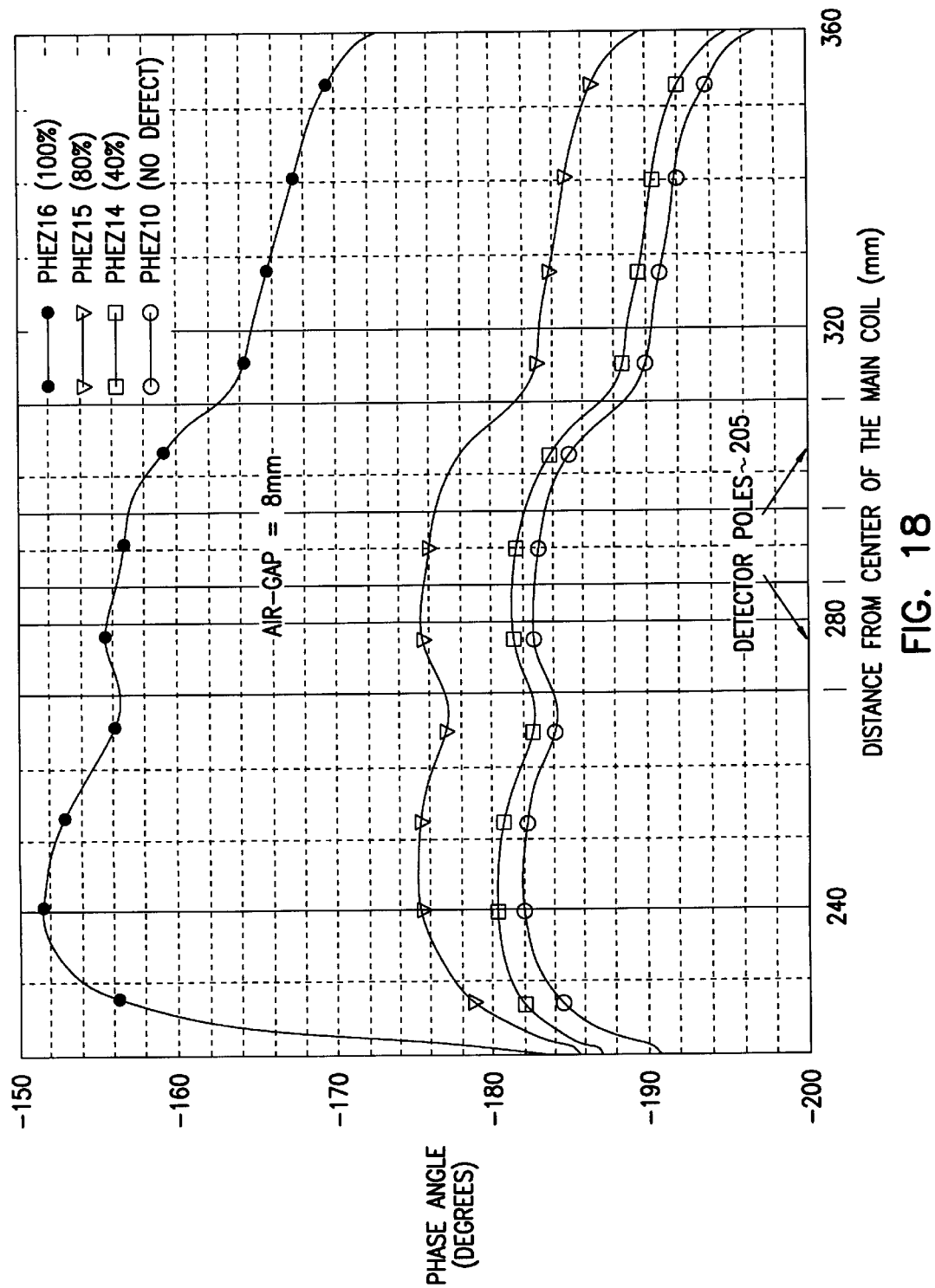

FIG. 18 shows a graph of flux phase variation under the pick-up part 200 of PRFEC probe 1300 due to a defect of different depths in the steel plate 109 under inspection: defect under the auxiliary coil 103; entitled "Flux Phase Variation Due to a Defect Under the Coil F."

Figure 19:
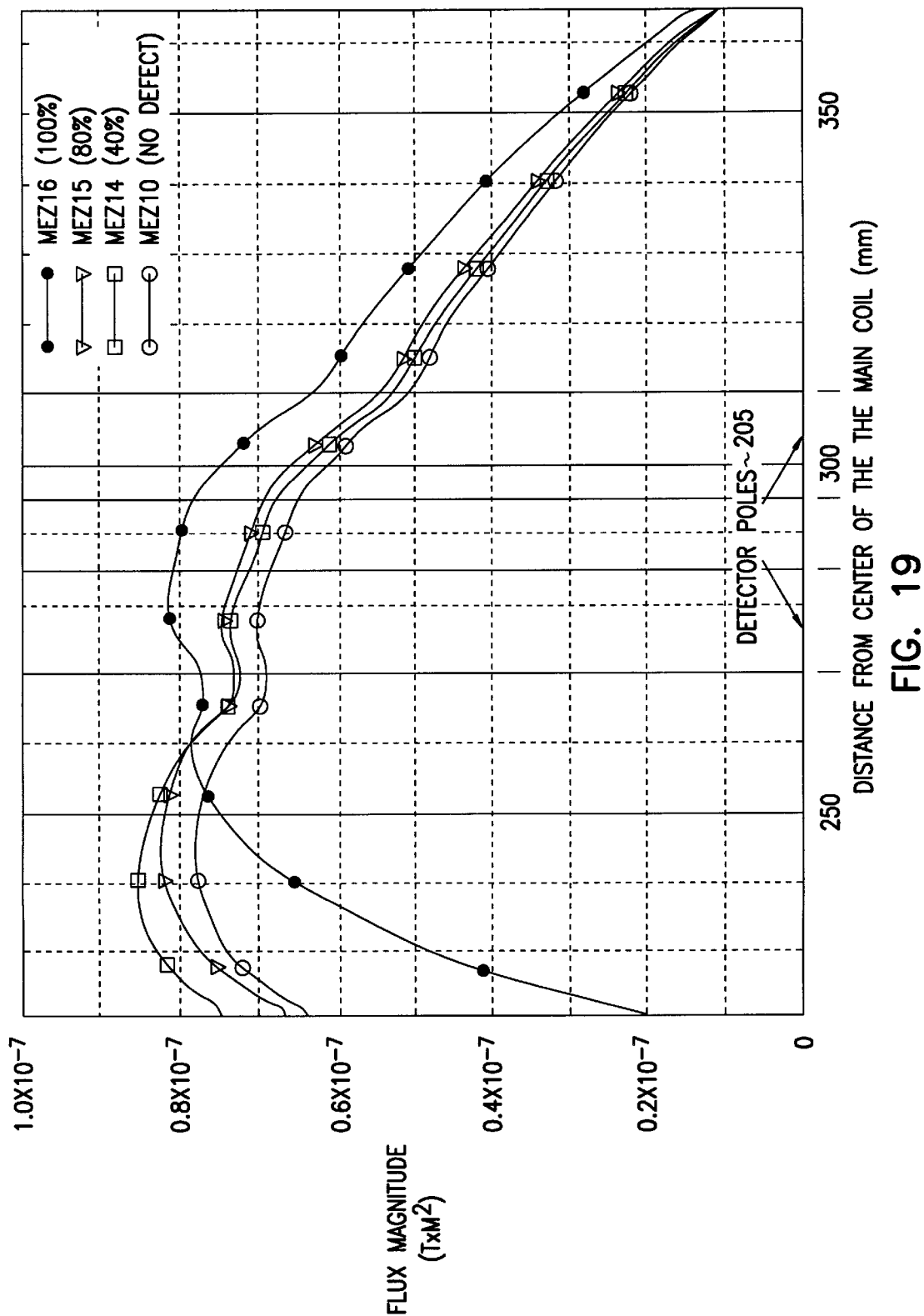

FIG. 19 shows a graph of flux magnitude variation under the pick-up part 200 of PRFEC probe 1300 due to a defect of different depths in the steel plate 109 under inspection: defect under the auxiliary coil 103; entitled "Flux Magnitude Variation Due to a Defect Under the Coil F."

Figure 20:
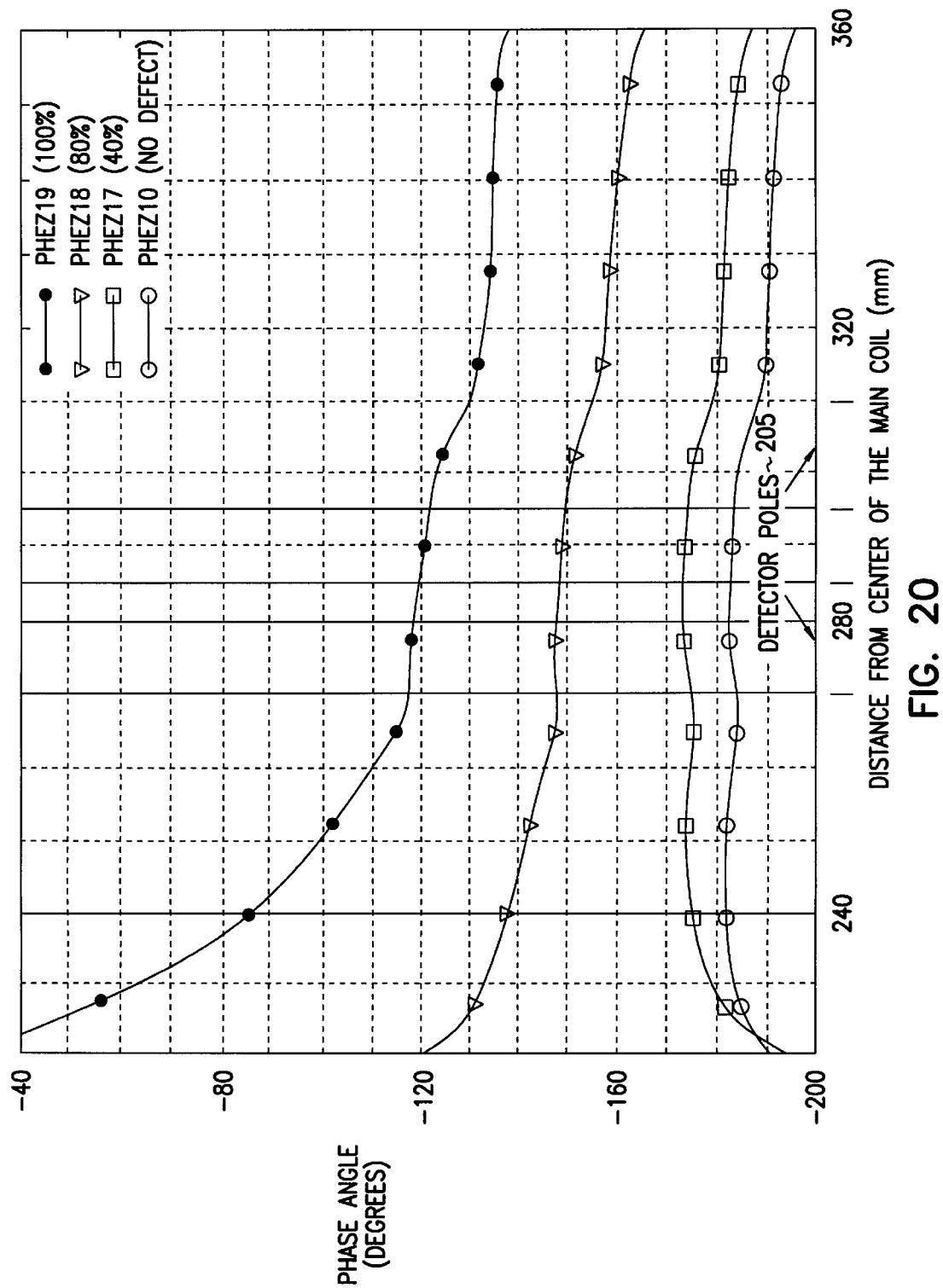

FIG. 20 shows a graph of flux phase variation under the pick-up part 200 of PRFEC probe 1300 due to a defect of different depths in the steel plate 109 under inspection: defect under the primary coil 102; entitled "Flux Phase Variation Due to Defect Under the Main Coil."

Figure 21:
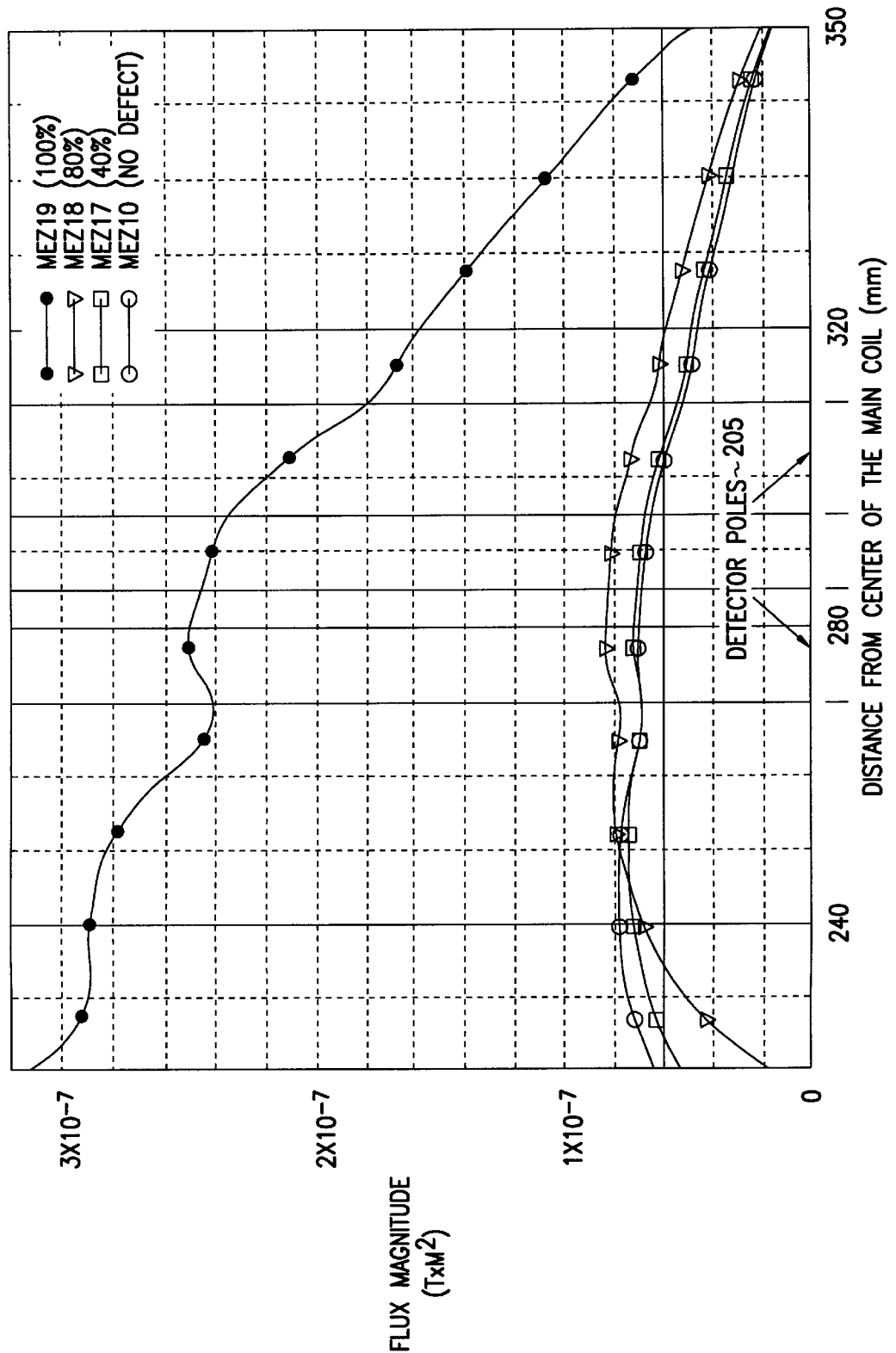

FIG. 21 shows a graph of flux magnitude variation under the pick-up part 200 of PRFEC probe 1300 due to a defect of different depths in the steel plate 109 under inspection: defect under the primary coil 102; entitled "Flux Magnitude Variation Due to a Defect Under the Main Coil."

Figure 22:
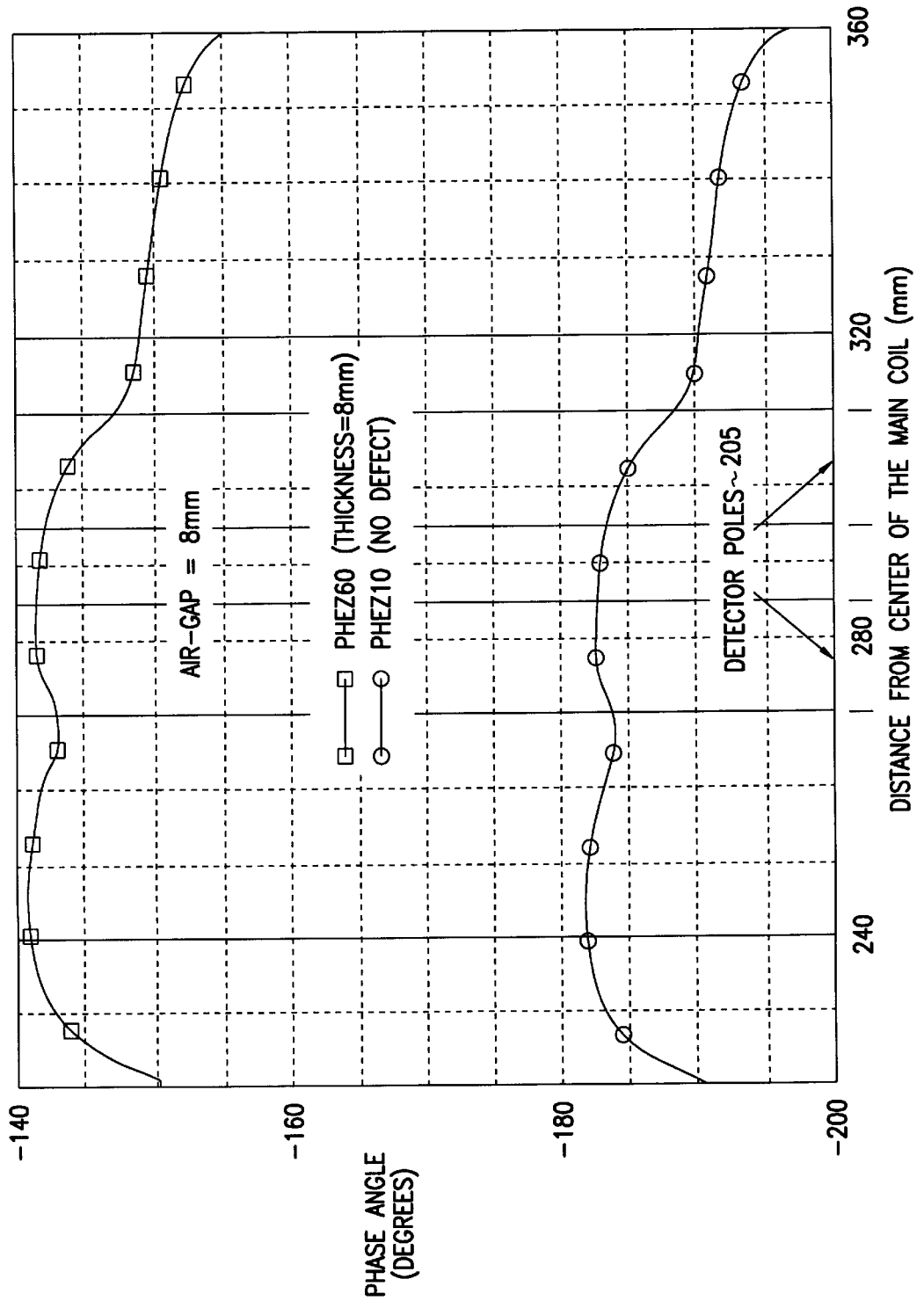

FIG. 22 shows a graph of flux phase variation under the pick-up part 200 of PRFEC probe 1300 due to a defect of different depths in the steel plate 109 under inspection: defect is a 20% general wall thinning; entitled "Flux Phase Variation Due to a General Wall Thinning."

Figure 23:
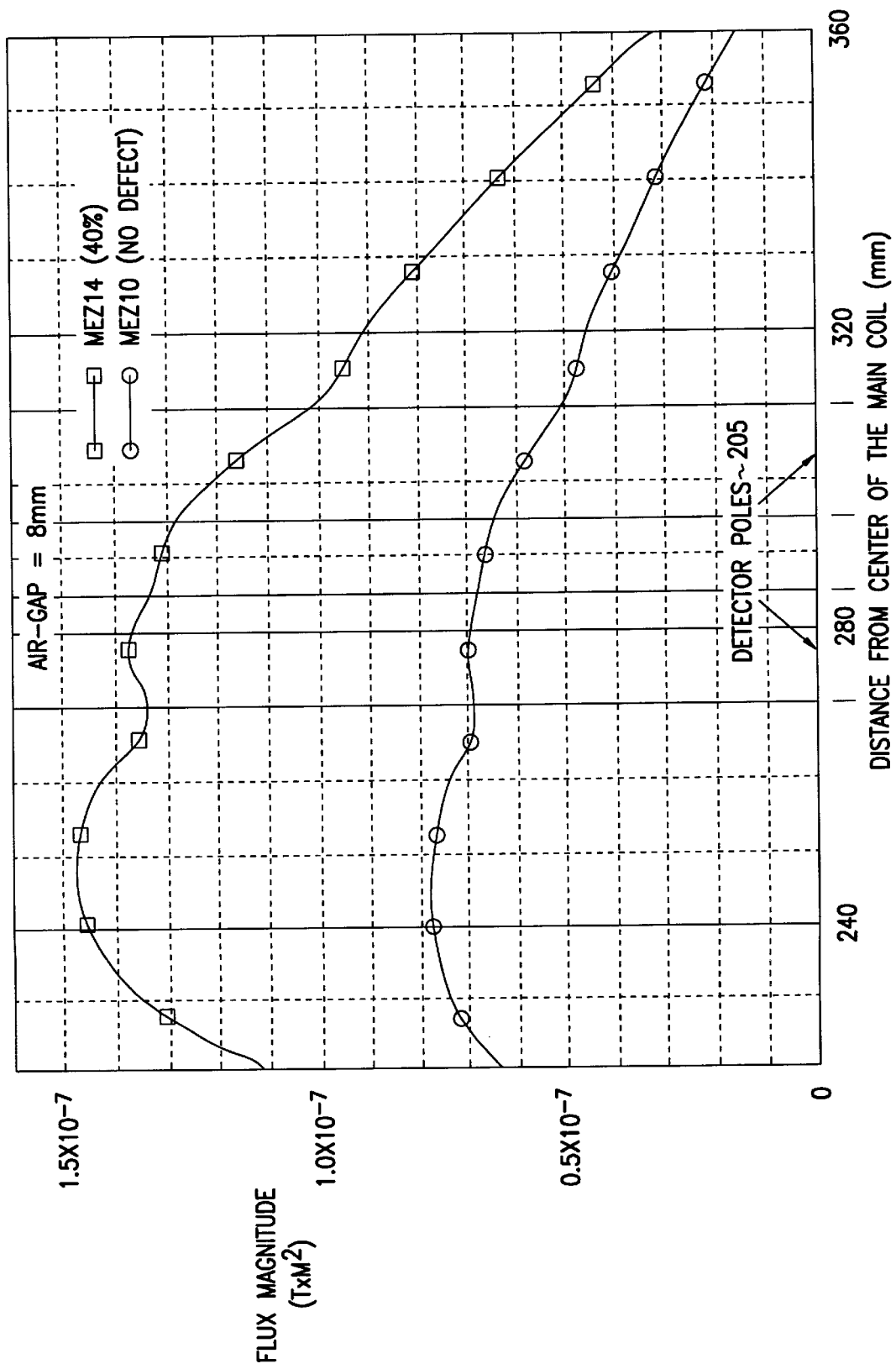

FIG. 23 shows a graph of flux magnitude variation under the pick-up part 200 of PRFEC probe 1300 due to a defect of different depths in the steel plate 109 under inspection: defect is a 20% general wall thinning; entitled "Flux Magnitude Variation Due to a General Wall Thinning."

Figure 24:
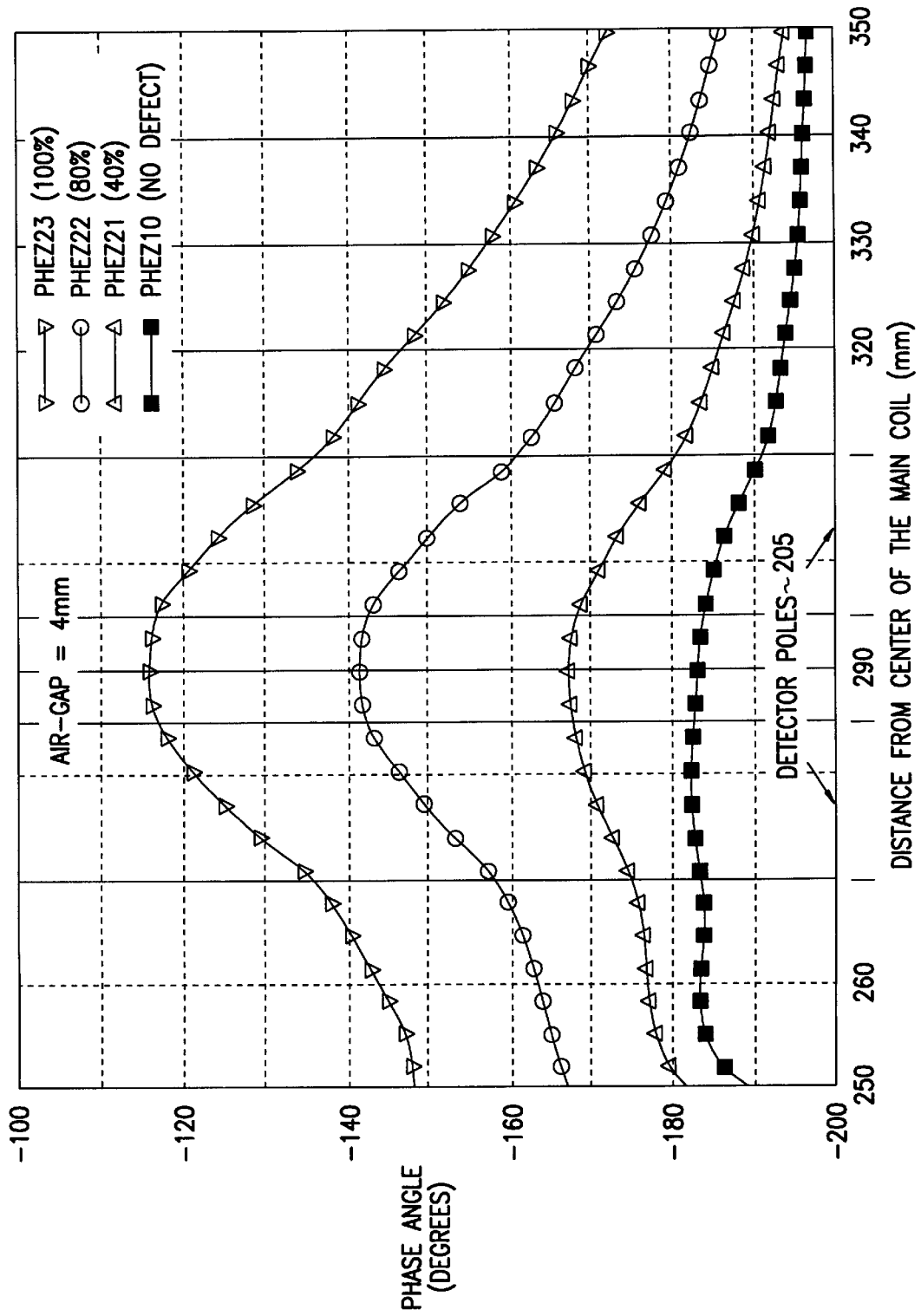

FIG. 24 shows a graph of flux phase variation under the pick-up part 200 of PRFEC probe 1300 due to a defect of different depths in the steel plate 109 under inspection: defect under the detector 200 at a reduced air-gap 108 of 4 mm; entitled "Flux Phase Variation Due to a Defect Under the Detector."

Figure 25:
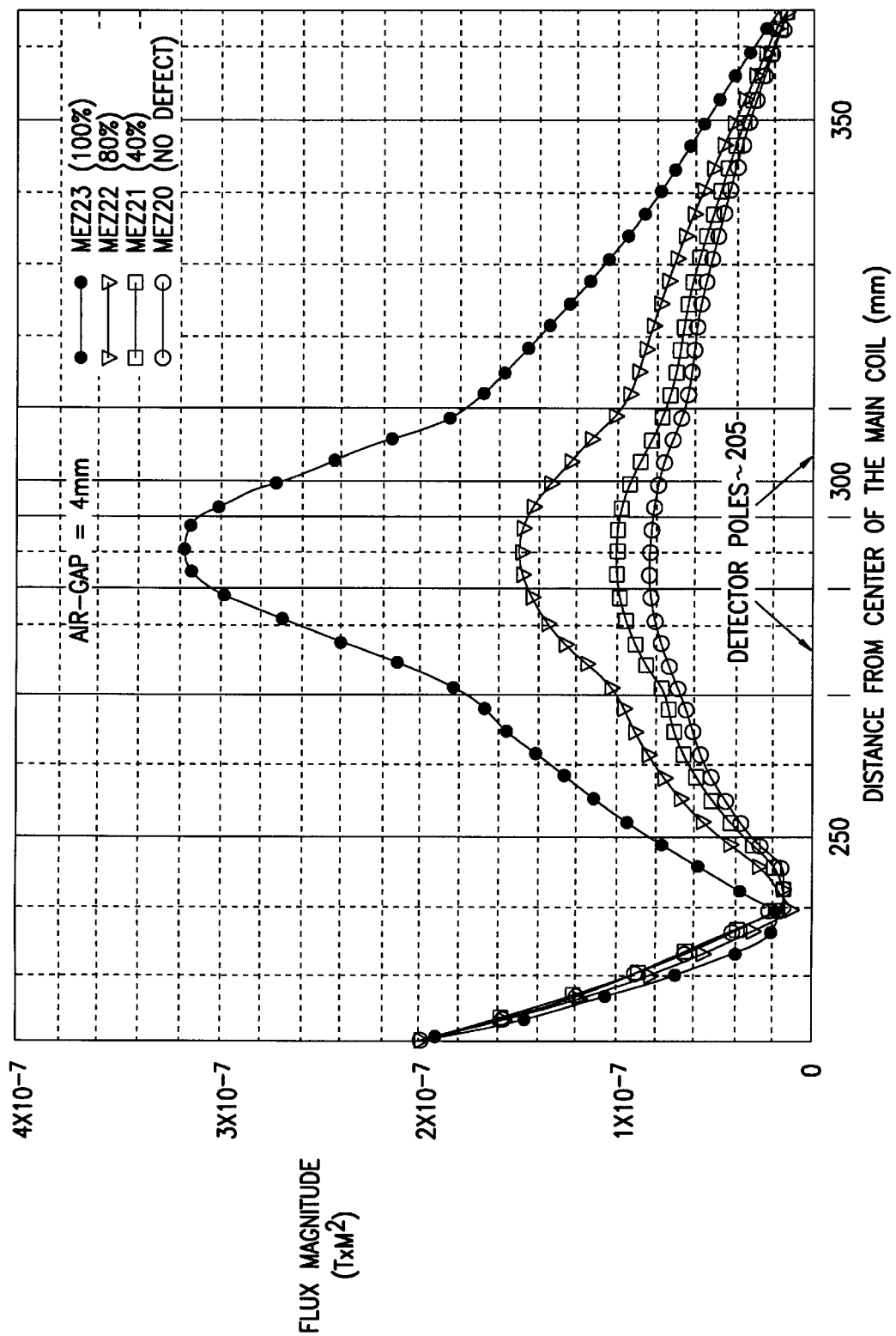

FIG. 25 shows a graph of flux magnitude variation under the pick-up part 200 of PRFEC probe 1300 due to a defect of different depths in the steel plate 109 under inspection: defect under the detector 200 at a reduced air-gap 108 of 4 mm; entitled "Flux Magnitude Variation Due to a Defect Under the Detector."

Figure 26:
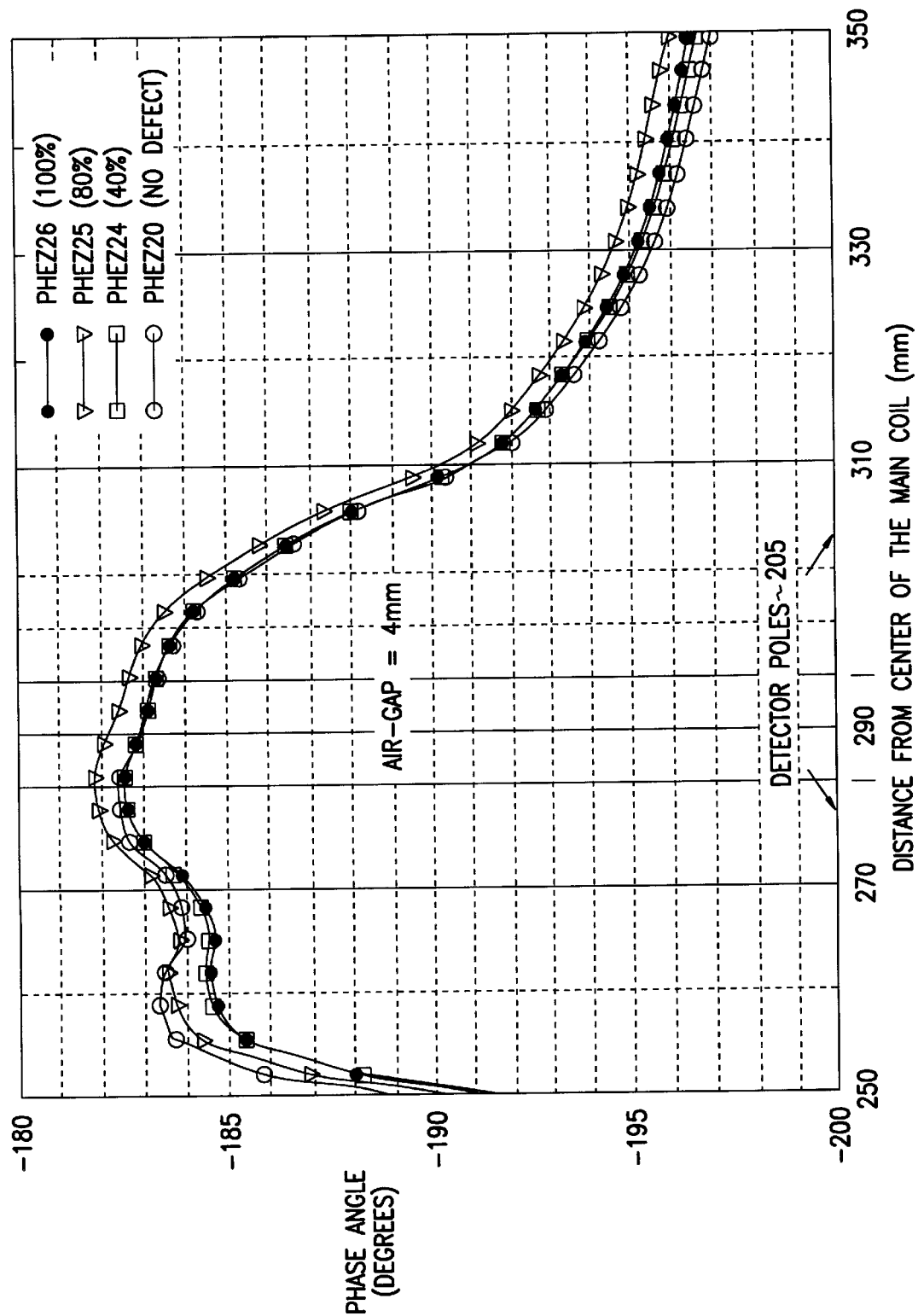

FIG. 26 shows a graph of flux phase variation under the pick-up part 200 of PRFEC probe 1300 due to a defect of different depths in the steel plate 109 under inspection: defect under the auxiliary coil 103 at a reduced air-gap 108 of 4 mm; entitled "Flux Phase Variation Due to a Defect Under Coil F."

Figure 27:
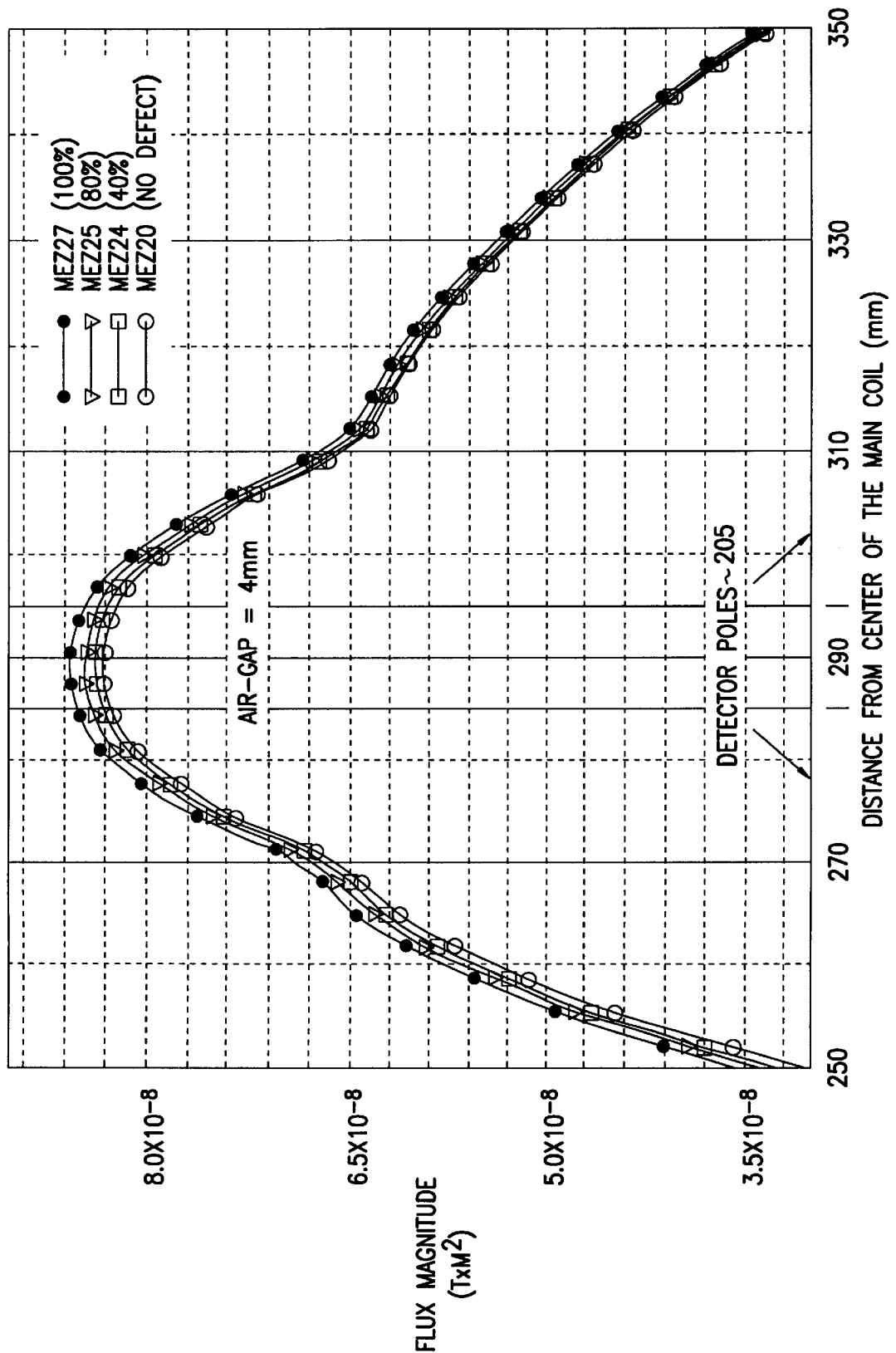

FIG. 27 shows a graph of flux magnitude variation under the pick-up part 200 of PRFEC probe 1300 due to a defect of different depths in the steel plate 109 under inspection: defect under the auxiliary coil 103 at a reduced air-gap 108 of 4 mm; entitled "Flux Magnitude Variation Due to a Defect Under Coil F."

Figure 28:
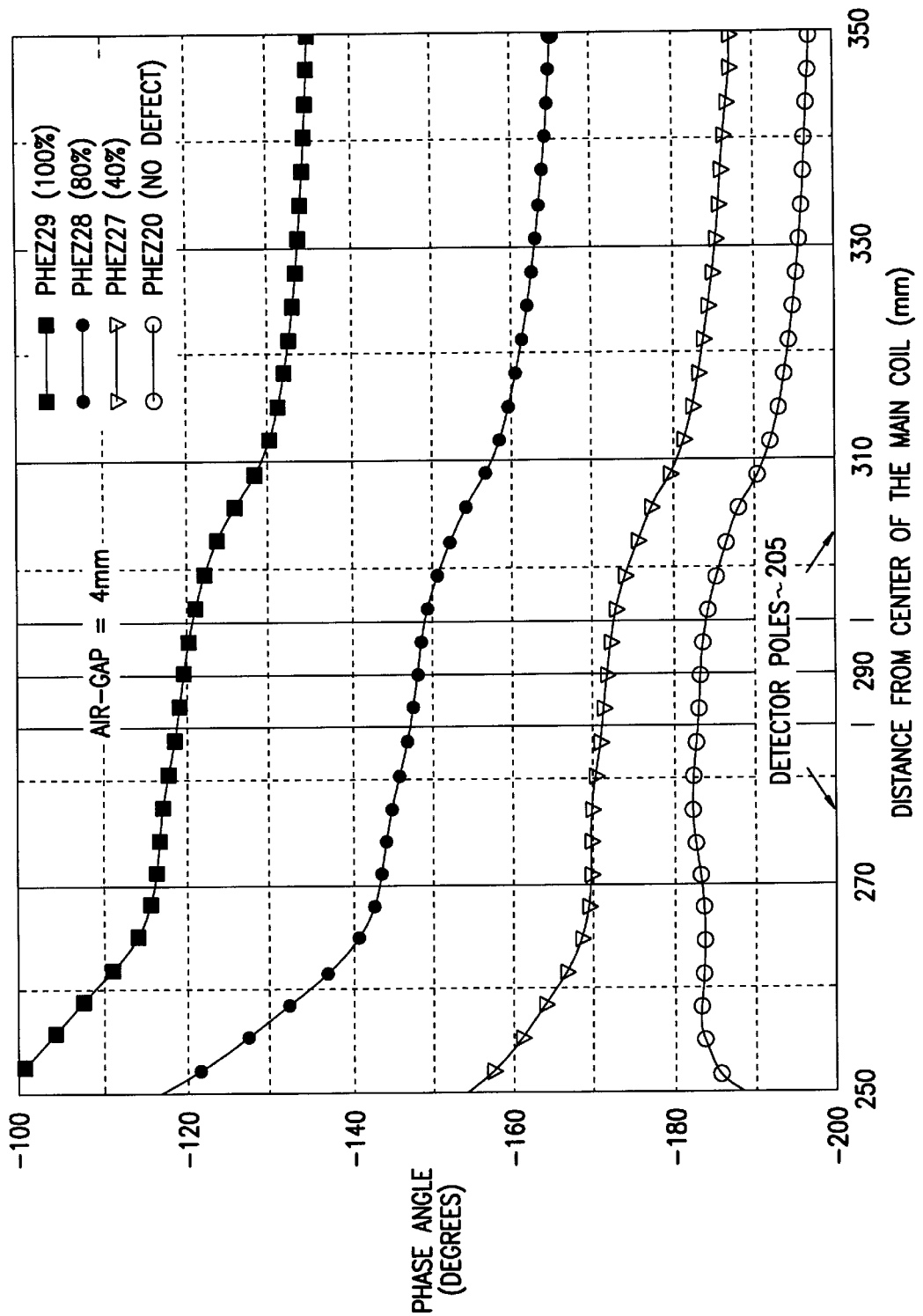

FIG. 28 shows a graph of flux phase variation under the pick-up part 200 of PRFEC probe 1300 due to a defect of different depths in the steel plate 109 under inspection: defect under the primary coil 102 at a reduced air-gap 108 of 4 mm; entitled "Flux Phase Variation Due to a Defect Under the Main Coil."

Figure 29:
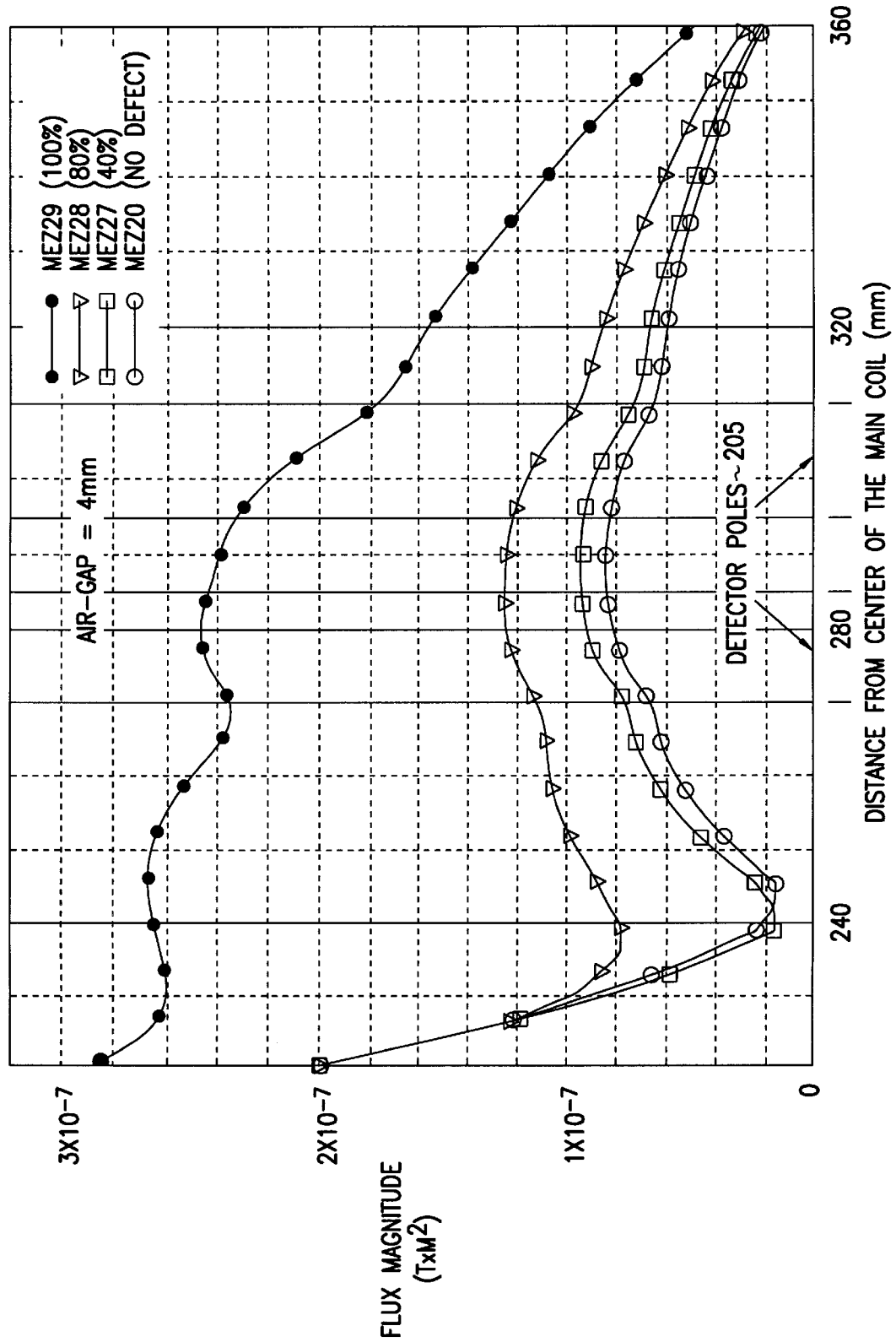

FIG. 29 shows a graph of flux magnitude variation under the pick-up part 200 of PRFEC probe 1300 due to a defect of different depths in the steel plate 109 under inspection: defect under the primary coil 102 at a reduced air-gap 108 of 4 mm; entitled "Flux Magnitude Variation Due to a Defect Under the Main Coil."

Figure 30:
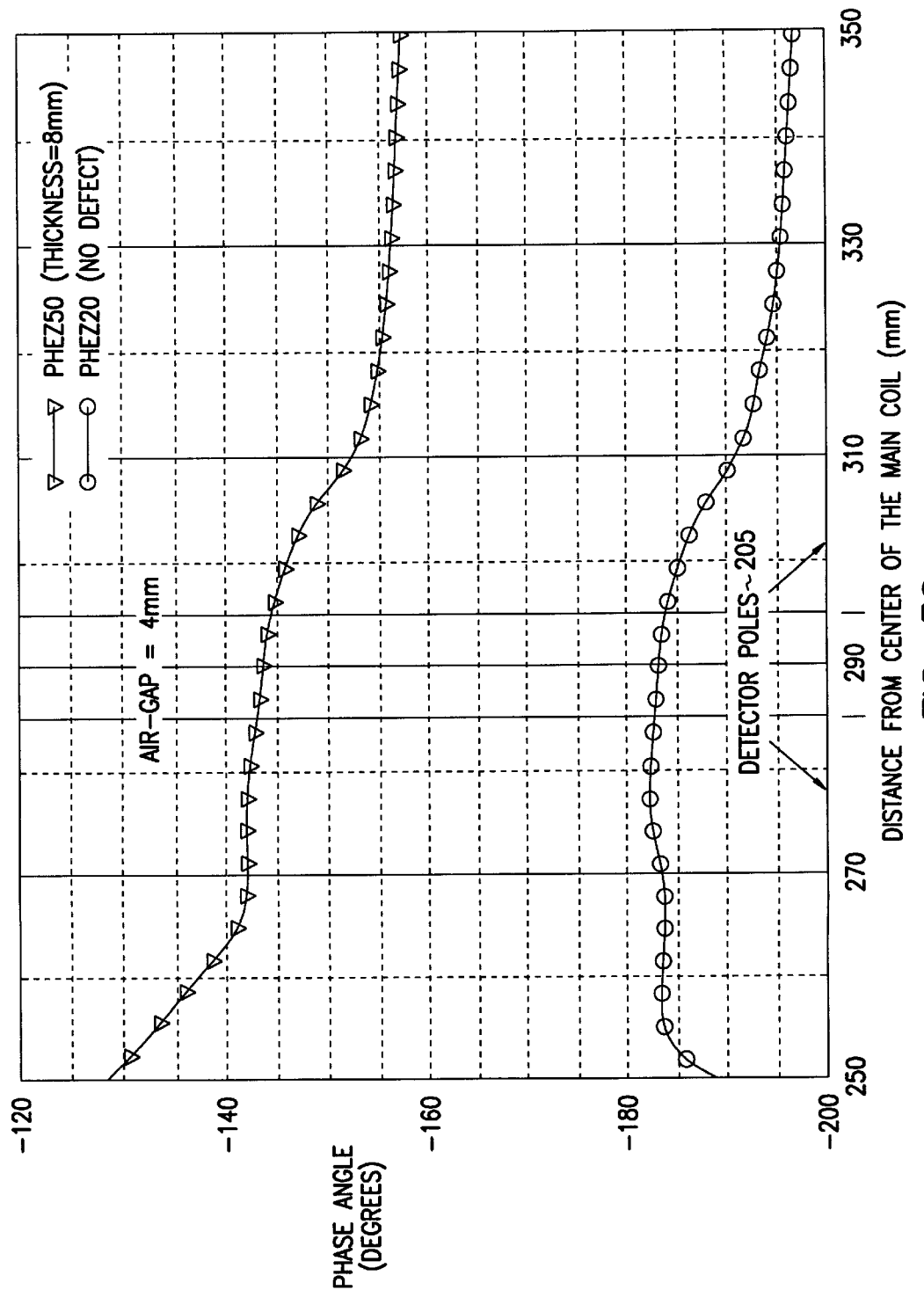

FIG. 30 shows a graph of flux phase variation under the pick-up part 200 of PRFEC probe 1300 due to a defect of different depths in the steel plate 109 under inspection: defect is a 20% general wall thinning at a reduced air-gap 108 of 4 mm; entitled "Flux Phase Variation Due to a Defect Under the Detector."

Figure 31:
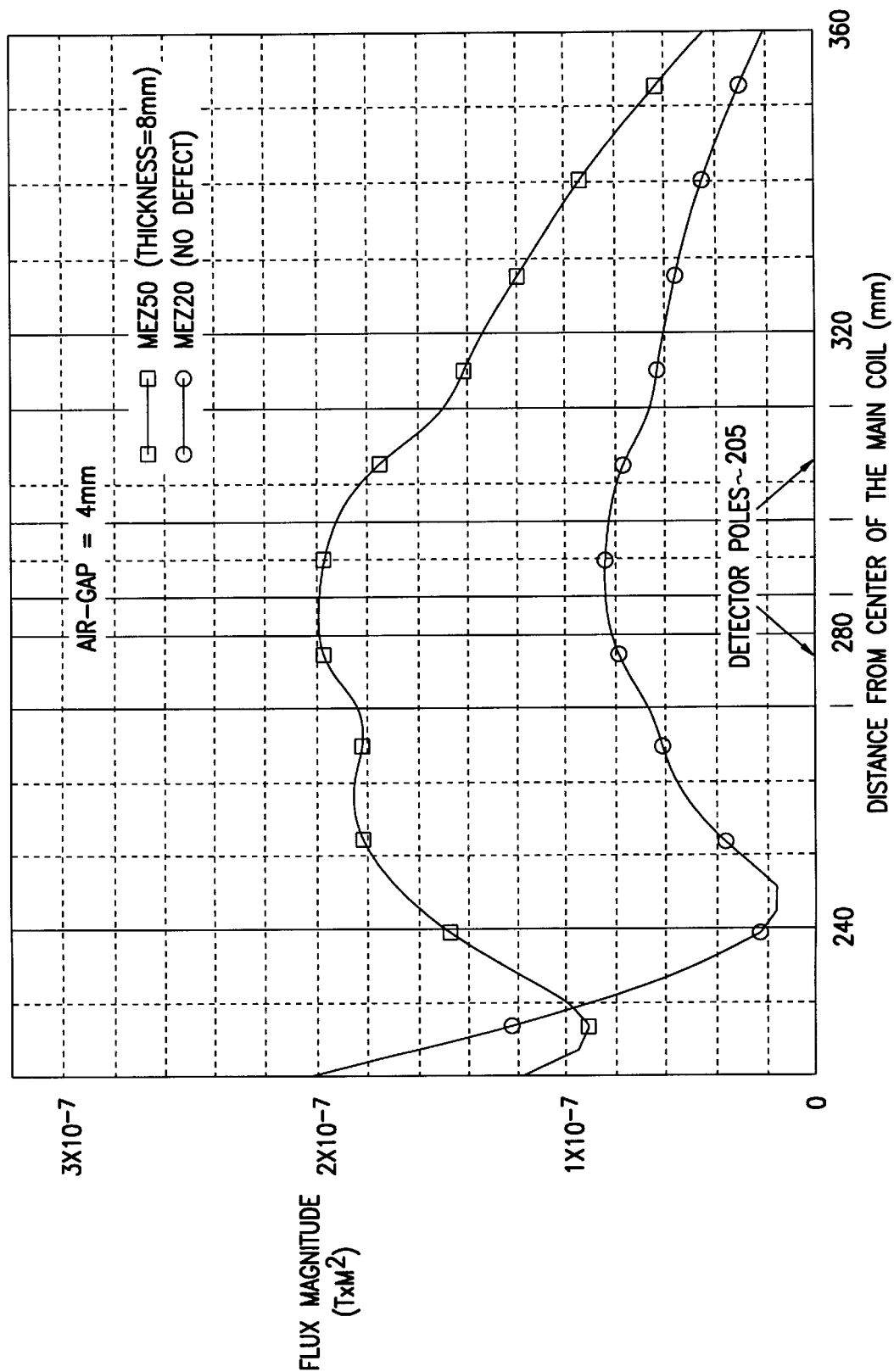

FIG. 31 shows a graph of flux magnitude variation under the pick-up part 200 of PRFEC probe 1300 due to a defect of different depths in the steel plate 109 under inspection: defect is a 20% general wall thinning at a reduced air-gap 108 of 4 mm; entitled "Flux Magnitude Variation Due to a General Wall Thinning."

Figure 32:
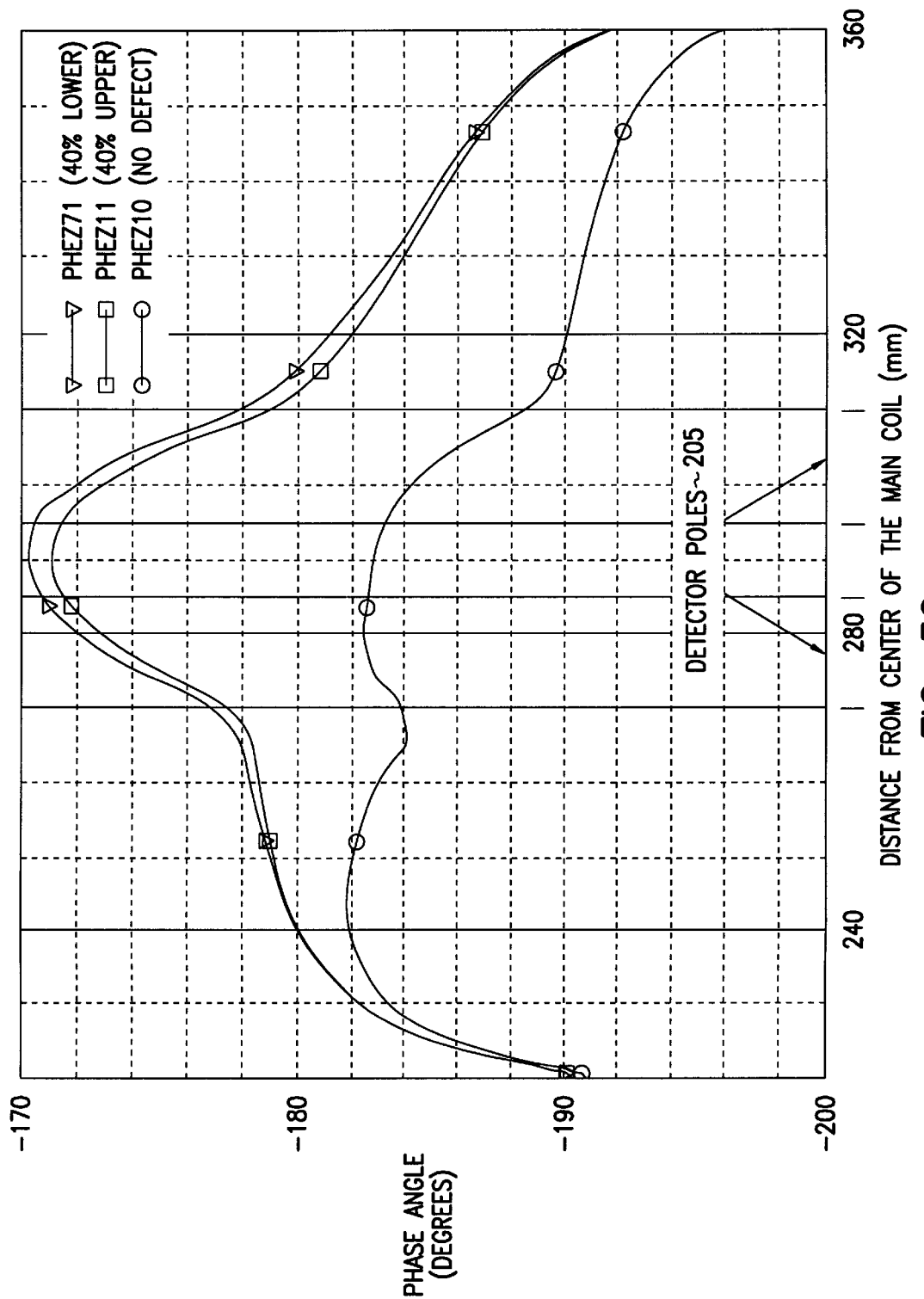

FIG. 32 shows a graph of flux phase variation under the pick-up part 200 of PRFEC probe 1300 due to a defect of different depths in the steel plate 109 under inspection: variation due to an upper surface defect and a lower surface defect, defect under the detector 200; entitled "Flux Phase Variation Due to a Defect Under the Detector."

Figure 33:
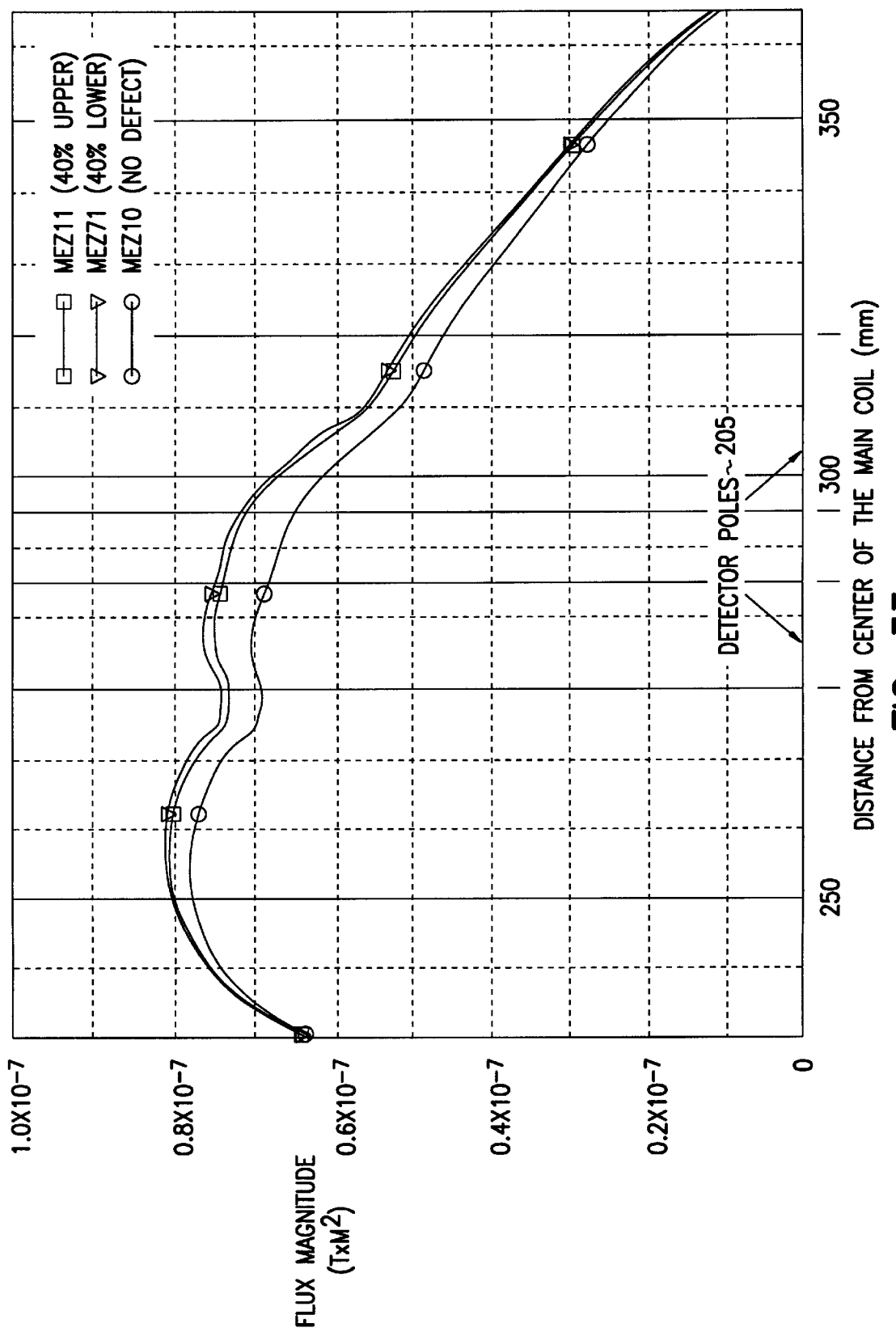

FIG. 33 shows a graph of flux magnitude variation under the pick-up part 200 of PRFEC probe 1300 due to a defect of different depths in the steel plate 109 under inspection: variation due to an upper surface defect and a lower surface defect, defect under the detector 200, entitled "Flux Magnitude Variation Due to a Defect Under the Detector."

Figure 34:
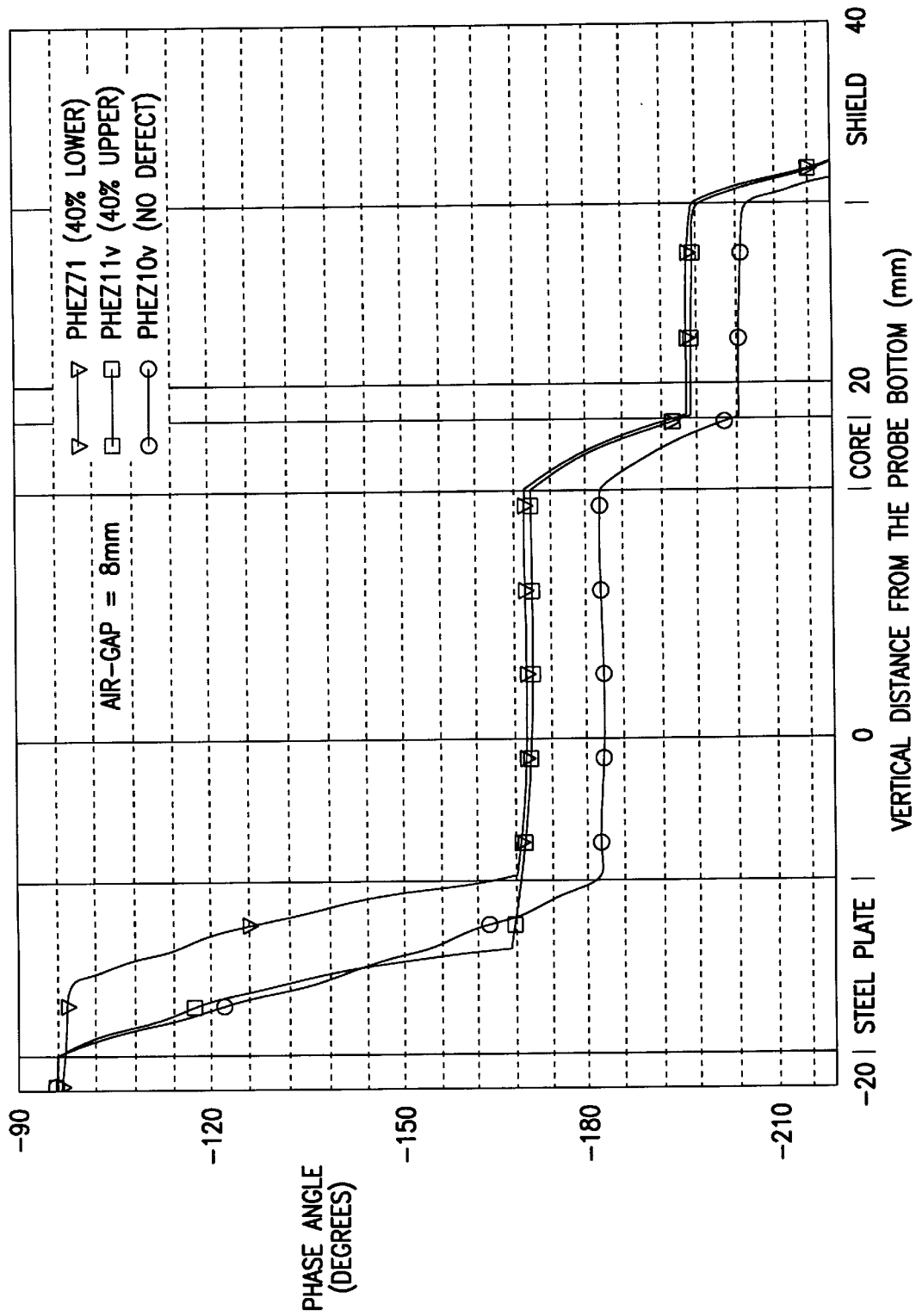

FIG. 34 shows a graph of flux phase-variation along the vertical center line of the detector 200 of PRFEC probe 1300 due to a defect of different depths in the steel plate 109 under inspection: variation due to an upper surface defect and a lower surface defect, defect under the detector 200; entitled "Flux Phase Change Along the Center Line of the Detector."

Figure 35:
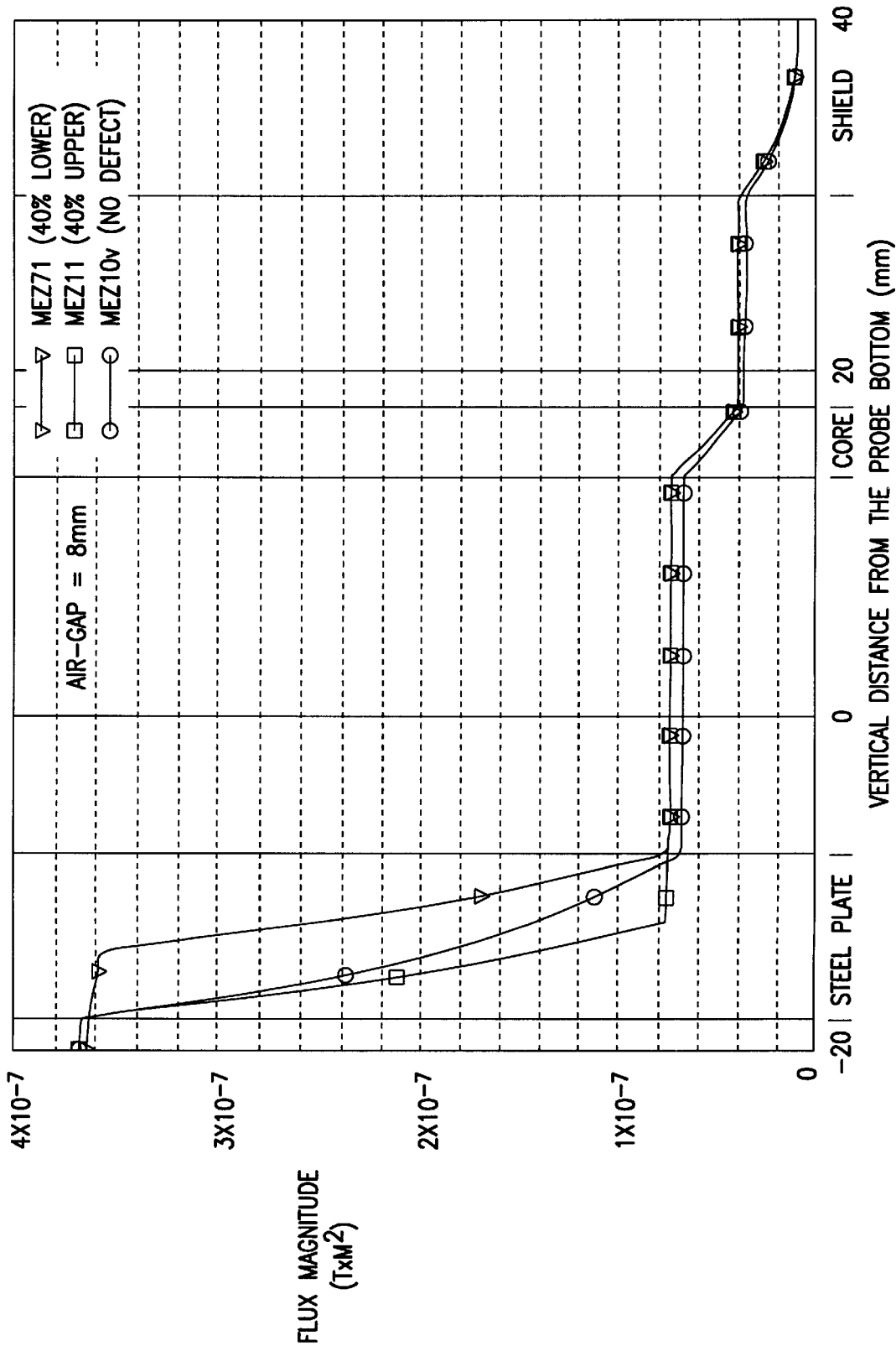

FIG. 35 shows a graph of flux magnitude variation along the vertical center line of the detector 200 of PRFEC probe 1300 due to a defect of different depths in the steel plate 109 under inspection: variation due to an upper surface defect and a lower surface defect, defect under the detector 200; entitled "Flux Magnitude Change Along the Center Line of the Detector."

Figure 36:
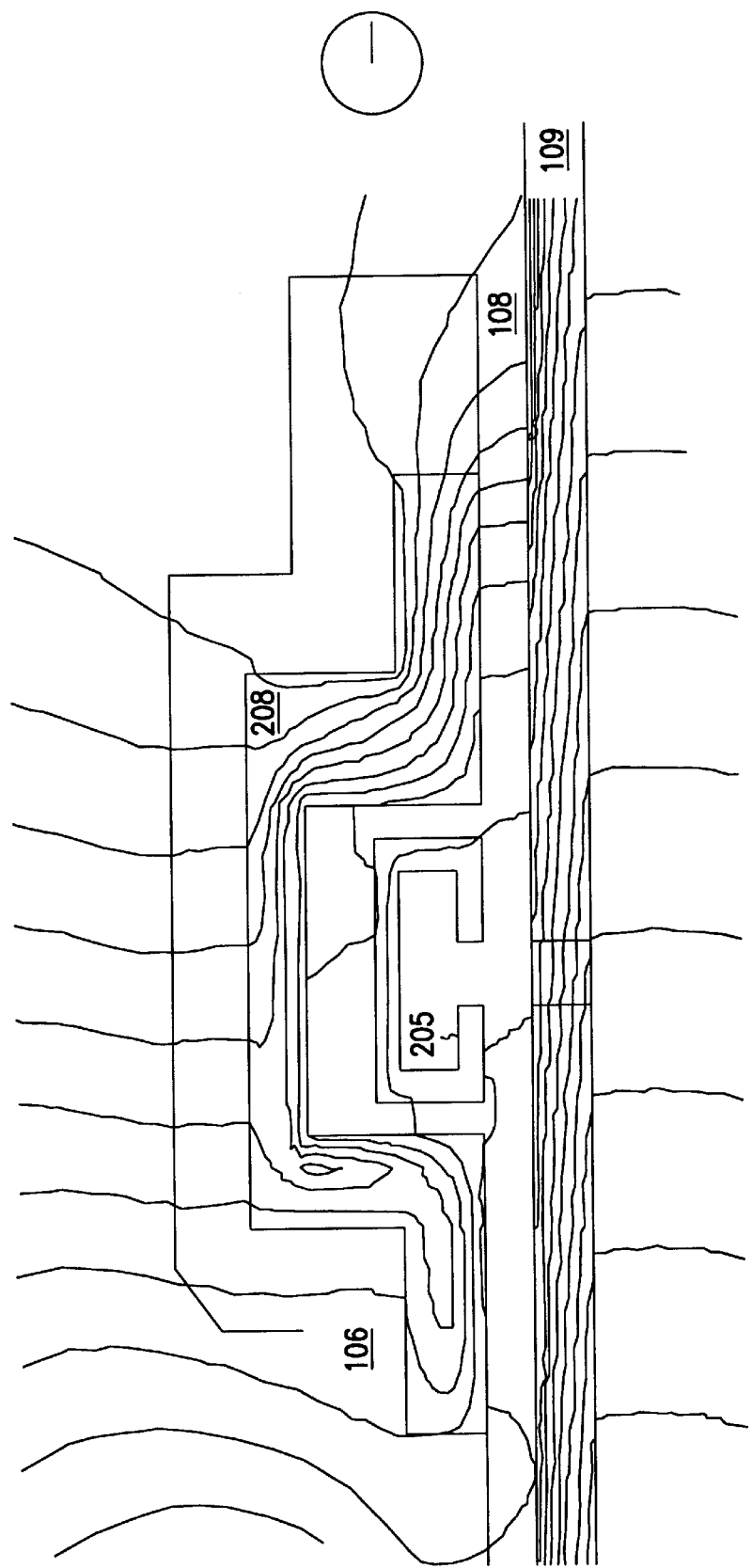

FIG. 36 shows a graph of the natural logarithm of the absolute value of magnitude variation (equi-potentials of ln (|AR|), where A=magnetic vector potential, and R=radius in cylindrical coordinates) in the region of detector 200 for a non-defect case; entitled "PRFEC Probe for Steel Plates Model EZ00"; and annotated:

EQUI-LN<1 AR 1>: GAP=8 mm. No Defect 200 mm<X<400 mm–40 mm<Y<80 mm.

Figure 37:
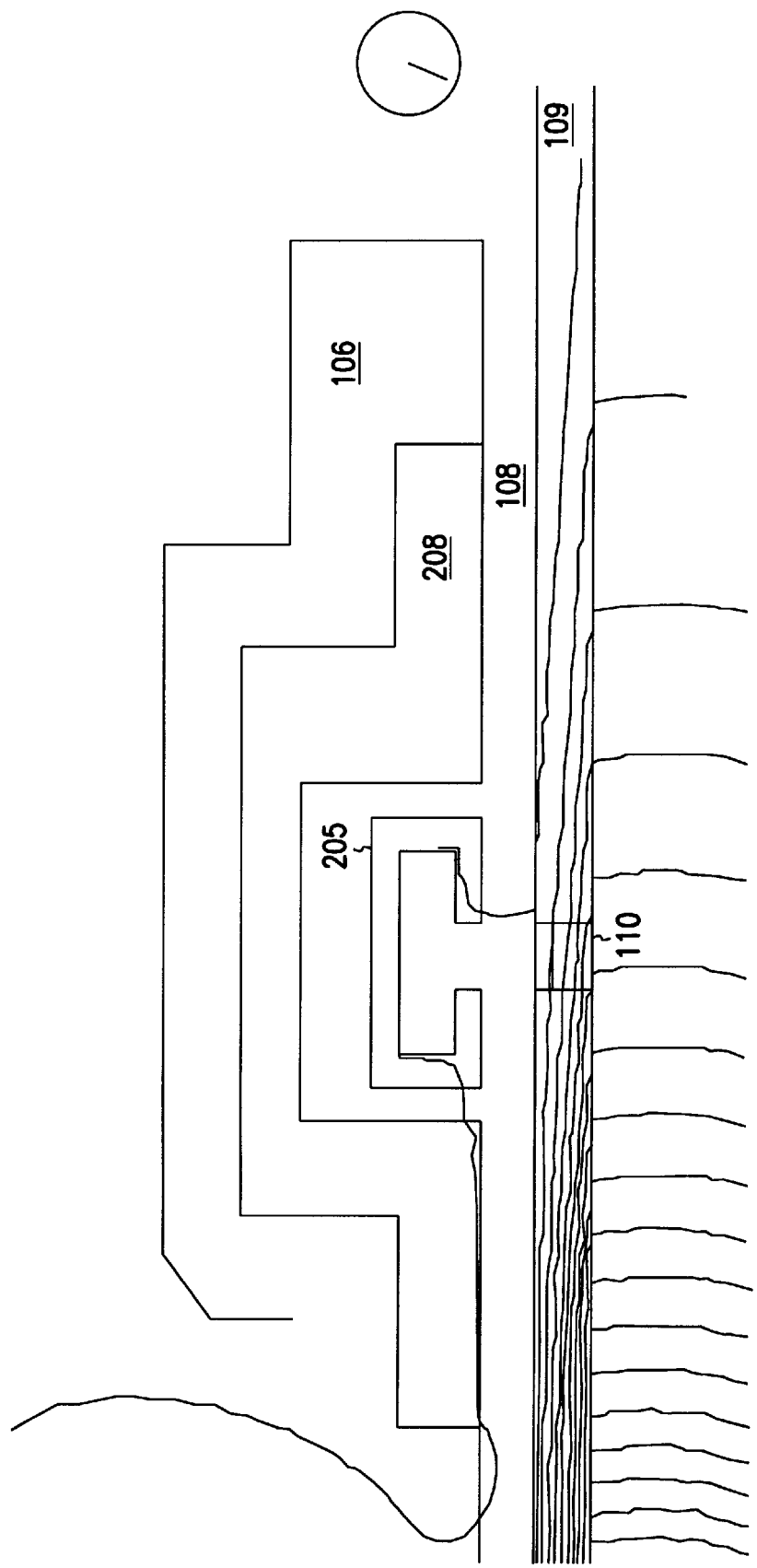

FIG. 37 shows a graph of flux variation in the region of detector 200 for a non-defect case; entitled "PRFEC Probe for Steel Plates Model EZ00"; and annotated:

EQUI-FLUX Magnitude: GAP=8 mm. No Defect 200 mm<X<400 mm–40 mm<Y<80 mm.

Figure 38:
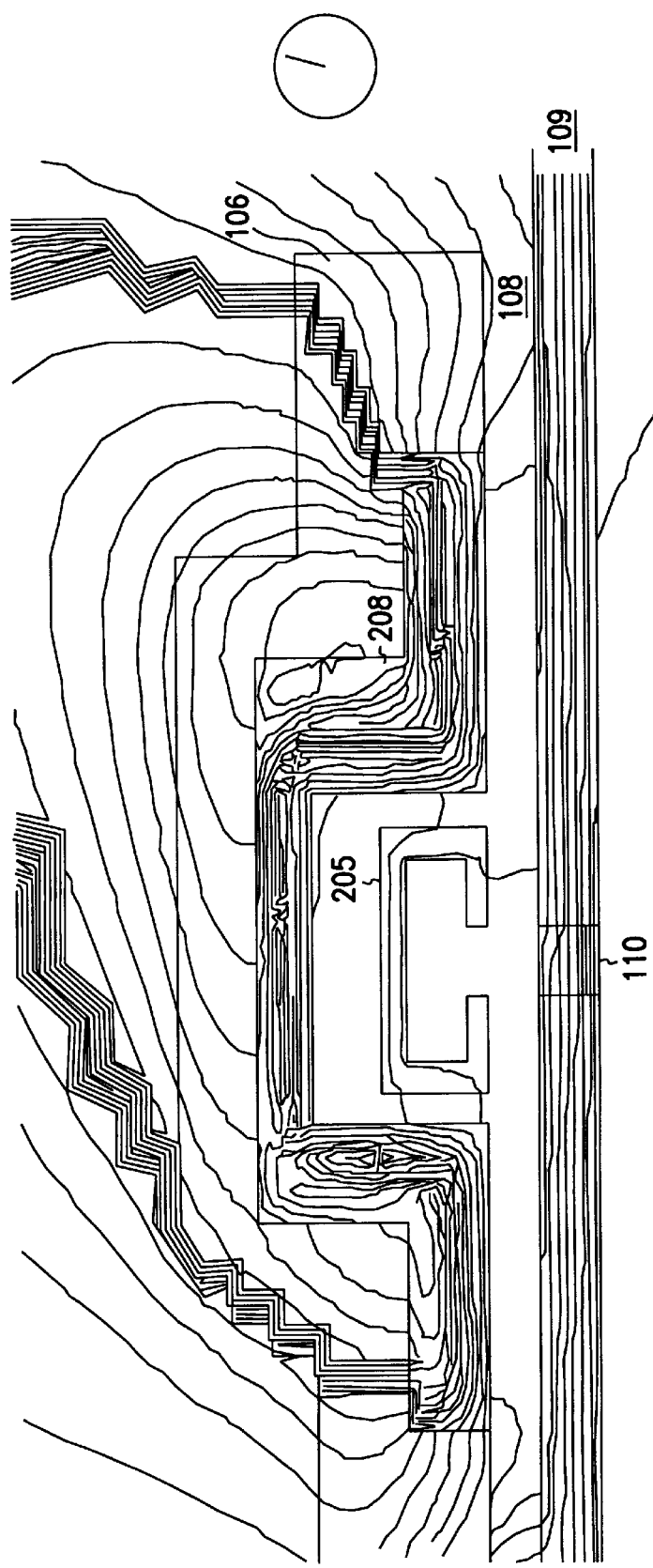

FIG. 38 shows a graph of phase variation in the region of detector 200 for a non-defect case; entitled "PRFEC Probe for Steel Plates Model EZ00"; and annotated:

EQUI-PHASE: GAP=8 mm. No Defect 200 mm<X<400 mm–40 mm<Y<80 mm.

Figure 39:
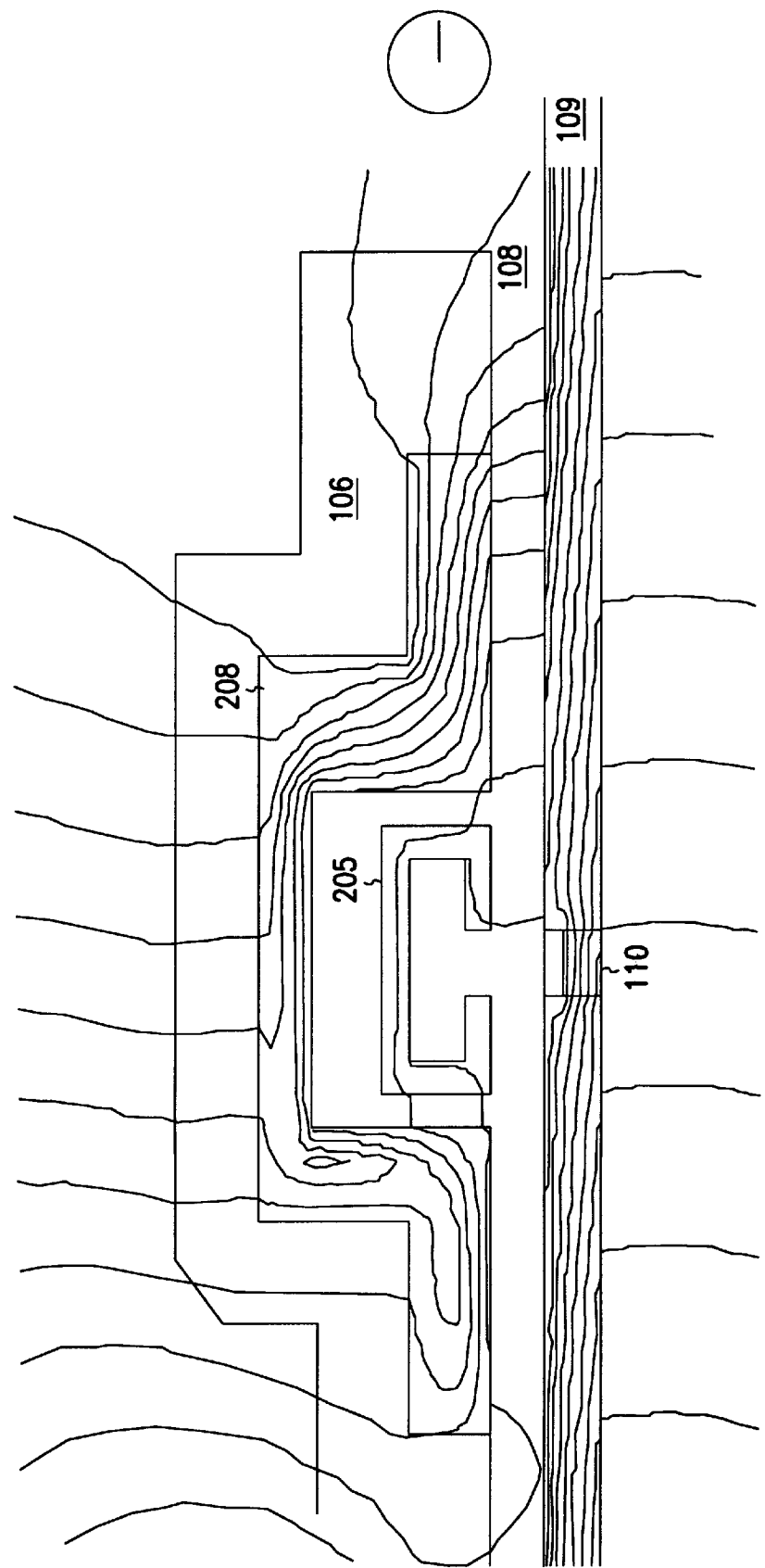

FIG. 39 shows a graph of the natural logarithm of the absolute value of magnitude variation (equi-potentials of ln (|AR|), where A=magnetic vector potential, and R=radius in cylindrical coordinates) in the region of detector 200 for a 40% deep upper-surface-defect; entitled "PRFEC Probe for Steel Plates Model EZ00"; and annotated:

EQUI-LN<1 AR 1>:GAP=8 mm. Defect (40%)

200 mm<X<400 mm–40 mm<Y<80 mm.

Figure 40:
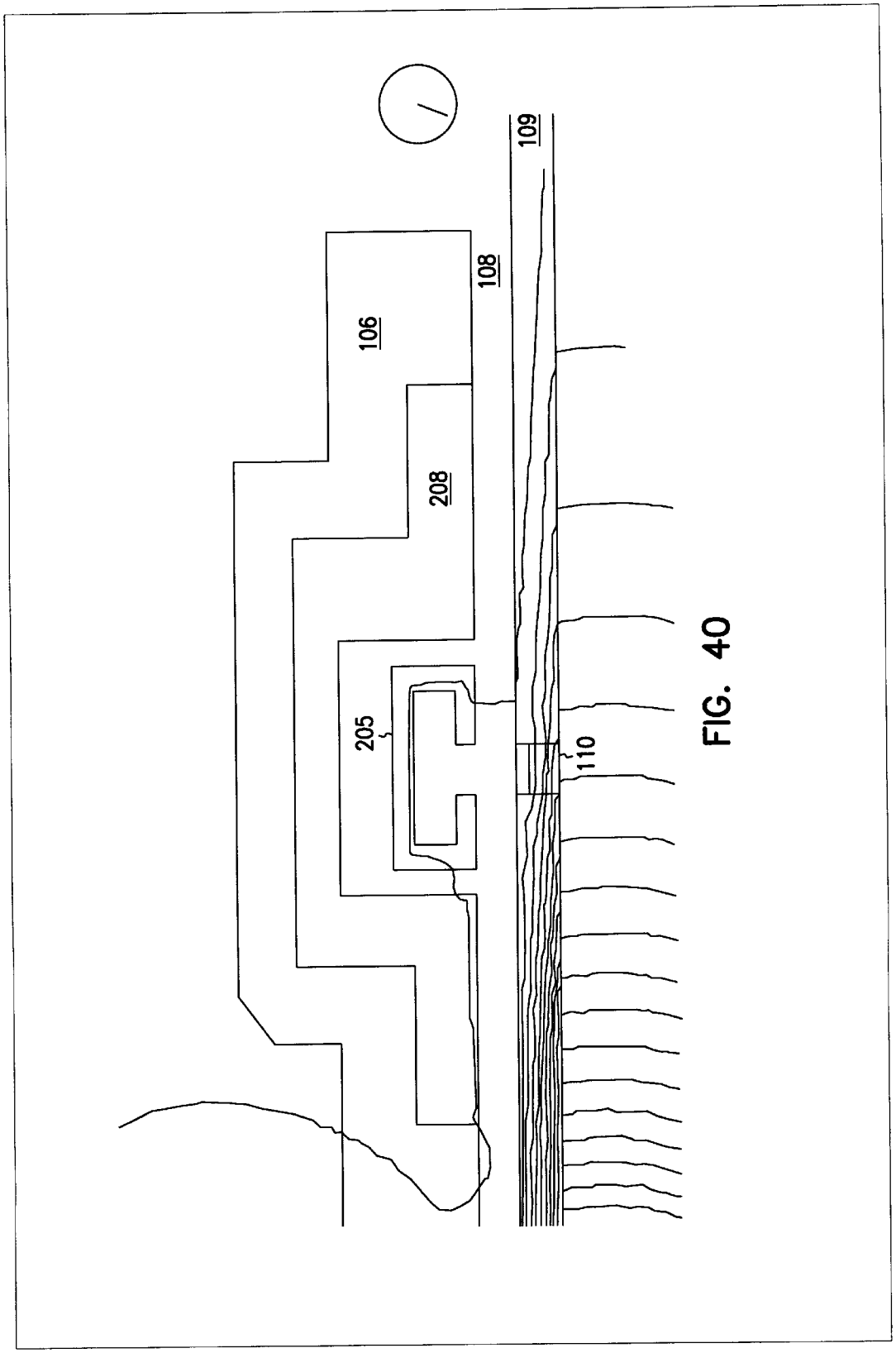

FIG. 40 shows a graph of flux variation in the region of detector 200 for a 40% deep upper-surface-defect case; entitled "PRFEC Probe for Steel Plates Model EZ00"; and annotated:

EQUI-FLUX Magnitude: GAP=8 mm. Defect (40%)

200 mm<X<400 mm–40 mm<Y<80 mm.

Figure 41:
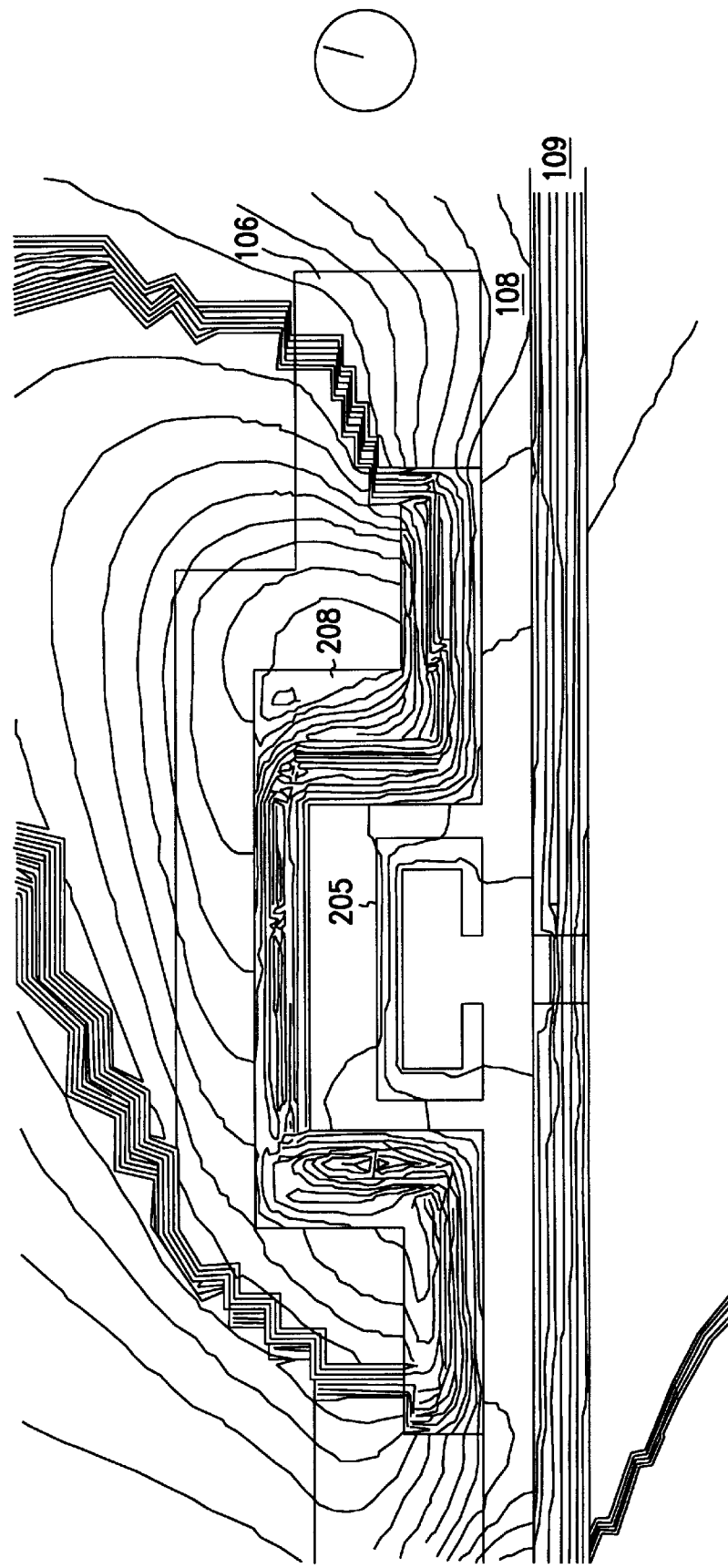

FIG. 41 shows a graph of phase variation in the region of detector 200 for a 40% deep upper-surface-defect case; entitled "PRFEC Probe for Steel Plates Model EZ00"; and annotated:

EQUI-PHASE: GAP=8 mm. Defect (40%)

200 mm<X<400 mm–40 mm<Y<80 mm.

Figure 42:
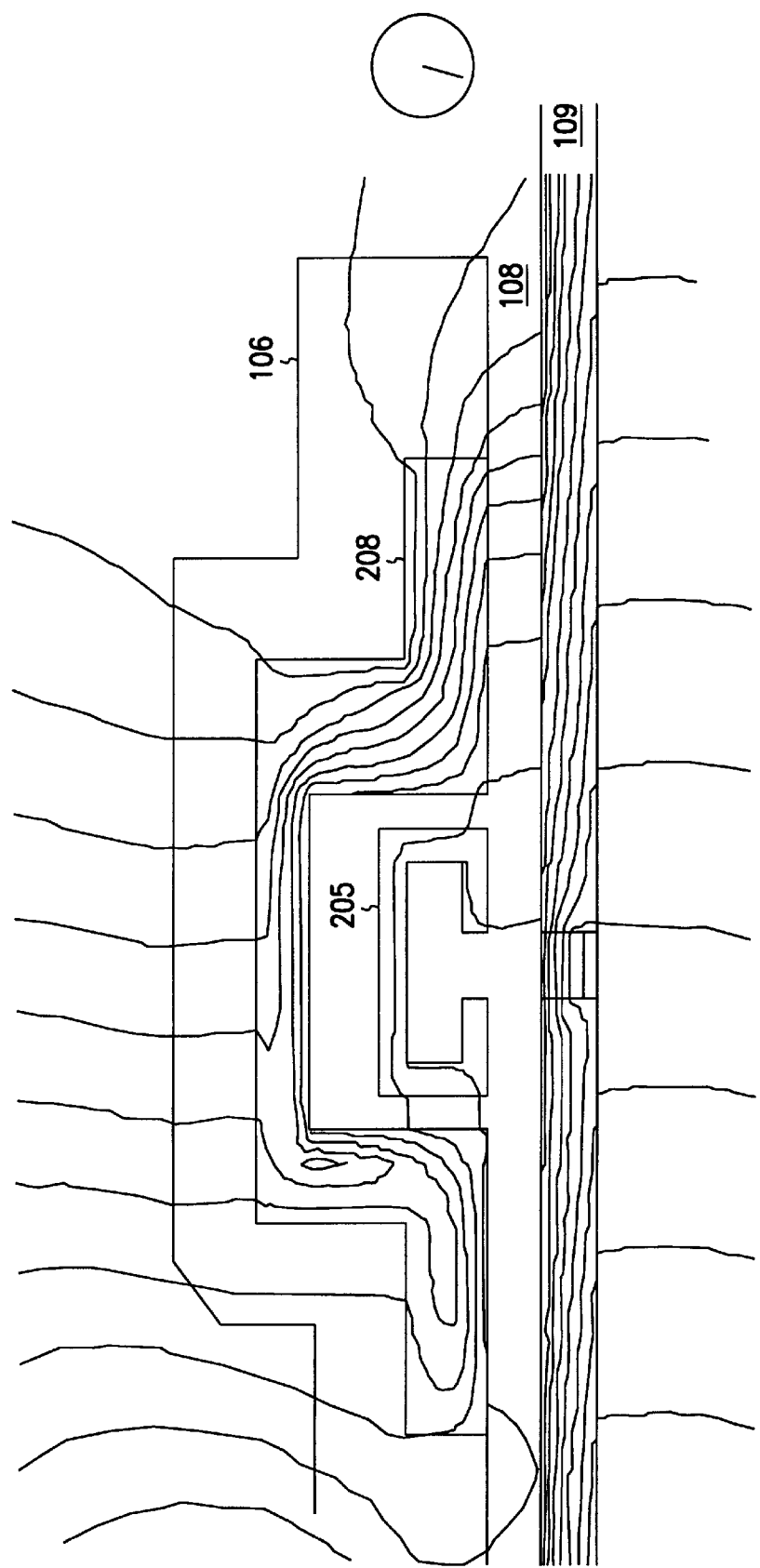

FIG. 42 shows a graph of the natural logarithm of the absolute value of magnitude variation (equi-potentials of ln(|AR|), where A=magnetic vector potential, and R=radius in cylindrical coordinates) in the region of detector 200 for a 40% deep lower-surface-defect; entitled "PRFEC Probe for Steel Plates Model EZ00"; and annotated EQUI-LN<1 AR 1>: GAP=8 mm. Defect (40%) Lower 200 mm<X<400 mm–40 mm<Y<80 mm.

Figure 43:
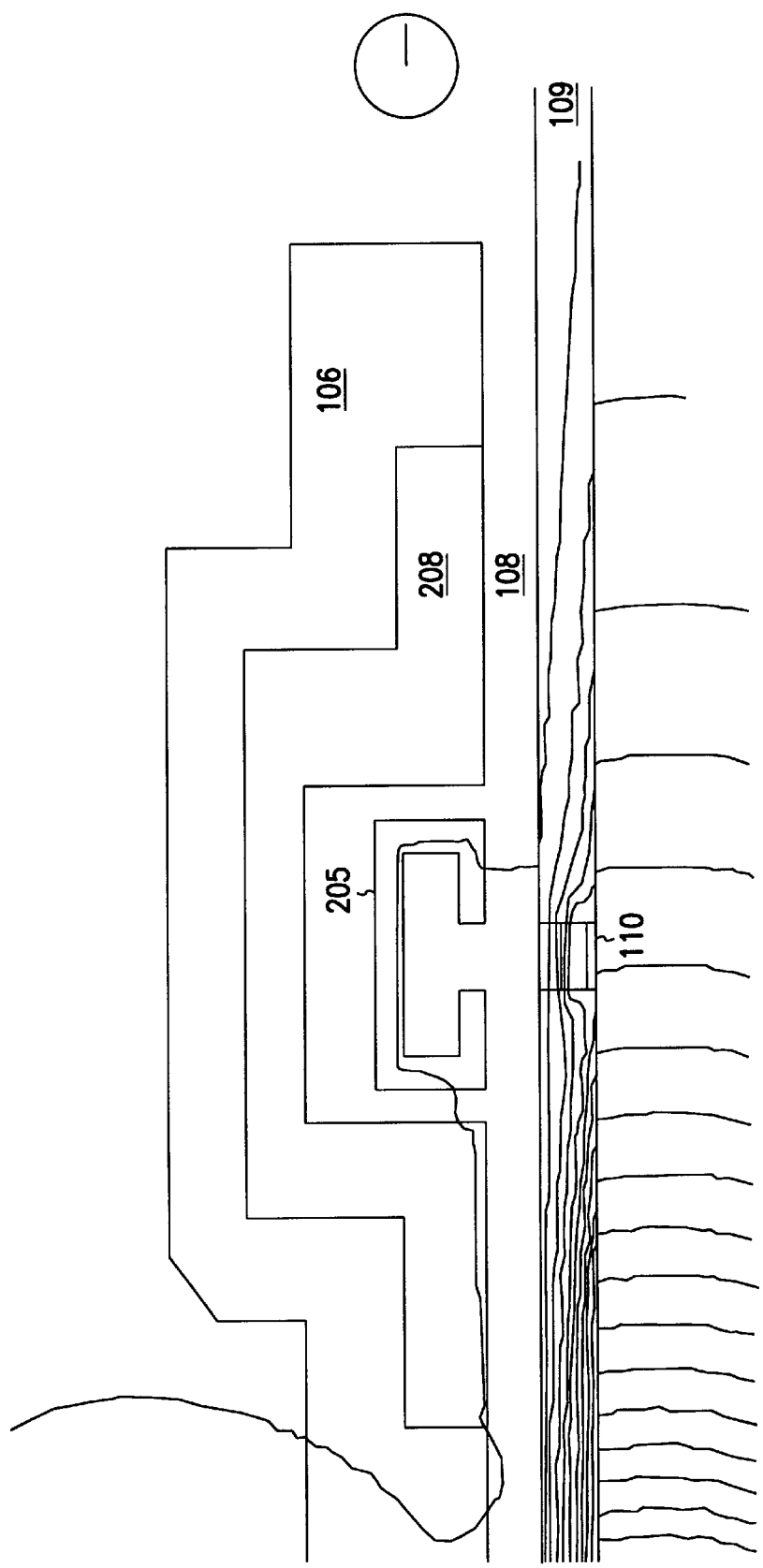

FIG. 43 shows a graph of flux variation in the region of detector 200 for a 40% deep lower-surface-defect case; entitled "PRFEC Probe for Steel Plates Model EZ00"; and annotated:

EQUI-FLUX Magnitude: GAP=8 mm. Defect (40%) Lower 200 mm<X<400 mm–40 mm<Y<80 mm.

Figure 44:
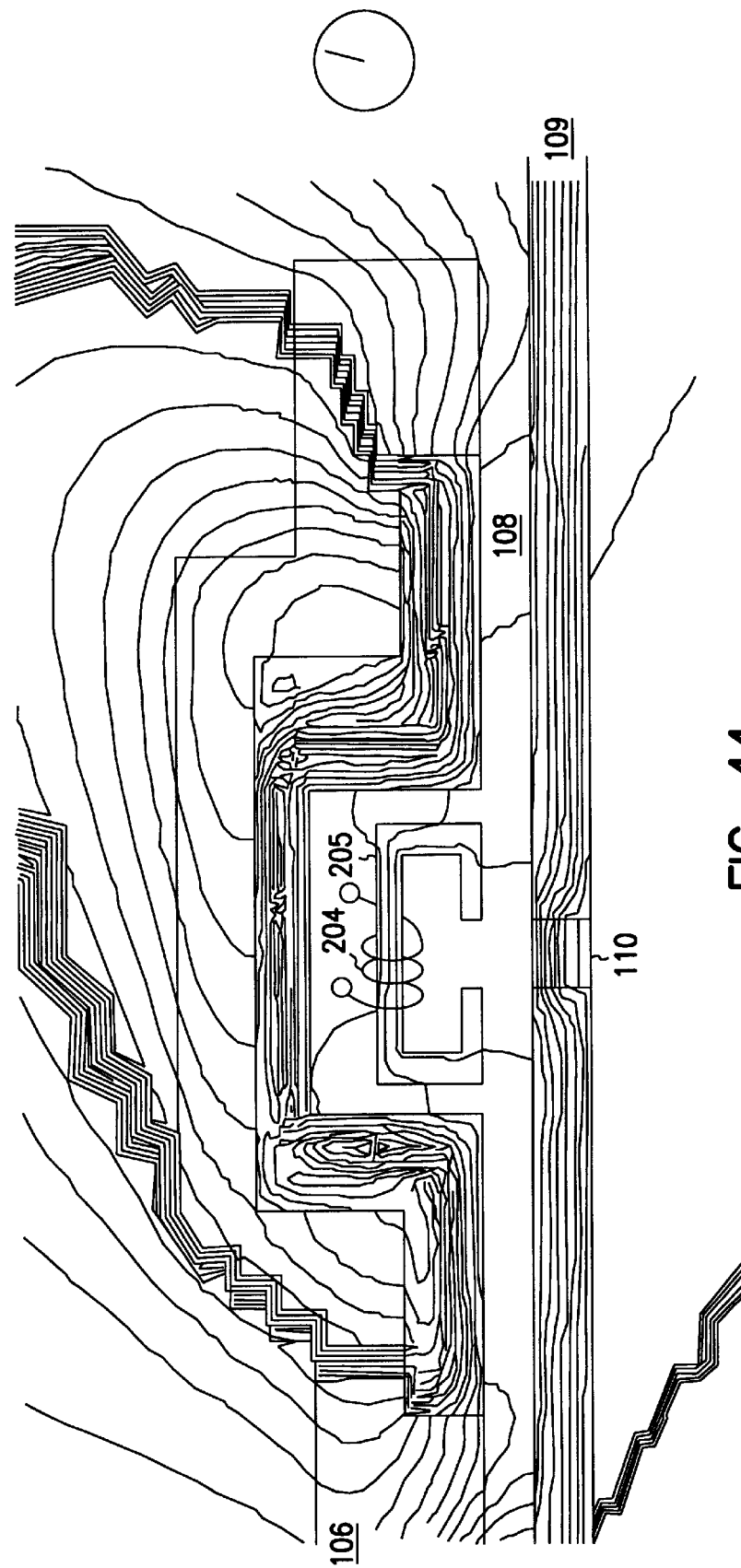

FIG. 44 shows a graph of phase variation in the region of detector 200 for a 40% deep lower-surface-defect case; entitled "PRFEC Probe for Steel Plates Model EZ00"; and annotated:

EQUI-PHASE: GAP=8 mm. Defect (40%) Lower 200 mm<X<400 mm–40 mm<Y<80 mm.

Figure 45:
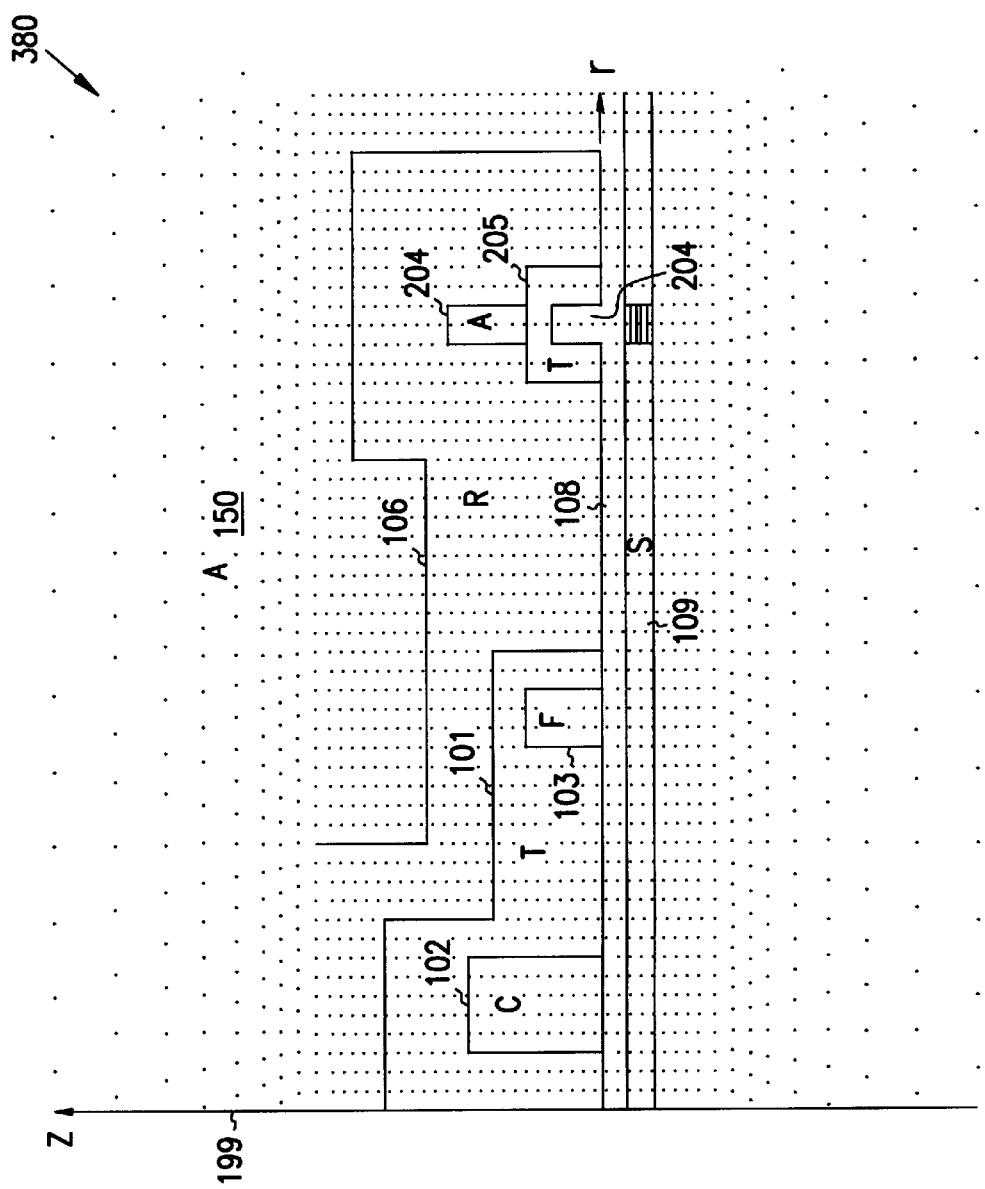

FIG. 45 shows a radial cross section, starting at centerline 199 and extending in a vertical plane, of yet another exemplary PRFEC probe 380 according to the present invention; entitled "EX38 Suggested Sketch for Plane Steel Inspection RFEC Probe Model" and annotated:

Reference Numeral 150=A–Air

Reference Numeral 106=R–Aluminum, σ=3.7×10$^7$s

Reference Numerals 101 and 205=T–Ferrite, $\mu_r$=1,000~10,000

Reference Numeral 109=S–Steel Plate, $\mu_{r0}$≤150

Reference Numeral 102=C–Main Coil, 200~1,000 ampere turns

Reference Numeral 103=F–Auxiliary Coil, 2.5%~6.0% ampere turns of that of coil C and phase-shifted on 10 degrees~30 degrees lag behind.

Figure 46:
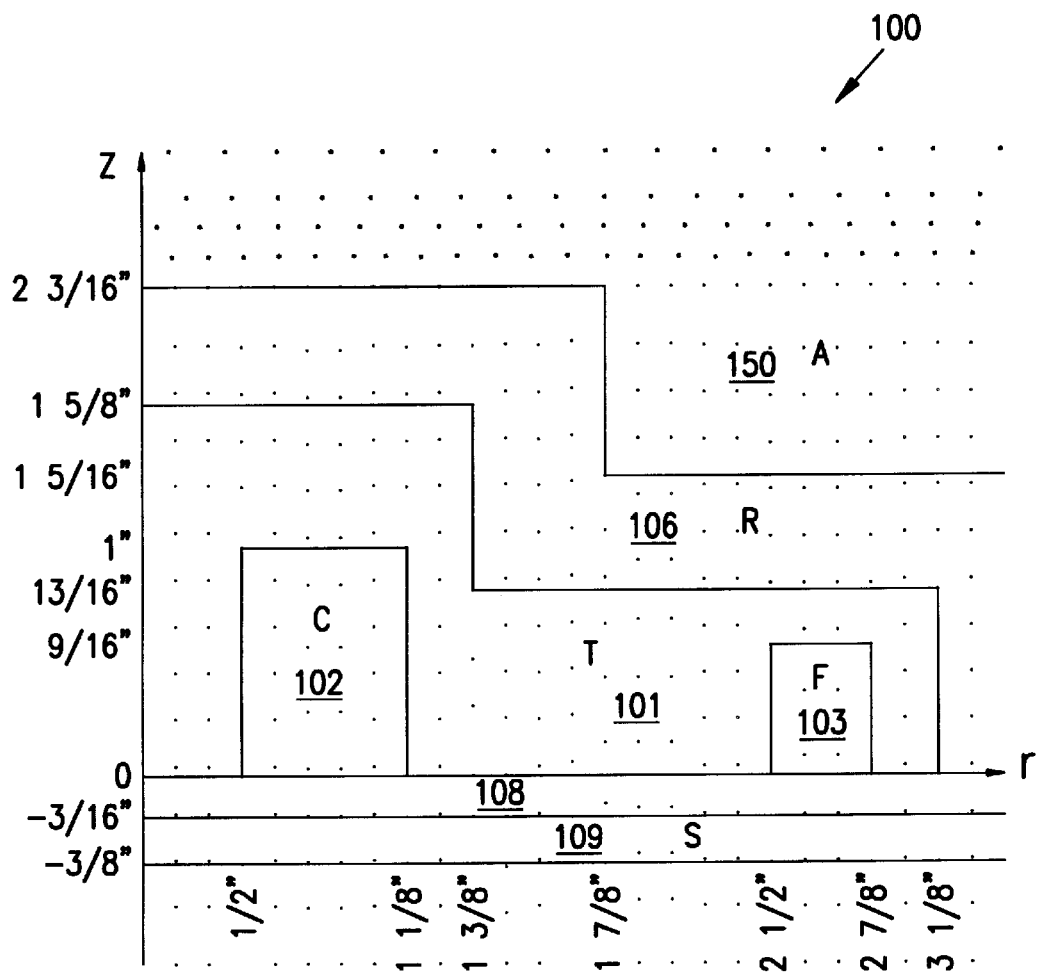

FIG. 46 shows a radial cross section of the excitation part 100 of PRFEC probe 380 as shown in FIG. 45; entitled "EZ38 Suggested Sketch for Plane Steel RFEC Probe: Primary Par t" and annotated:

Reference Numeral 150=A–Air

Reference Numeral 106=R–Aluminum, σ=3.7×10$^7$s

Reference Numerals 101 and 205=T–Ferrite, $\mu_r$=1,000~10,000

Reference Numeral 109=S–Steel Plate, $\mu_{r0}$≤150

Reference Numeral 102=C–Main Coil, 200~1,000 ampere turns

Reference Numeral 103=F–Auxiliary Coil, 2.5%~6.0% ampere turns of that of coil C and Phase-shifted on 10 degrees~30 degrees lag behind.

Figure 47:
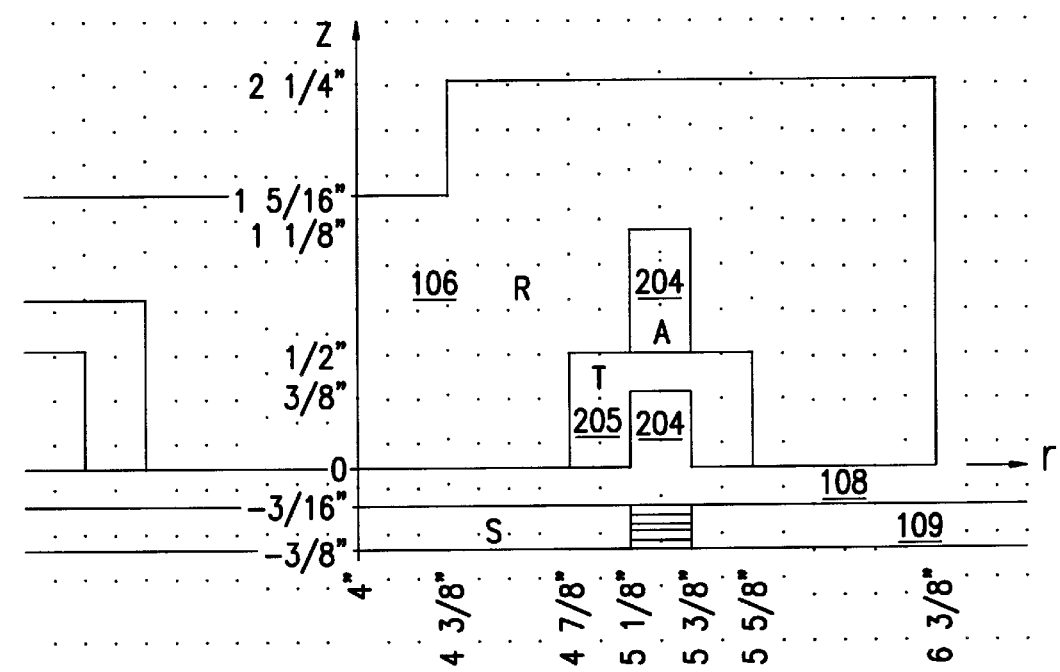

FIG. 47 shows a radial cross section of the pick-up part 200 of PRFEC probe 380 as shown in FIG. 45; entitled "EZ38 Suggested Sketch for Plane Steel RFEC Probe: Secondary Part" and annotated:

Reference Numeral 150=A–Air

Reference Numeral 106=R–Aluminum, σ=3.7×10$^7$s

Reference Numeral 101 and 205=T-Ferrite, $\mu_r$=1,000~10,000

Reference Numeral 108=S-Steel Plate, $\mu_{r0}$≤150

Reference Numeral 102=C-Main Coil, 200~1,000 ampere turns

Reference Numeral 103=F-Auxiliary Coil, 2.5%~6.0% ampere turns of that of coil C and phase-shifted on 10 degrees lag behind.

Figure 48:
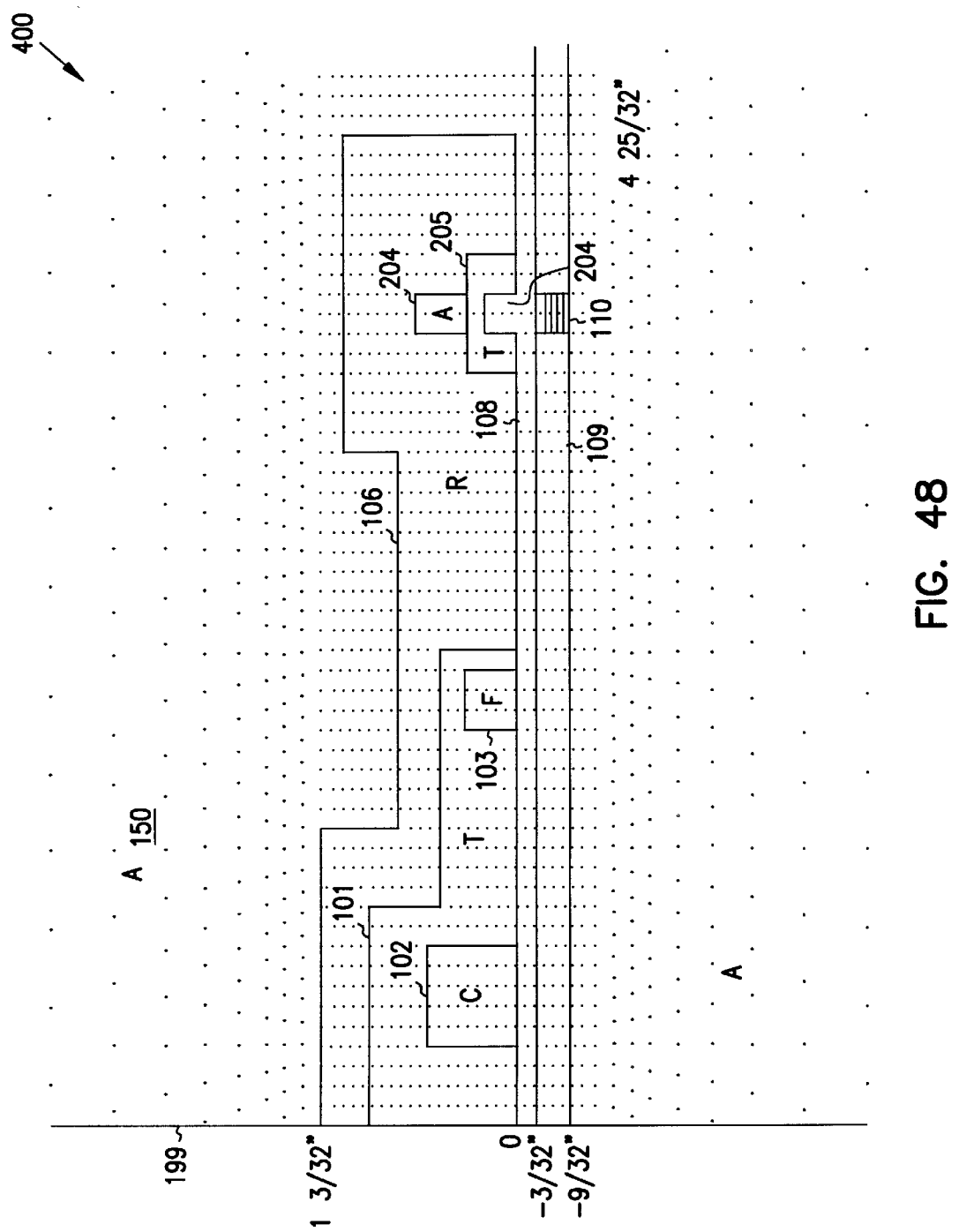

FIG. 48 shows a radial cross section, staring at centerline 199 and extending in a vertical plane, of yet another exemplary PRFEC probe 400 according to the present invention; entitled "EZ40 Scaled From EZ38, Factor for X=0-75, for Y=0-5" and annotated:

Reference Numeral 150=A-Air

Reference Numeral 106=R-Aluminum, σ=3.7×10$^7$s

Reference Numeral 101 and 205=T-Ferrite, $\mu_r$=1,000~10,000

Reference Numeral 109=S-Steel Plate, $\mu_{r0}$≤150

Reference Numeral 102=C-Main Coil, 100~500 ampere turns

Reference Numeral 103=F-Auxiliary Coil, 2.5%~6.0% ampere turns of that of coil C and phase-shifted on 10 degrees~30 degrees lag behind.

Figure 49:
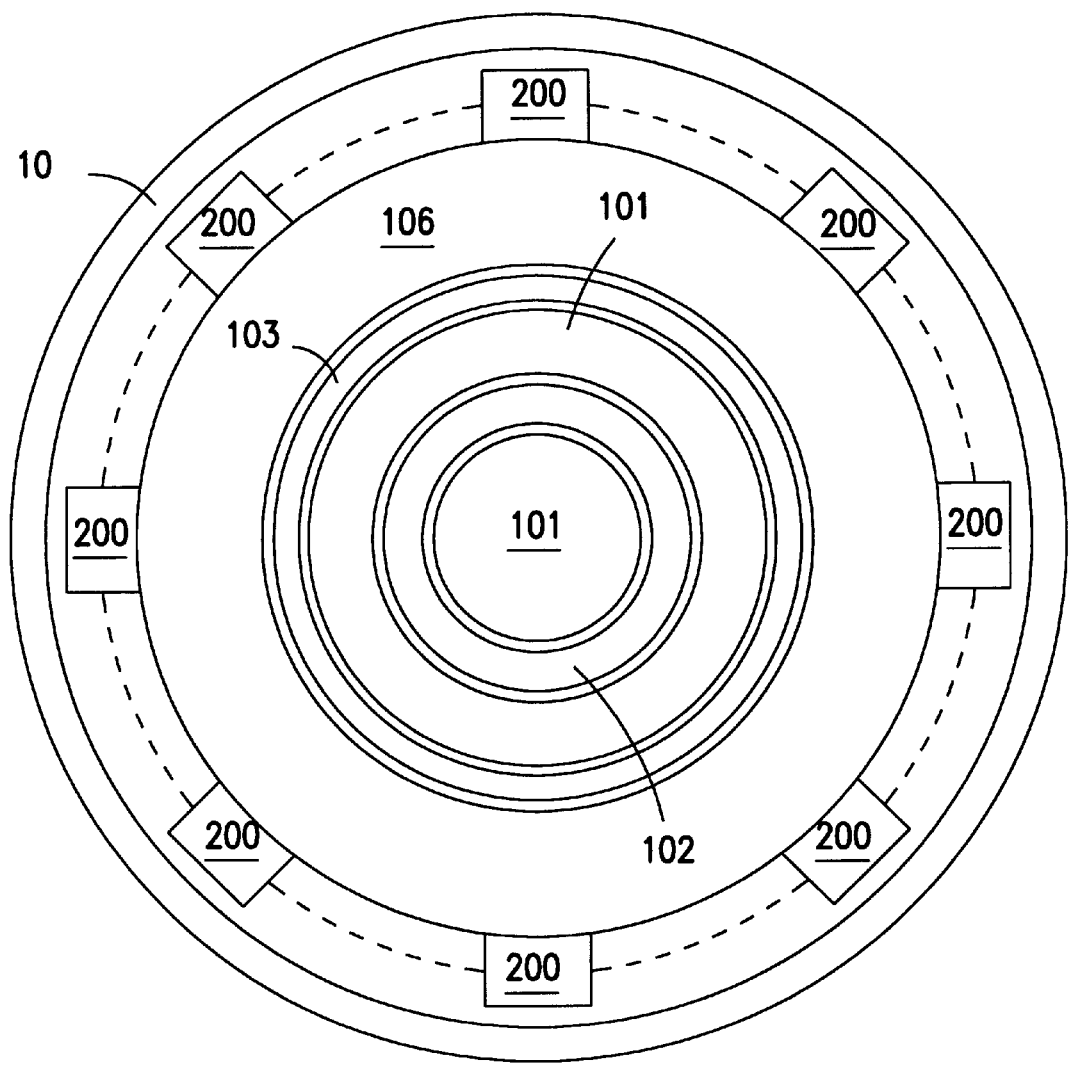

FIG. 49 shows a bottom view of PRFEC probe 380 as shown in FIG. 45 showing one embodiment of the positioning of multiple detectors 200 (eight in this case); entitled "Suggested Allocation for Detectors".

Figure 50:
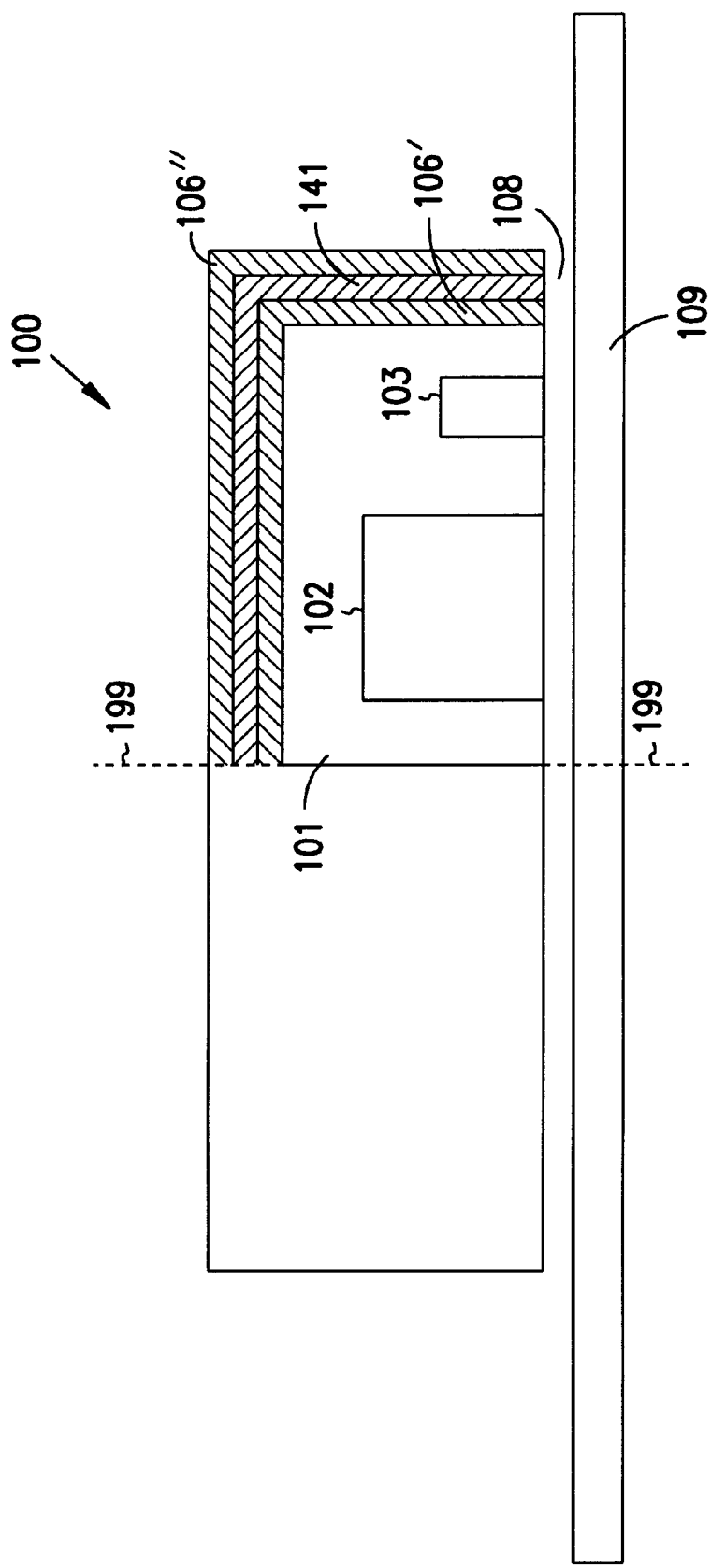

FIG. 50 shows an alternative shield arrangement for the excitation unit, the shield having alternating laminated layers of aluminum 106' and 106" and steel 141.

Figure 51:
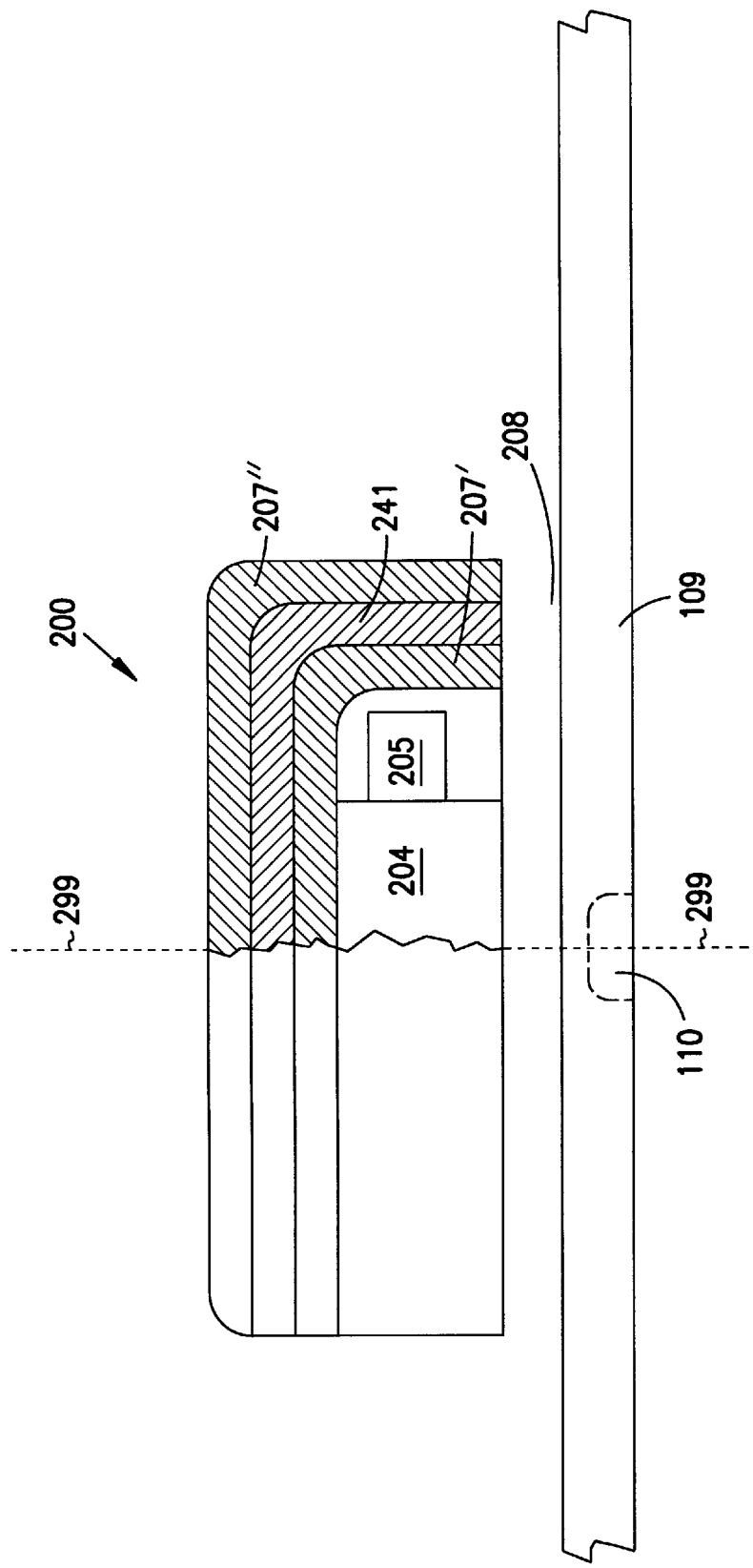

FIG. 51 shows an alternative shield arrangement for the receiver unit, the shield having alternating laminated layers of aluminum 207' and 207' and steel 241.

Figure 52:
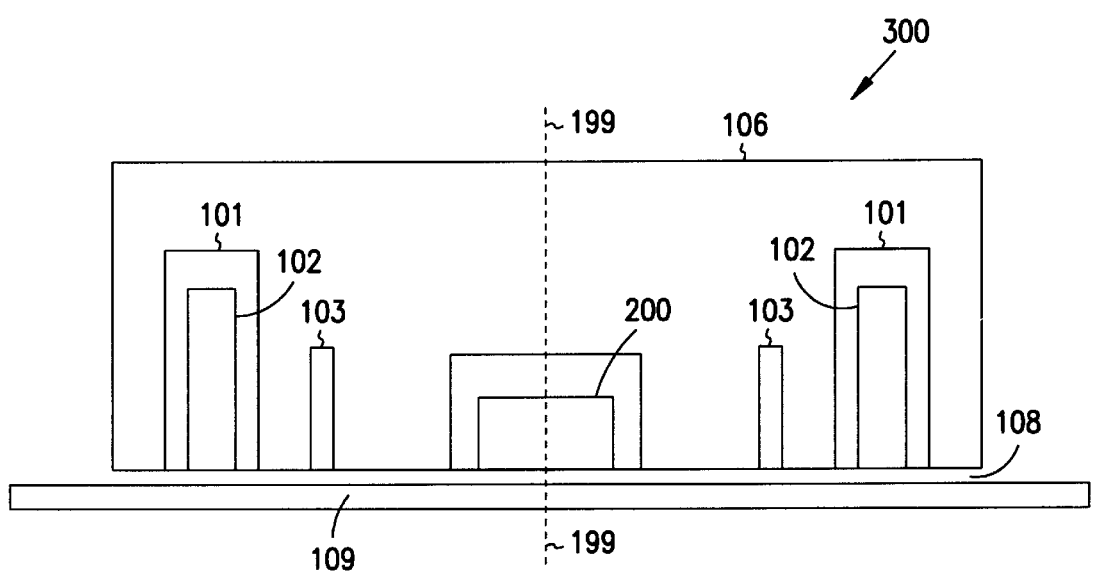

FIG. 52 shows a cross-section schematic showing an embodiment of the invention with the receiver unit placed at the center of the probe, while the primary coil 102 and its core 101 are placed close to the outer-most wall of the probe, and the auxiliary coil 103 is between surrounded by shield 106.

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is to be understood that other embodiments may be utilized and structural changes may be made without departing from the scope of the present invention.

Figure 1:
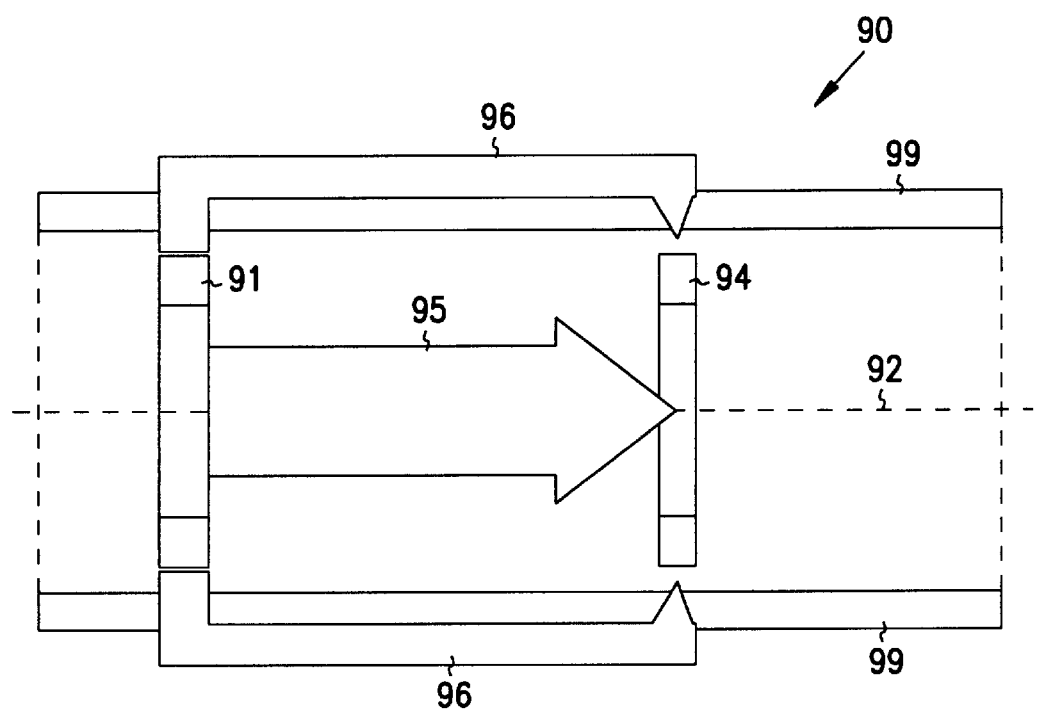
FIG. 1 is a schematic of a prior-art RFEC system for detecting flaws in a metal tube.
Figure 2:
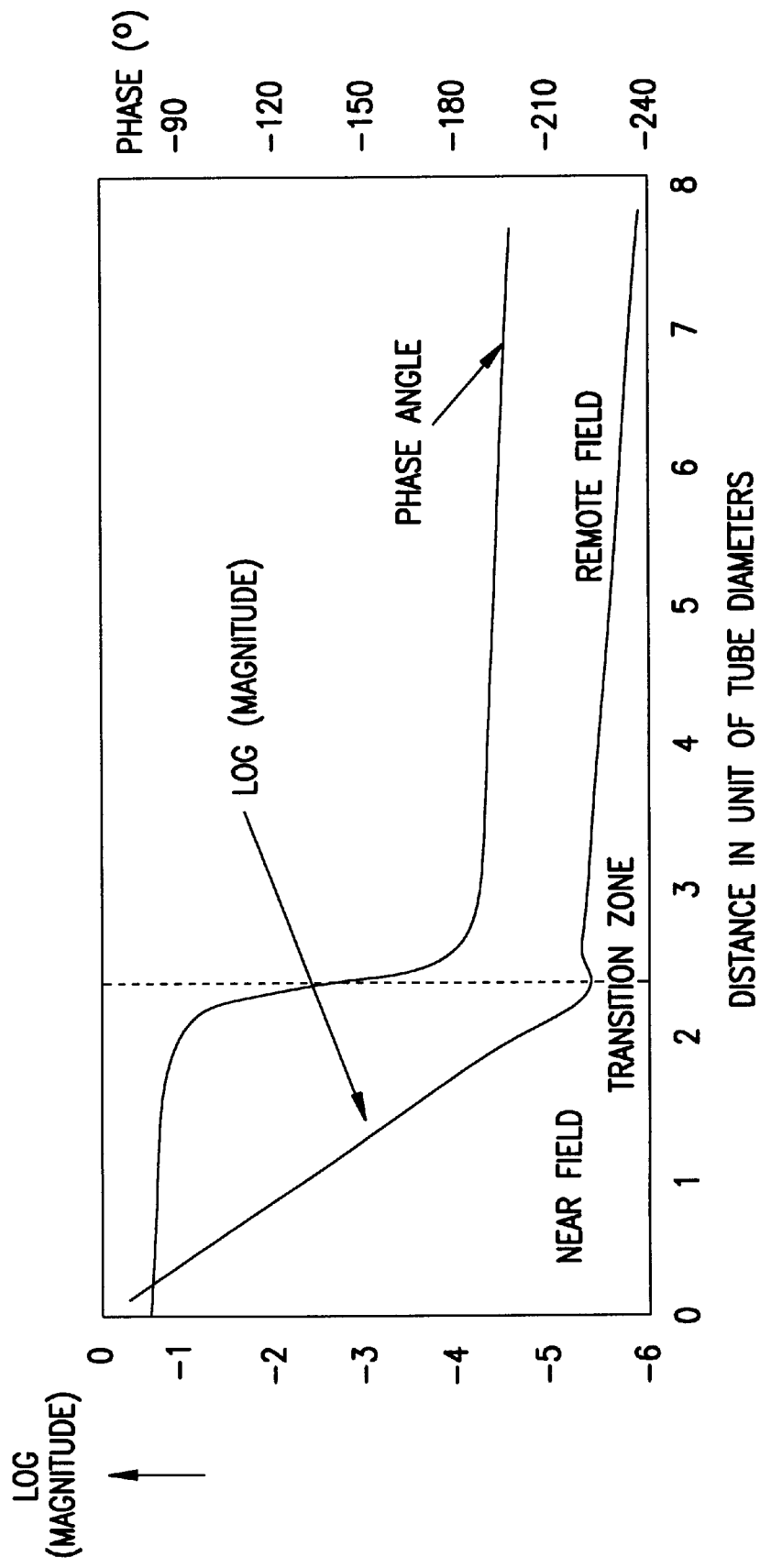
FIG. 2 is a representative plot of magnitude and phase for the system of FIG. 1.

Referring to FIG. 2, the exponential attenuation of signal magnitude in the near-field region may be explained by the existence of the induced eddy current inside the tube wall. It plays a role of restricting the electromagnetic flux from expanding axially. The -90° constant phase in the near-field region is explained by Faraday's law. In quasi-static case the induced voltage in the pick-up coil is $e=-\partial\Psi/\partial t=-j\omega LI$, which is 90° lag to the excitation current I (In FIG. 2, the near-field region starts at the excitation coil and extends to approximately 2.4 tube diameters; a transition zone extends from about 1.9 to about 2.6 tube diameters; and a remote-field region extends in the area beyond approximately 2.4 tube diameters.)

However, the question of how the phase difference between signals of the remote-field region and near-field region can be related to the tube wall conditions was unanswered. T. R. Schmidt proposed a hypothesis of "double transit eddy current through the walls" (see T. R. Schmidt "The Remote Field Eddy Current Inspection Technique," *Materials Inspection*, 42, pp 225-230, February 1984) based on his extensive experimental data for one explanation of the phenomenon. Then, the Finite Element Modeling (FEM) of the RFEC phenomena (see Lord, W., "Final Report on Finite Element Modeling of the Remote Field Eddy Current Effect", *American Gas Association Project PR* 179-520, Department of Electrical Engineering, Colorado State University, September 1986, Lord, W., Sun, Y. S., Udpa, S. S., and Nath, S., "A Finite Element Study of the Remote Field Eddy Current Phenomenon," IEEE Trans. on Magnetics, Vol. 24, No. 1, pp. 435-438, January 1988, and Sun, Y.-S., "Finite Element Study of Diffusion Energy Flow in Low-Frequency Eddy Current Fields," *Materials Evaluation*, 47, pp. 87-92, January 1989.) revealed an answer to much of the mystery. FEM shows that the energy released from the excitation coil travels twice through the tube wall, from inside to outside in the near field, and from outside to the inside in the remote field.

The concept of double energy flow transmission through a tube wall has been verified and utilized in our later work on visualizing the RFEC phenomena (see Sun, Y. S., Si, J. T., et., "Computer Animated Presentation Visualizing the Phenomena in Remote Field Eddy Current Non-destructive Testing," *Electromagnetic Force and Applications—Elsevier Studies in Applied Electromagnetics in Materials*, edited by J. Tani and T. Takagi, pp. 203—206, 1992.), physics on, RFEC responses to axially aligned cracks (see Sun, Y. S., Lin, H. Y., Chen, M. J., et., "Finite Element Modeling and Physics of Remote Field Eddy Current Responses for Axially Aligned Cracks," *IEEE Trans. on Magnetics*, Vol. 28, No. 4, pp. 1941-1947, July 1992.), RFEC probe structure improvement (see Sun, Y. S., Qu, M. X, Si, J. T., et., "Improvement in Remote-Field Eddy Current Probe Structure," *Materials Evaluation*, 50, pp. 600-604+ p. 611, May 1992.), extending the RFEC technique to pulsed excitation (see Chen, M., Sun, Y., Lord, W. and Shin, Y. K., "Pulsed RFEC Response," *IEEE Trans. on Magnetics*, Vol. 28, No. 2, pp. 1930-1933, March 1992.) and magnetic flux leakage probe with motion (see Sun, Y. S., Lord, W., Katragadda, G., "Motion Induced Remote Field Eddy Current Effect," *IEEE Trans. on Magnetics*, Vol. 28, No. 4, pp. 1941-1947, July 1992.).

According to the above mentioned rule, in order to build a RFEC probe for metallic plate inspection, one key design feature is to ensure that the energy flow passes through the plate wall twice.

In the tubing case, the induced eddy current inside the tube wall plays a role of restricting the flux from its expanding axially; this results in the rapid attenuation of the direct-coupling field (i.e., the field which directly couples the excitation coil to the pick-up coil). A large direct-coupling field will result in the pick-up coil being overwhelmed with the directly coupled field and thus unable to detect field signals which result from defects in the tubing. The rapid attenuation of the direct-coupling field caused by the induced eddy current provides a mechanism for the electromagnetic energy to penetrate from tube exterior back to its interior at the remote-field region. There is no such mechanism for metallic plates. To accomplish having the energy passing twice through the wall in a flat metal case, the followanmg measures are applied in designing and fabricating the probe:

(a). Providing a specially designed magnetic circuit consisting of a pot-core, and two excitation coils: a primary coil and an auxiliary coil;

(b). Providing a magnetic circuit to each one of one or more pick-up coils.

(c). Providing shielding for the two excitation coils and the pick-up coils in order to minimize any direct coupling between the excitation coils and the pick-up coil. In one embodiment, this shielding is provided by one or more highly-conducting shields which substantially cover the excitation core and its two excitation coils on all sides except for the face adjacent to the plate being tested.

Figure 3:
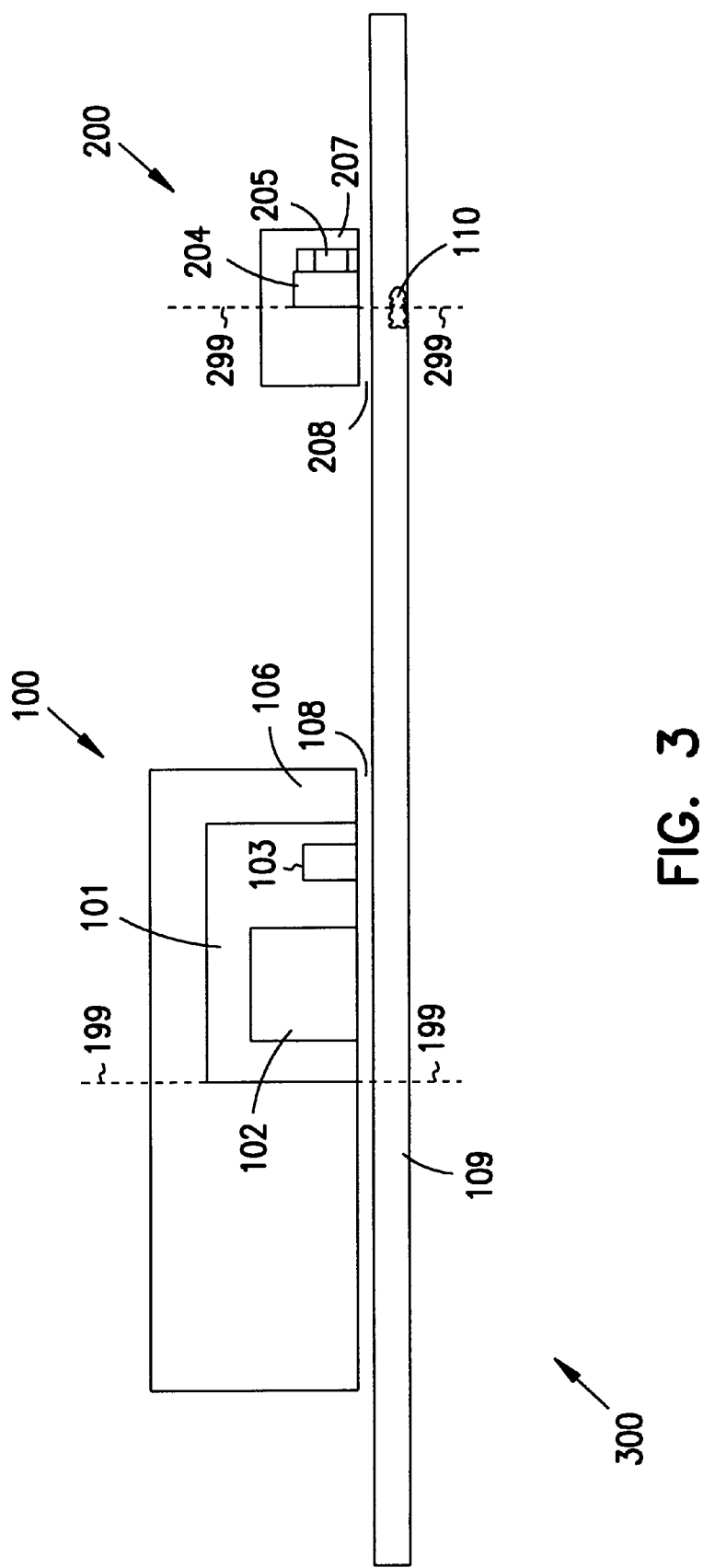
FIG. 3 is a schematic of a PRFEC system 300 comprising excitation unit 100 and receiver unit 200, each shown in partial-cutaway cross section

FIG. 3 shows one embodiment of such a generalized probe 300 comprising excitation unit 100 and receiver unit 200, each shown in partial-cutaway cross section. The right half partial cutaway view of excitation unit 100 shows a vertical section (which can be rotated 360 degrees around center line 199) of excitation probe 100, and one-half of a vertical section of receiver unit 200 (which could be, for example, any one of FIGS. 7A through 7F, or a superconducting quantum interference device(SQUID), or a magnetoresistive device, or any other suitable magnetic-signal detector). It is to be understood that the design and the shape of the probe can vary dramatically in order to fit the shape and size of the target plates, and can vary in order to match the instruments and the inspecting system, as long as the enabling and the operational principles taught by this invention are followed.

A. The Magnetic Core 101 for the Excitation Coils 102 and 103

The pot-core 101 for excitation coils works as a magnetic circuit for both the primary coil 102 and the auxiliary coil 103. It is one of the critical probe parts in realizing the energy double-transmission through the plate under inspection 109. The core 101 is made of high permeability and low-conducting or non-conducting material(s). It can be characterized by the following features (see the example shown in FIG. 4):

The core 101 provides a substantially closed magnetic circuit. The core 101 and its magnetic circuit can be of any shape having an opening which faces air-gap 108 (called the "sensing face") towards the plate under inspection 109 and a highly conducting shield 106 (made from, for example, aluminum) which covers substantially all of the rest of the excitation core 101.

In one embodiment shown in FIG. 3, the excitation unit shield 106 is made of one layer of solid aluminum. In another embodiment shown in FIG. 50, used in order to enhance the shielding function, the excitation unit shield is made of a laminated structure having two layers of highly conductive material 106' and 106", such as aluminum, laminated on both sides of a ferromagnetic material 141, such as steel. In other embodiments, other numbers of highly conducting layers (such as aluminum) and ferromagnetic layers (such as steel) are used in alternating laminated layers to build the shield for the excitation unit.

The core 101 can be made of a whole piece of a ferromagnetic material, e.g., ferrite, or can be made of two or more pieces of ferromagnetic material(s) with tightly fitting and large connecting area(s) (for example see joint 117 in FIG. 5) in order to minimize reluctance between them. The ferromagnetic material(s) used for making the core 101 can be non-conducting, or can be joined pieces of conducting material(s) with insulation at the joints (e.g., see joint 118 in FIG. 6) in order to minimize possible eddy currents induced in it or them.

Figure 4A:
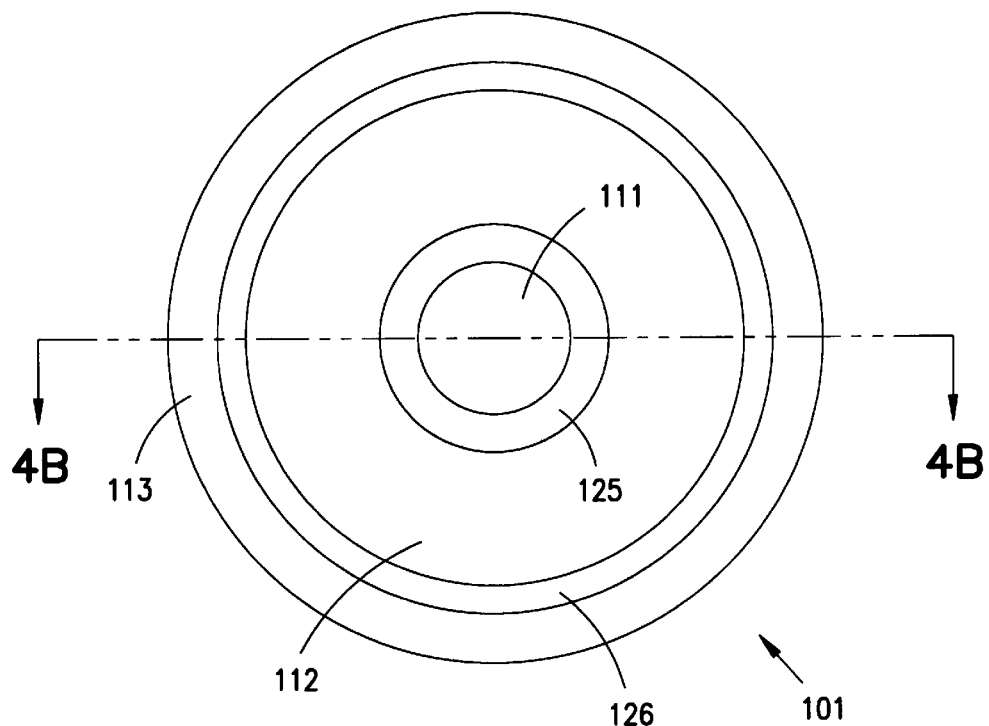
FIG. 4A is a bottom-view schematic of a representative pot-core 101.
Figure 4B:
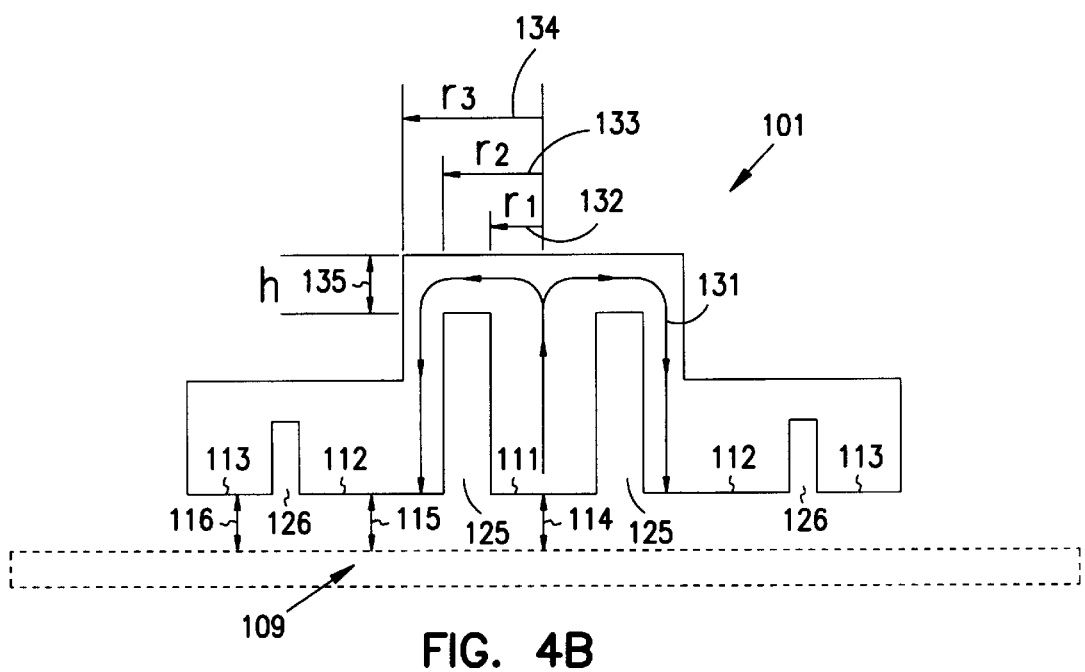
FIG. 4B is a side view along section 4B schematic of a representative pot-core 101 as shown in FIG. 4A.

FIGS. 4A and 4B are a bottom-view schematic of a representative pot-core 101 and a side view along section 4B, respectively, of one embodiment of excitation core 101. Slot 125 houses primary coil 102, and slot 126 houses auxiliary coil 103. Radius $r_1$ 132 is the radius of area 111 (i.e., from the centerline to the inner surface of slot 125), radius $r_2$ 133 is the innermost radius of area 112 (i.e., from the centerline to the outermost surface of slot 125), radius $r_3$ 134 is the radius of the raised portion (i.e., from the centerline to the outer surface of the raised portion of excitation core 101 which is above and outside slot 125), and height h 135 is the distance from the top of slot 125 to the top of excitation core 101.

To avoid magnetic saturation of all those portions of the magnetic circuit, except for its central path, the central path cross section of area $A_1$ 111 in FIGS. 4A and 4B should be smaller than any other cross-section area of the magnetic circuit along and perpendicular to the flux path 131 (e.g., smaller than cylindrical area $A_4=2\pi(r_1 h)=2\pi$(radius $r_1$ 132× height h 135) which is the smallest vertical area above slot 125, and smaller than area $A_5=\pi((r_3)^2-(r_2)^2)=\pi$((radius $r_3$ 134)$^2$-(radius $r_2$ 133)$^2$), which is the smallest horizontal area outside slot 125).

The three air-gaps, gap $\delta_1$ 114, gap $\delta_2$ 115 and gap $\delta_3$ 116 (see FIGS. 4A and 4B) can be of the same value or of different values, but the following relation should be followed:

$$\delta_1/A_1 >> \delta_2/A_2,$$

wherein the minimum ratio of $(\delta_1/A_1)/(\delta_2/A_2)$ is around 10 to 20.

In order to obtain the minimum ratio in a probe design for some practical applications, special measures can taken to minimize $\delta_2$ for a limited $A_2$ and given $\delta_1/A_1$. One typical example of such measures is to attach a flexible (e.g., spring-loaded) ferromagnetic part to the surface $A_2$; such a part may be also attached to surface $A_3$. The ferromagnetic part can be: (a.) steel bristles, (b.) steel rollers, (c.) steel fingers, or (d.) any other similar structures.

B. Currents in Excitation Coils

A low frequency, e.g., in the range of approximately 10 Hz–150 Hz for carbon-steel plates or up to approximately 20,000 Hz for non-ferro plates, AC current is applied to the primary excitation coil to establish the electromagnetic field around the metallic plate. The frequency is generally determined by:

f=c/($\sigma\mu\tau^2$), where σ is the conductivity of the plate, [s/m],

μ is its permeability, [T.m/A],

σ is its thickness, [m], and c=0.03–3.0 depending on which component of the signal, magnitude or phase, is more critical for inspection. A lower value of c is used for obtaining higher signal magnitude; a higher value is used for obtaining higher phase sensitivity. In those cases when the air-gap $\delta_2$ can be designed to be very small, no current in auxiliary coil is needed (or the auxiliary coil can be eliamninated). The primary coil alone is enough for generating the PRFEC effect, and the signal sensed by the pickup coil(s) in the remote region represents the plate wall conditions. When the air-gap $\delta_2$ is big, a proper value of auxiliary current is necessary. However, a properly chosen auxiliary current does not interfere with the plate measurement even when $\delta_2$ changes to or is designed to have a small value.

In one embodiment, the proper current values, i.e., the magnitude and phase of the AC current to one or both excitation coils, which vary as a function of steel properties, wall thickness and the $\delta_2$ value, are obtained experimentally. To determine these values, a test is performed: a thick plate (i.e., one thicker then the plate under inspection) is placed right beneath a piece of the plate sample (i.e., the sample is a piece of steel having similar properties as the plate to be inspected). A maximal value of $\delta_2$ expected in the real inspection should be used in the test. First, a certain driving AC current, having a magnitude and phase designated as $I_p\angle\theta_p$, and having the test frequency is applied to the primary coil. The resultant pick-up probe signal, having voltage magnitude and phase designated $V_{pt}\angle\theta_{pt}$ (for "primary test"), received by the pickup coil or one of the pickup coils is then recorded (in which the phase difference between the driving signal and the pick-up probe signal is recorded). Then, apply the same current to the auxiliaray coil and record the pickup coil signal, $V_{at}\angle\theta_{at}$ (for "auxiliary test") again. The proper values of the auxiliary current magnitude and phase $I_a\angle\theta_a$ will be:

magnitude $I_a=I_p V_{pt}/V_{at}$, phase $\theta_a=\theta_{at}+180°-\theta_{pt}+\theta_p$.

Figure 5:
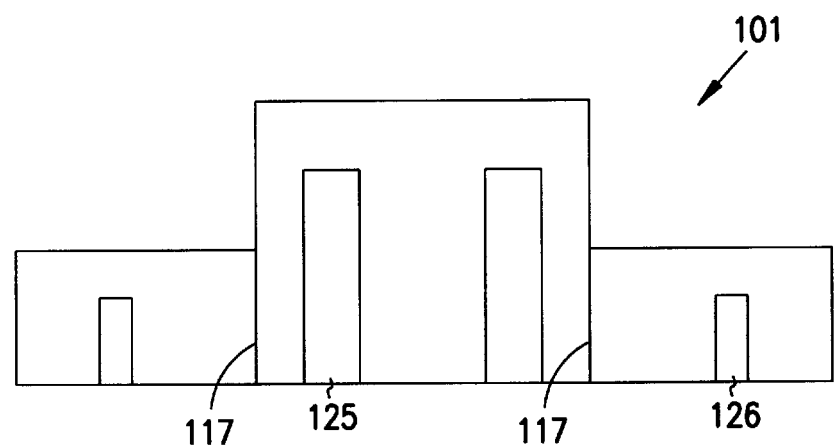
FIG. 5 is a side view along section 4B schematic of a representative pot-core 101 as shown in FIG. 4A, but showing optional connecting joint 117.

FIG. 5 is a side view along section 4B schematic of a representative pot-core 101 as shown in FIG. 4A, but showing optional connecting joint 117 between two pieces of separately fabricated ferromagnetic material.

Figure 6:
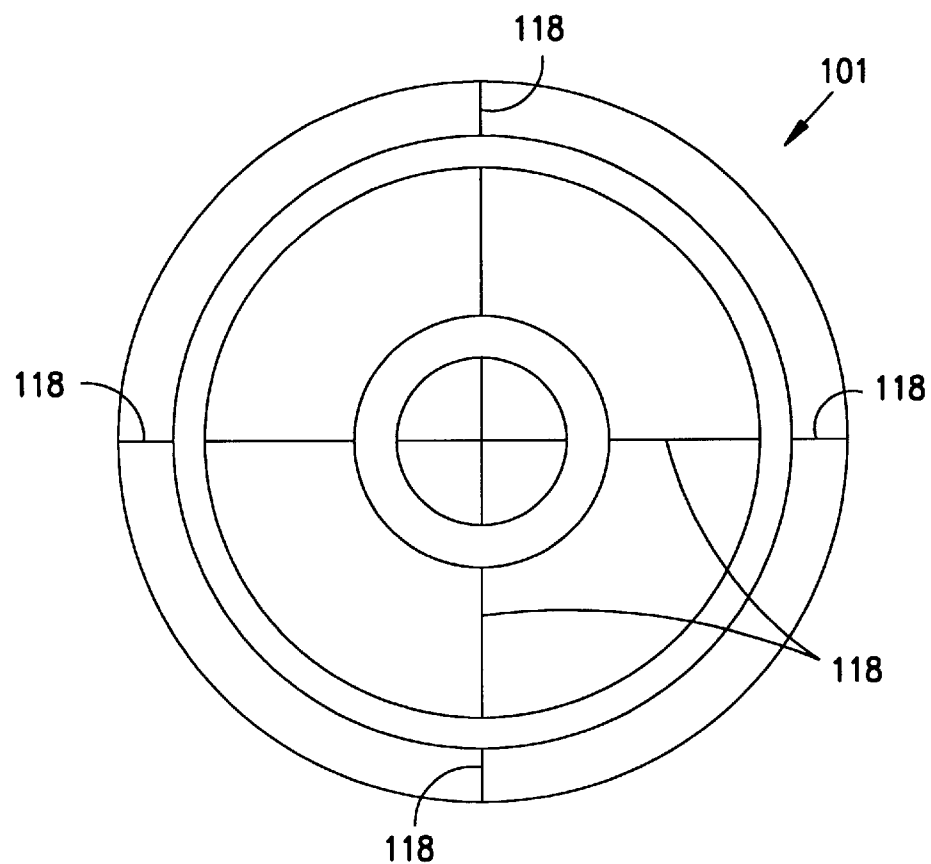
FIG. 6 is a bottom view schematic of a representative pot-core 101 as shown in FIG. 4A, but showing insulating joints 118 which minimize eddy currents.

FIG. 6 is a bottom view schematic of a representative pot-core 101 as shown in FIG. 4A, but showing insulating joints 118 which minimize eddy currents. Insulating joints 118 are made of an electrically insulating material such as Teflon which separate pieces of separately fabricated ferromagnetic material (in this example, four pieces).

C. Receiver Unit 200

Figure 7A:
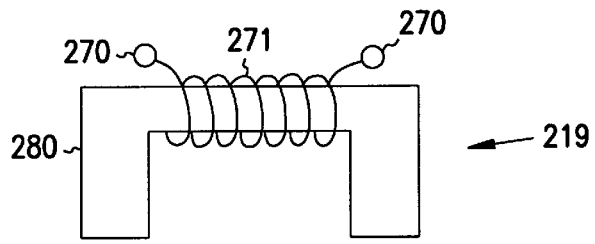
FIG. 7A is a side view section schematic of a representative Absolute sensor 219 with a U-shaped core

FIG. 7A is a side view section schematic of a representative Absolute sensor 219 with a U-shaped core 280 and a single winding 271 having two connections 270.

Figure 7B:
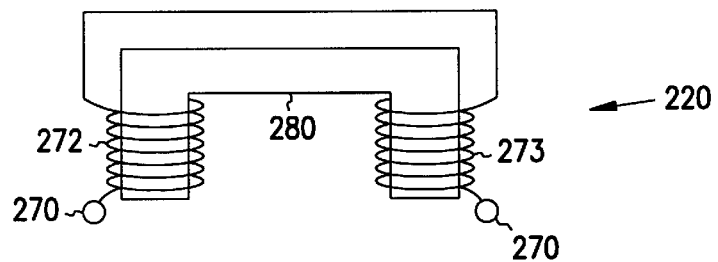
FIG. 7B is a side view section schematic of a representative Differential sensor 220 with a U-shaped core

FIG. 7B is a side view section schematic of a representative Differential sensor 220 with a U-shaped core 280 and dual windings 272 and 273.

Figure 7C:
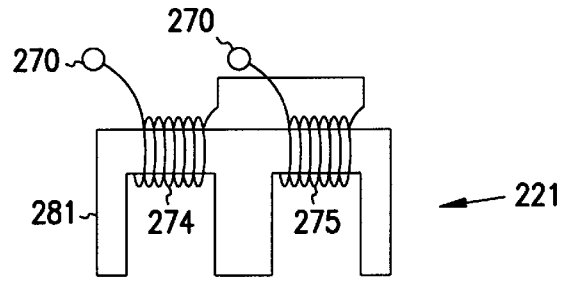
FIG. 7C is a side view section schematic of a representative Differential sensor 221 with a E-shaped core, option #1

FIG. 7C is a side view section schematic of a representative Differential sensor 221 with a E-shaped core 281 and dual windings 274 and 275.

Figure 7D:
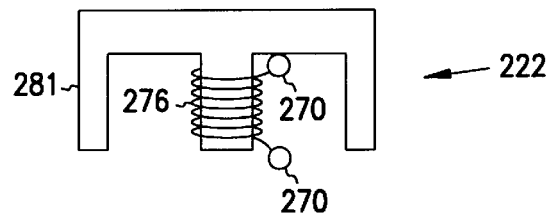
FIG. 7D is a side view section schematic of a representative Differential sensor 222 with a E-shaped core, option #2

FIG. 7D is a side view section schematic of a representative Differential sensor 222 with a E-shaped core 281 and a single winding 276.

Figure 7E:
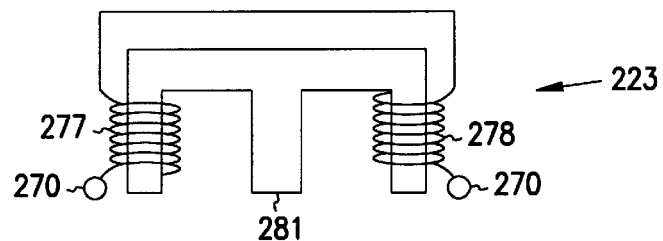
FIG. 7E is a side view section schematic of a representative Differential sensor 223 with a E-shaped core, option #3

FIG. 7E is a side view section schematic of a representative Differential sensor 223 with a E-shaped core 281 and dual windings 277 and 278.

Figure 7F:
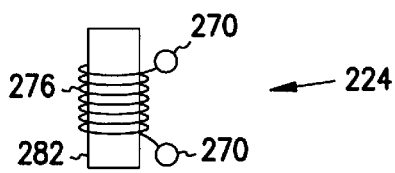
FIG. 7F is a side view section schematic of a representative absolute sensor 224 with an I-shaped core.

FIG. 7F is a side view section schematic of a representative absolute sensor 224 with an I-shaped core 282 and a single winding 276.

Figure 8:
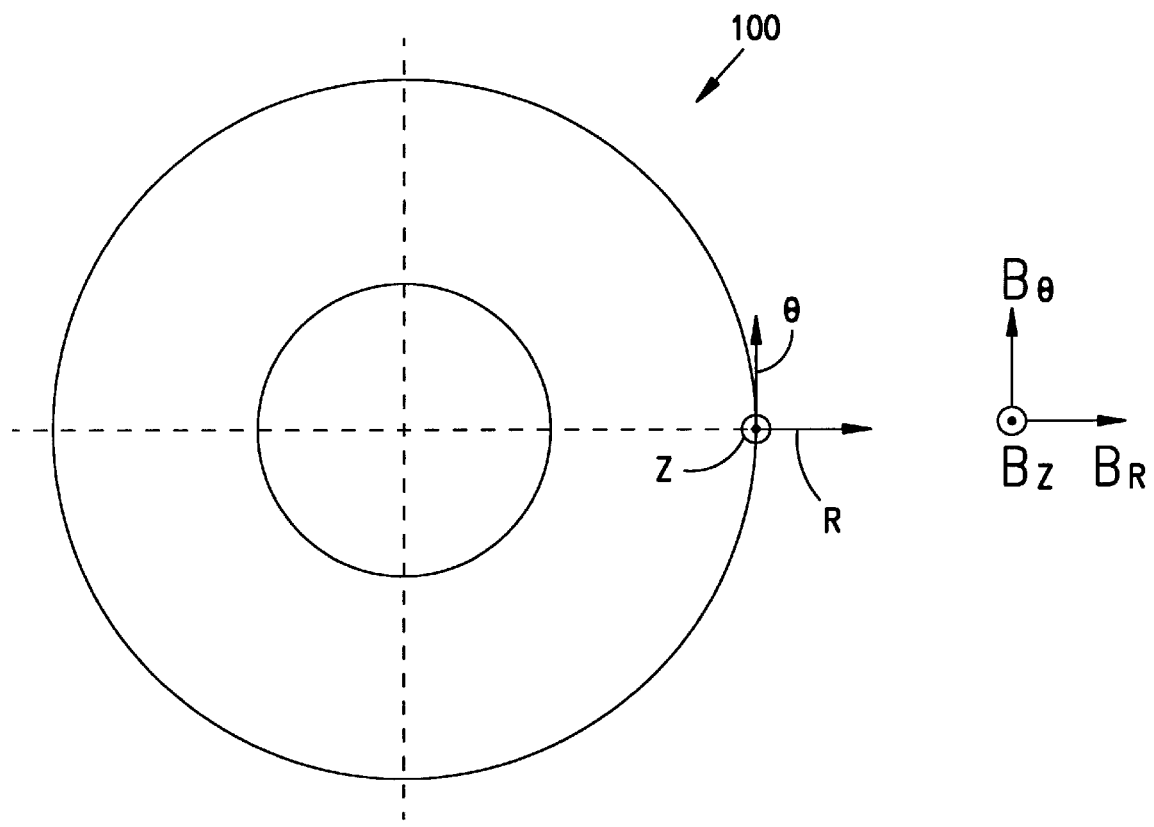
FIG. 8 is a bottom view schematic of a representative PRFEC system 100 showing the orientation of directions R, $\Theta$, and Z, and magnetic fields $B_R$, $B_\Theta$ and $B_Z$.

FIG. 8 is a bottom view schematic of a representative PRFEC system 100 showing the orientation of directions R, $\Theta$, and Z, and magnetic fields $B_R$, $B_\Theta$ and $B_Z$ In one embodiment, receiver unit 200 comprises one or more pickup coil(s) 204 (see FIG. 3), each having a magnetic, non-conducting or weakly conducting core 205 for each receiver unit 200, and a highly conducting shield 207 (made from a material such as aluminum).

In the embodiment shown in FIG. 3, the receiver unit 200 includes a wound-wire coil 204 and a core 205 which is used to shape or guide the field detected by the coil or coils. In another embodiment, in order to provide a more sensitive detector, receiver unit 200 includes a magneto-resistive (MR) sensor such as are known in the magnetic-sensing art (one example of such sensors are MR heads used in some hard-disk data drives). In yet another embodiment, in order to provide a more sensitive detector, receiver unit 200 includes a "squid" type magnetic sensor which includes superconductive parts.

In the embodiment shown in FIG. 3, the receiver unit shield 207 is made of one layer of solid aluminum. In another embodiment shown in FIG. 5l, used in order to enhance the shielding function, the receiver unit shield is made of a laminated structure having two layers of highly conductive material 207' and 207", such as aluminum, laminated on both sides of a ferromagnetic material 241, such as steel. In other embodiments, other numbers of highly conducting layers (such as aluminum) and ferromagnetic layers (such as steel) are used in alternating laminated layers to build the shield for the receiver unit.

The core 205 can be of various different shapes (for examples, see FIGS. 7A–7F), e.g., a U-shaped core can be used for making an absolute sensor 219 or a differential sensor 220, while a E-shaped core can be used for making differential sensors of various structures (221, 222 and 223). An I-shaped core can also be used for making an absolutely sensor 224, however, it may have lower sensitivity than other sensors.

There are three options for a receiver unit orientation depending on which component of the flux density B, $B_R$ (i.e., in a radial direction from excitation probe 100 and along plate 109) $B_\Theta$ (i.e., in a tangential direction) or $B_Z$ (i.e., in a direction substantially perpendicular to the plane of plate 109) (see FIG. 8) is to be measured, and for which kind of defects it is desired to have the probe have the highest sensitivity to. Typically, when defects are expected to have oriented in direction $\Theta$, the receiver unit should be R-direction oriented and the probe scans in the R-direction; while when defects are mostly R-direction aligned, the receiver unit should be oriented in $\Theta$ direction, and the probe scans in the $\Theta$ direction to achieve maximum sensitivity. Sensor 224 of FIG. 7F is an example of the receiver unit 200 option which measures the $B_Z$ flux.

The air-gap between the receiver unit and the plate (gap 208 in FIG. 3.) can be the same of $\delta_2$ or/and $\delta_3$ of FIG. 4 or smaller. A flexible attachment, e.g., a spring-loaded, ferromagnetic part coupled to its lower surface, may also increase the probe's sensitivity, resolution and its signal-to-noise ratio. The part can be: (a.) steel bristles, (b.) steel rollers, (c.) steel fingers, or (d.) other similar structures.

D. Shields

Both the excitation and the receiver units should have substantially complete closed cover(s) made from highly conducting material, e.g., aluminum with a thickness ranged from ½" to ¾". The minimum thickness value of a shield should generally be not less than ⅜". Holes with minimal diameters can be drilled on the shields for electrical cable paths.

The excitation unit and the receiver unit can share a common shield with a certain shielded separation between them as determined either by numerical modeling or by experimental testing.

Highly-conducting materials laminated with alternating layers of ferromagnetic materials are used to enhance the shielding effects in some embodiments.

Numerical Modeling Results

Several prototypes have been simulated using a 2-D (axisymmetric) finite-element code. Detailed data are given below for Models EZ00, EZ38, EZ40 and EZ42 (a modified version of Model EZ40, Model EZ42 is shown in FIG. 10A). Some typical data of Model EZ42 are illustrated in FIGS. 9A–12B, described below.

Figure 9B:
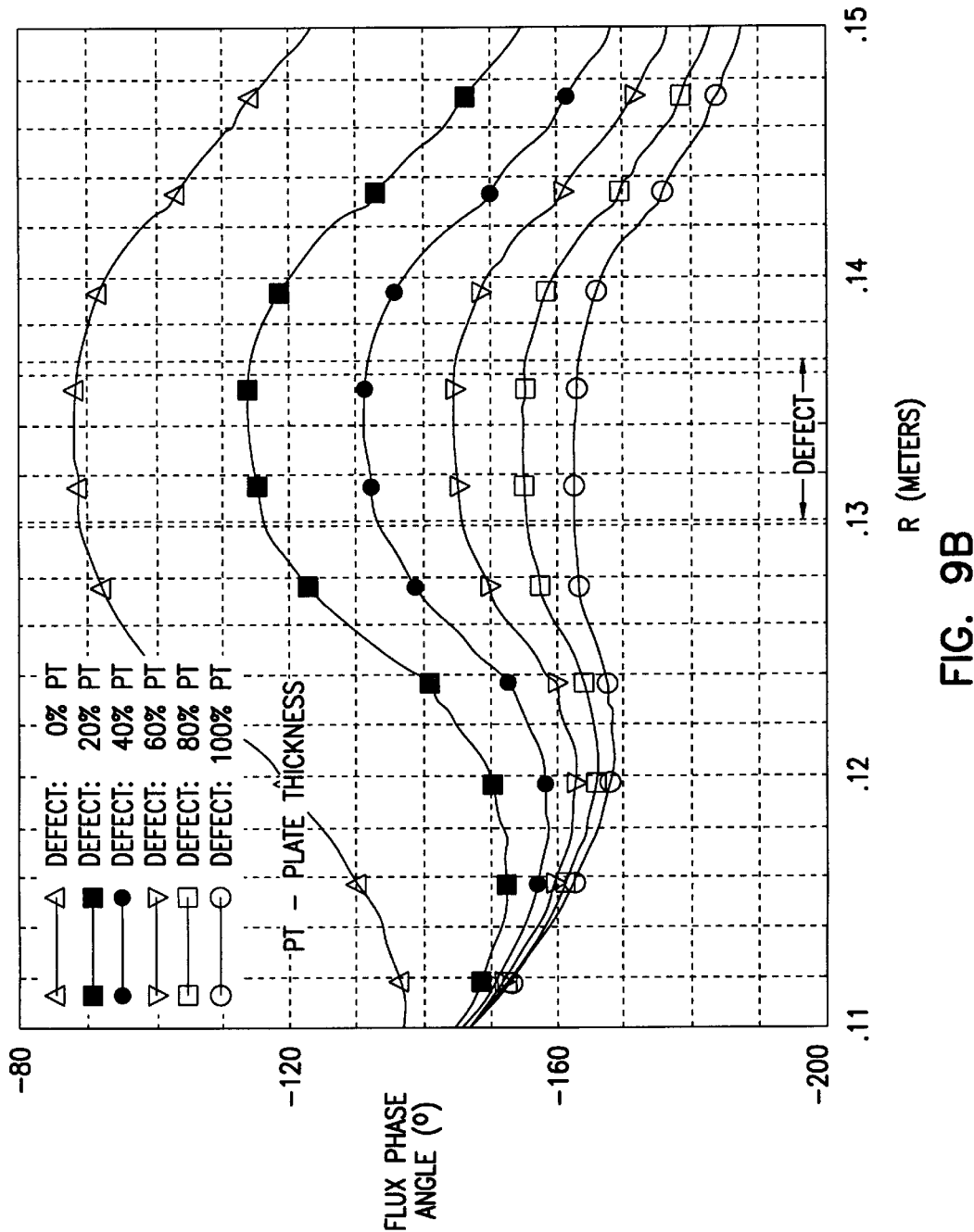
FIG. 9B is a graph of flux phase as a function of distance comparing zero defect and five defect sizes; entitled "Basic Characteristics of Model EZ42:1", Flux Phase Angle Distribution Under Detector for Circumferential Defects of Different Depths.
Figure 10A:
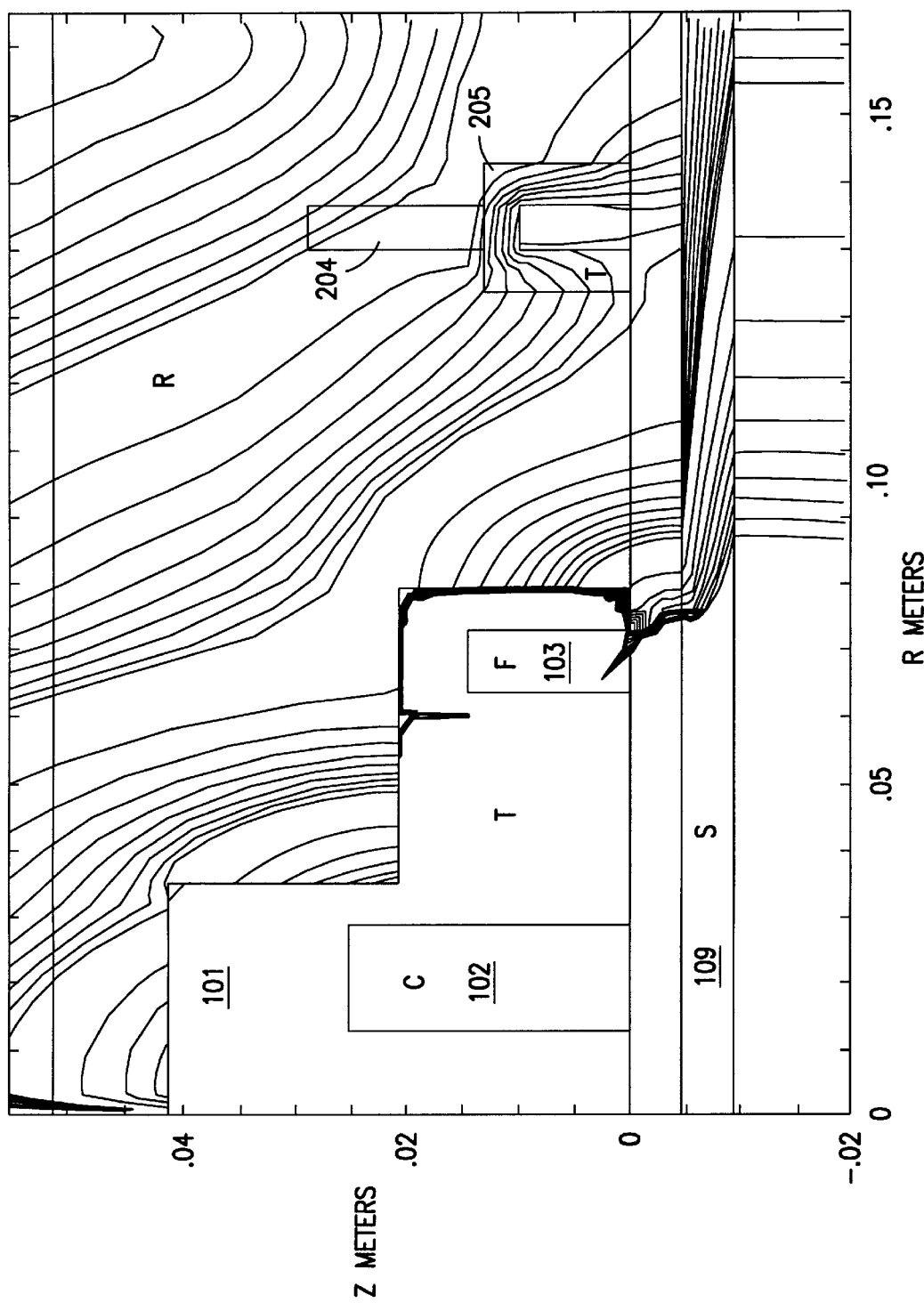
FIG. 10A is a graph of equi-flux magnitude lines for zero defect (showing the last 4 of 8 stages); entitled "Equi-Flux-Magnitude Plot by ContourPlot2d", Example EZ42: RFEC Probe for Inspection of Steel Plates, No. of Stages=8: Last 4 Stages, No Defect Case.

FIG. 9A is a graph of flux magnitude as a function of distance comparing zero defect and five defect sizes. FIG. 9B is a graph of flux phase as a function of distance comparing zero defect and five defect sizes.

Figure 10B:
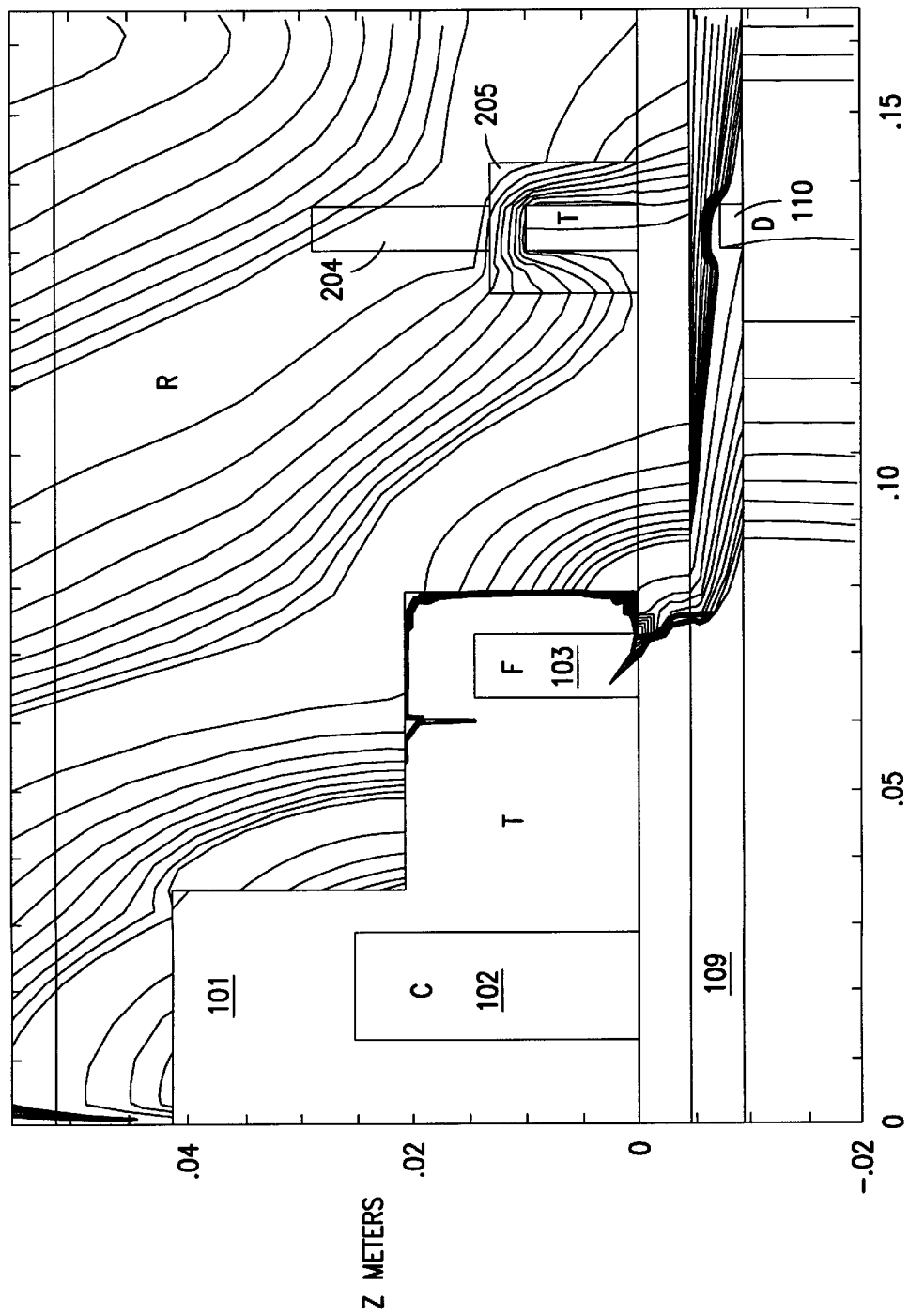
FIG. 10B is a graph of equi-flux magnitude lines for a 40% (of plate thickness) defect on the opposite side of the plate from the probes; entitled "Equi-Flux-Magnitude Plot by ContourPlot2d", Example EZ42: RFEC Probe for Inspection of Steel Plates, No. of Stages=8: Last 4 Stages, Defect: 40% Plate Thickness.

FIG. 10A is a graph of equi-flux magnitude lines for zero defect showing the last 4 of 8 stages (each of these "stages"

shows one order of magnitude of flux strength—for example, a first "stage" is used where field strength is strongest and would show equi-potential lines at 0.9, 0.8, 0.7 . . . and 0.1 of the maximum field; a second "stage" is used where field strength is next strongest and would show equi-potential lines at 0.09, 0.08, 0.07 . . . and 0.01 of the maximum field, a third "stage" is used where field strength is next strongest and would show equi-potential lines at 0.009, 0.008, 0.007 . . . and 0.001 of the maximum field). FIG. 10B is a graph of equi-flux magnitude lines for a 40% (of plate thickness) defect on the opposite side of the plate from the probes.

Figure 11A:
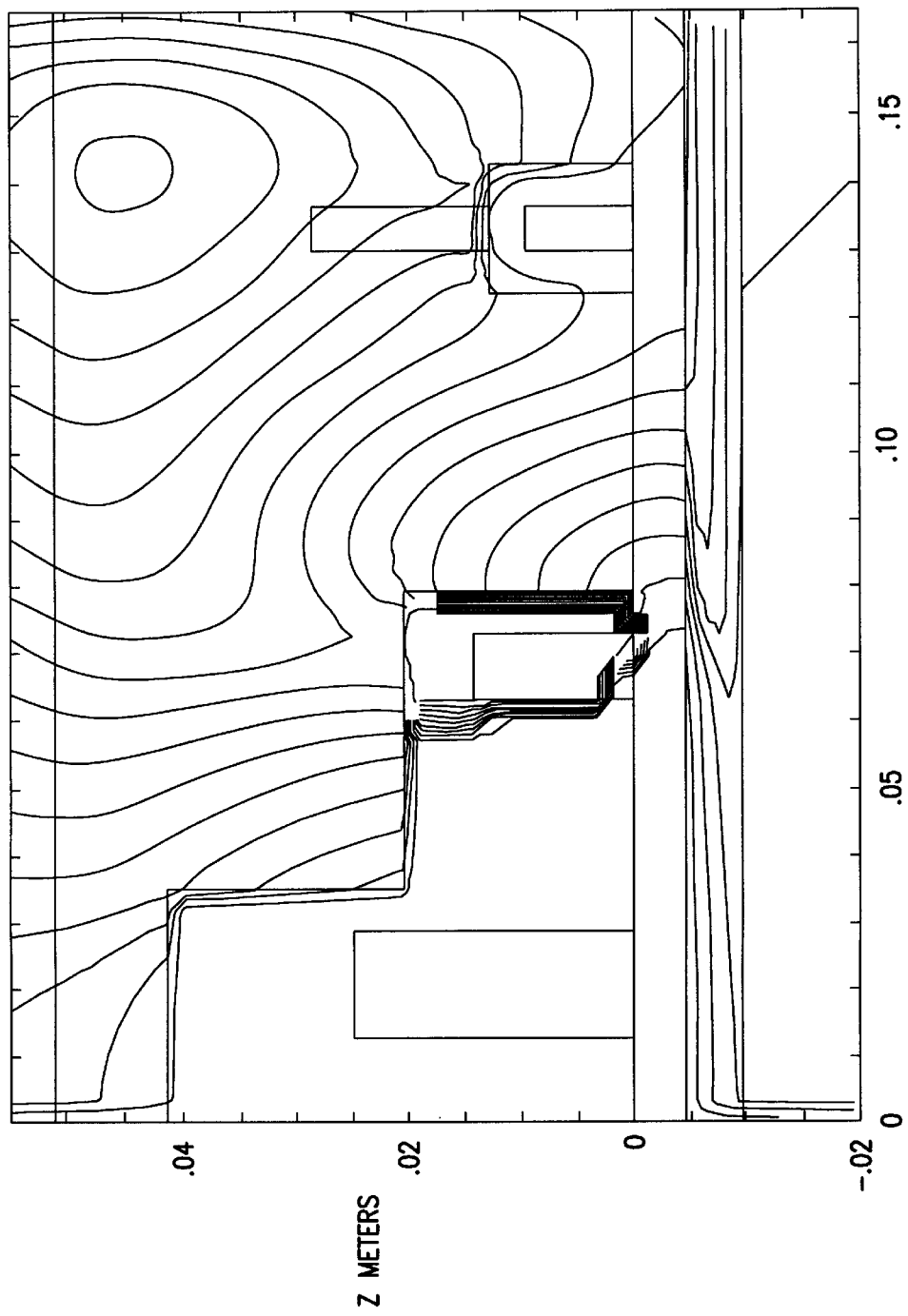
FIG. 11A is a graph of equi-phase lines for zero defect; entitled "Epui-Phase-Plot by the 2D Plotting Codes", Example EZ42: RFEC Probe for Inspection of Steel Plate, Max=180 degrees, Min.=−180 degrees, No. Of Contours=19.
Figure 11B:
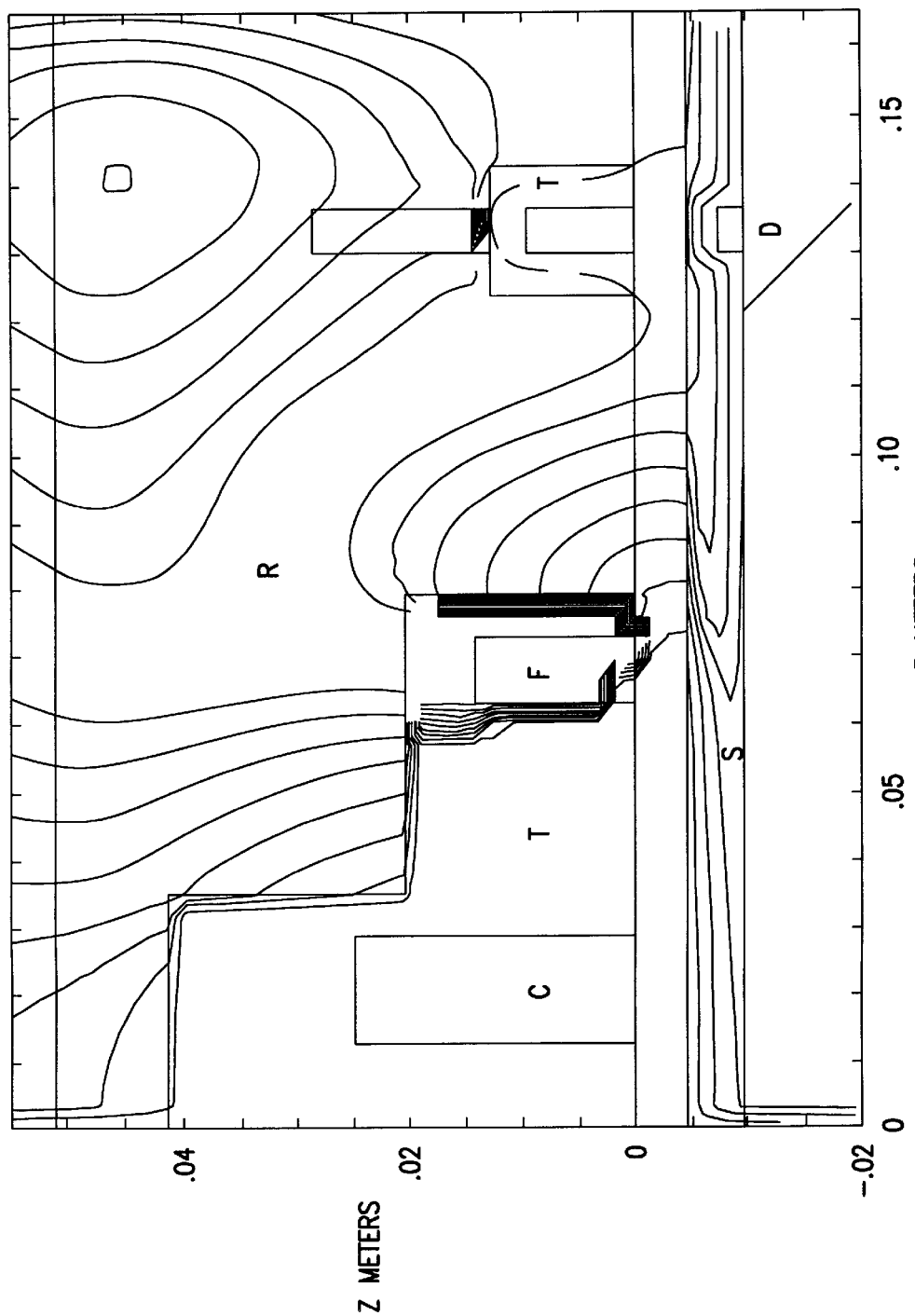
FIG. 11B is a graph of equi-phase lines for a 40% (of plate thickness) defect on the opposite side of the plate from the probes; entitled "Equi-Phase Plot by ContourPlot2D", Example EZ42: RFEC Probe for Inspection of Steel Plate, Max=180 degrees, Min=−180 degrees, No. Of Contours=19, Defect: 40% Plate Thickness.

FIG. 11A is a graph of equi-phase lines for zero defect. FIG. 11B is a graph of equi-phase lines for a 40% (of plate thickness) defect on the opposite side of the plate from the probes.

Figure 12A:
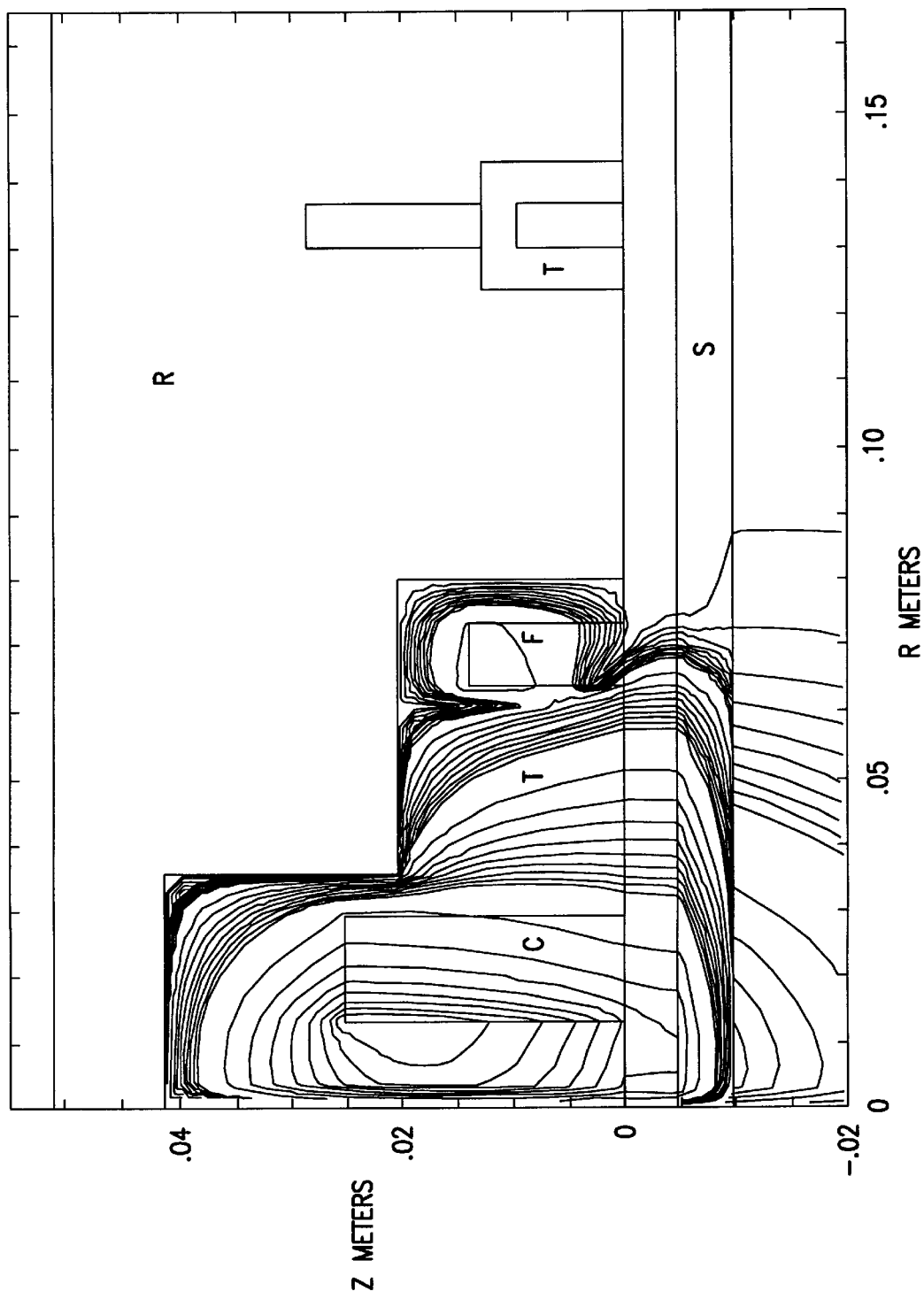
FIG. 12A is a graph of equi-flux magnitude lines for zero defect (showing the first 4 of 8 stages); entitled "Equi-Flux-Magnitude Plot by ContourPlot2D", Example EZ42: RFEC Probe for Inspection of Steel Plates, No. of Stages=8: First 4 Stages, No Defect Case.
Figure 12B:
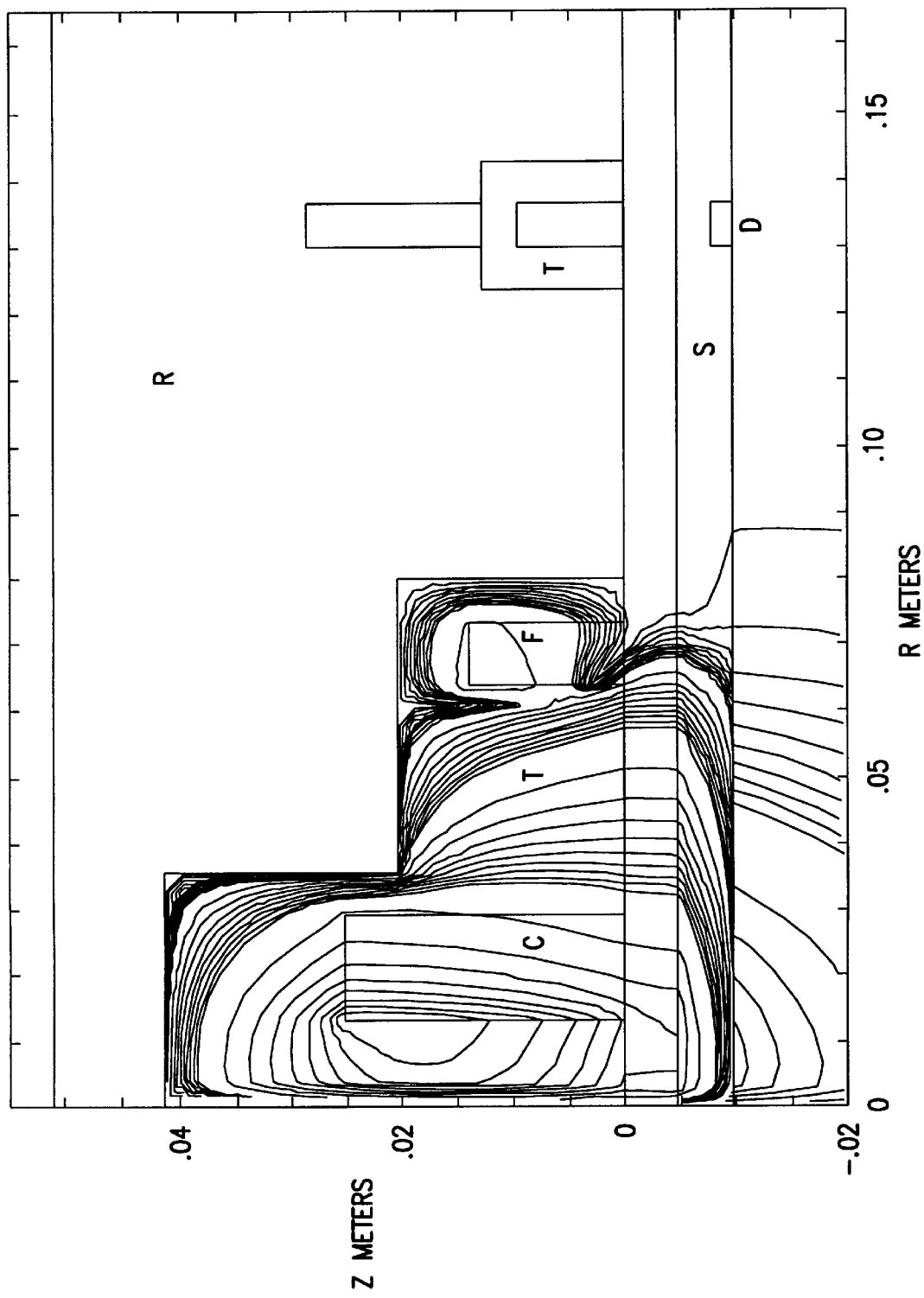
FIG. 12B is a graph of equi-flux magnitude lines for a 40% (of plate thickness) defect on the opposite side of the plate from the probes; entitled "Equi-Flux-Magnitude Plot by ContourPlot2D", Example EZ42: RFEC Probe for Inspection of Steel Plates, No. of Stages=8: First 4 Stages, Defect: 40% Plate Thickness.

FIG. 12A is a graph of equi-flux magnitude lines for zero defect (showing the first 4 of 8 stages). FIG. 12B is a graph of equi-flux magnitude lines for a 40% (of plate thickness) defect on the opposite side of the plate from the probes.

From modeling, it is apparent that both the magnitude and the phase of the magnetic field vary with the defect depth, and that the phase has an approximately linear relationship with the defect depth. The perturbation to the field, due to the presence of a defect, can be clearly seen on these plots.

Another Probe Structure

The exemplary computer-simulated PRFEC probe Model EZ00 (FIG. 13) is a design based on the present invention which is a result of thorough study and understanding of the physics of the RFEC phenomena. The probe consists of two parts: the excitation part 100 (FIG. 14) and pick-up part 200 (FIG. 15). Both are shielded with a single thick aluminum cover R 106, which in this embodiment, is a single-piece shield covering both parts.

The primary coil C 102 in the excitation part of the probe is applied a AC current of, e.g., 15 Hz, which establishes an electromagnetic field in the air-gap 108 between the ferrite core $T_1$ 101 and the steel plate 109 under inspection. One part of the field electromagnetic energy, the "direct coupling" part, spreads out over the plate 109, but its propagation is restricted by both the shield R 106 and the current of the auxiliary coil F 103 (which, in this embodiment is wound on the outside of excitation core 101, rather than in a slot 126).

Another part of the field electromagnetic energy, the indirect coupling part, penetrates the plate wall of plate 109 with eddy current loss, energy dispersion, attenuating and phase shifat, and reaches another side of the plate, and then, spreading out down the plate surface, penetrates back through the wall again at those places where the plate upper side field is weaker than lower side field. The pick-up part 200, which is the detector, is put right there; and therefore its signal phase lag represents the conditions of the plate wall where the field energy passes through plate 109.

The auxiliary coil current is adjusted at an appropriate magnitude and phase, so that its field can completely cancel the direct coupling field in a region, in order that the indirect coupling field energy can penetrate back from the lower side of the plate. (Since the electromagnetic field generated depends on both current and the number of turns, in a relationship amperexturns, the "current" magnitude needed depends in the number of turns in the winding of a coil, thus a coil with a higher number of turns can be driven with a lower current.)

The pick-up part 200 of the probe consists of a detector coil 204 with a ferrite pick-up core $T_2$ 205. In this embodiment, detector coil 204 and pick-up core $T_2$ 205 are covered by a thick steel cup S 208 to get a better shielding from the direct coupling field. Modeling shows steel cover 208 is not much help in some cases.

Computer Simulation Results

One computer simulation done covered the following topics:

1. Magnitude and phase variations of the probe detector magnetic field at a design air-gap 108 of 8 mm, due to a defect of different depths at different part of the steel plate under inspection: under the detector (FIGS. 16 and 17), under the auxiliary coil (FIGS. 18 and 19), under the main coil (FIGS. 20 and 21) and a 20% general wall thinning (FIGS. 22 and 23). Table 1 below lists all the notations used in the FIGS. 16–44 of this discussion.
2. Air-gap dependence of all the above characteristics, i.e. magnetic field magnitude and phase variations at a reduced air-gap 108 of 4 mm. FIGS. 24 and 25 give results with a defect under the detector, FIGS. 26 and 27—under the auxiliary coil, FIGS. 28 and 29—under the main coil and FIGS. 30 and 31—a 20% general wall thinning of the plate.
3. Comparison of magnetic field variation due to an upper surface defect and a lower surface defect (FIGS. 32, 33, 34, and 35).
4. Some typical field plots of the detector region: non-defect case (FIGS. 36, 37, and 38), 40% deep upper defect (FIGS. 39, 40, and 41), 40% deep lower surface defect (FIGS. 42, 43, and 44).

Some Comments to Prototype production and Testing

1. The aluminum shield 106 can be used as the probe frame. It can be thicker where it is necessary. However, if any significant change of it made in the final design of the probe, a second computer simulation is suggested.
2. The material for the two cores, $T_1$ 101 and $T_2$ 205, can be replaced by any other ferromagnetic one, provided that there is no significant eddy current formed in it in its operation.
3. An additional electric circuit or network is needed for providing an adjustable, in both magnitude and phase, current to the auxiliary coil F 103. The adjustment of auxiliary coil F current is a key of getting the PRFEC phenomena in the probe. Therefore, a carefully designed network with both coarse and fine adjustment controls for both magnitude and phase is desired.
4. A piece (>2 m×2 m) of relatively thick (>2.0×thickness of the steel plate under inspection) steel plate can be used for adjustment of the auxiliary coil.

TABLE 1

Notations used in the FIGS. 16–44

| Notations | Problem name | Field quantity | air-gap 108 | Defect |
| --- | --- | --- | --- | --- |
| phez10 | ez10 | phase | 8 mm | none |
| phez11 | ez11 | phase | 8 mm | 40% deep, upper, under detector |
| phez12 | ez12 | phase | 8 mm | 80% deep, upper under detector |
| phez13 | ez13 | phase | 8 mm | 100% deep, upper under detector |
| phez60 | ez60 | phase | 8 mm | 20% general wall thinning |

TABLE 1-continued

Notations used in the FIGS. 16–44

| Notations | Problem name | Field quantity | air-gap 108 | Defect |
|---|---|---|---|---|
| phez71 | ez71 | phase | 8 mm | 40% deep, lower, under detector |
| phez20 | ez20 | phase | 4 mm | none |
| phez21 | ez21 | phase | 4 mm | 40% deep, upper, under detector |
| phez22 | ez22 | phase | 4 mm | 80% deep, upper under detector |
| phez23 | ez23 | phase | 4 mm | 100% deep, upper under detector |
| phez50 | ez50 | phase | 4 mm | 20% general wall thinning |
| mez10 | ez10 | magnitude | 8 mm | none |
| mez11 | ez11 | magnitude | 8 mm | 40% deep, upper, under detector |
| mez12 | ez12 | magnitude | 8 mm | 80% deep, upper under detector |
| mez13 | ez13 | magnitude | 8 mm | 100% deep, upper under detector |
| mez60 | ez60 | magnitude | 8 mm | 20% general wall thinning |
| mez71 | ez71 | magnitude | 8 mm | 40% deep, lower, under detector |
| mez20 | ez20 | magnitude | 4 mm | none |
| mez21 | ez21 | magnitude | 4 mm | 40% deep, upper, under detector |
| mez22 | ez22 | magnitude | 4 mm | 80% deep, upper under detector |
| mez23 | ez23 | magnitude | 4 mm | 100% deep, upper under detector |
| mez50 | ez50 | magnitude | 4 mm | 20% general wall thinning |

Some Conclusions from Computer Aided Simulation and Design of Remote Field Eddy Current Probe Working Model for Inspection of Steel Plates The computer simulation results from 31 different geometrical variations, 4 different frequencies (15 Hz, 35 Hz, 70 Hz and 90 Hz), as well as some material property changes give the following conclusions:

(a). The exemplary Model EZ38, shown in FIGS. 45, 46 and 47, works at frequency f from approximately 35 to 70 Hz for inspection of steel planes with thickness, T, relative initial permeability, $\mu_{ro}$, and $T \times \mu_{ro}$ no greater than $\frac{3}{16}'' \times 150$ under a condition of the air-gap 108, no greater than $\frac{3}{16}''$. However, any requirement for increasing T or/and $\mu_{ro}$ can be solved by decreasing air-gap 108 or by increasing model geometrical dimension.

(b). The exemplary Model EZ40, shown in FIG. 48, which is a reduced model EZ38 scaled by a factor of 0.75 in its r direction and a factor of 0.5 in its z direction, works at the same above conditions but the air-gap 108 should be no greater than $\frac{3}{32}''$.

Model EZ40 here serves as an example showing fatrther potential of the probe size reduction by decreasing the air-gap 108.

c). Geometrical changes of the ferrite core in the excitation part of the probe for engineering implementation convenience are allowed, provided:

i. any cross-section along the magnetic flux path 131 of the excitation core 101 should be greater than the center cross-section surrounded by coil C 102.

ii. no reduction in ratio $A_f/A_c$, where $A_f$ and $A_c$ are the cross-section areas of the ferrite parts surrounded by coils F 103 and C 102, respectively.

iii. no air-gaps on the magnetic flux path (other than air-gap 108 between the probe and the plate 109) or, if a gap is unavoidable, special effort is needed to make any such other air-gap as narrow as possible.

(d). Geometrical changes of the ferrite core 205 in the pick-up part 200 of the probe for engineering implementation convenience are allowed provided that the area of its surface facing the steel plate 109 under inspection is not substantially reduced and is not increased too much.

(e). Geometrical changes of the aluminum shield 106 of the probe for engineering implementation convenience are allowed provided i. its thickness from air (the outside of the probe) to either core 101 or 205 is not substantially reduced.

ii. any cut of the whole piece of metal, when it is necessary, should be aligned along its circumferential direction, so that the cut does not interrupt the eddy current inside the metal.

(f). There is a big variety of possible materials and structures for the detectors 200. For example, they can also be made from silicon steel sheet, as that in a transformer, or can be made using the idea of tape-head for a recorder-player. One suggested allocation of the detectors is shown in FIG. 49.

(g). Permeability variation for ferrite cores within a limit of approximately $1,000 < \mu_{ro} < 10,000$ haave no significant influence to the probe performances.

(h). Any high-permeable material other than the two ferrite cores in the shield region or in the vicinity of the probe does little good to the probe performance, on the contrary, such material sometimes introduces interference. If desirable for some purpose, such highly permeable features may be included and their affect on field shape taken into account.

(i). In one embodiment, two current sources, each providing constant currents independent of the coil impedances, of approximately 30 Hz to 90 Hz are used for coils C 102 and F 103.

(j). The ampere-turns for coil C 102 can be 200 amp-turns to 1000 amp-turns for Model EZ38, and 100 amp-turns to 500 amp-turns for Model EZ40. The value is essentially dependent on practical temperature rises of the coils and the saturation flux density of the ferrite core.

In one embodiment, the ampere-turns for coil F 103 are about 2.5%–6.0% of the ampere-turns for coil C 102, with a phase shift about 10°–30° lag behind the current in coil C 102.

(k). A sophisticated circuit is used for fine adjustment of the magnitude and the phase of the current in coil F 103.

Some Calculation Results of Model EZ42 PRFEC Probe for Inspection of Steel Plates One computer simulation of Model EZ42 showed the following results:

(a). At normal air-gap 108 condition (air-gap 108=$\frac{3}{16}''$)

Inductance of a 500-turns excitation coil $L_{500}$=47.3 mH

Its reactance at 35 Hz $X_{35}$=10.4 Ω

Reactance of a coil with N turns working at f Hz:

$$X_{norm} = X_{35} \times (f \div 35) \times (N \div 500)^2$$

At a smaller air-gap 108 condition $L_{500}, X_{35}$ and X increase. For example, an air-gap 108 of $\frac{1}{16}''$, they increase by a factor of 1.62.

(b). At a full plate-atickness condition, induced voltage on a detector of 1.0 inch in its length of circumferential direction and with 5000 turns at an excitation of 500 amp-turns: $E_0$=0.33 mV at the same condition the induced voltage on a detector M inches in its circumferential direction and $N_d$ turns at the same excitation $$E=E_0 \times M \times (N_d \div 5000) \times (I \times N \div 500)$$

at defect cases E has a higher values which are proportional to the flux magnitude. The graph of FIG. 9A shows Basic characteristics of Model EZ42:2 and gives the flux variation versus defect depth at the normal working conditions (the normal working conditions are:

Excitation at 500 ampere-turns for coil C 102;
Appropriately adjusted excitation for coil F 103;
Air-gap 108=3/16";
Frequency=35 Hz;
Material properties are:
  steel 109 inspected: $\sigma=7\times10^6$ s/m, $\mu_r=150$.
  ferrite 101 and 205: $\mu_r=6500$.
  aluminum shield 106: $\sigma=3.5\times10^7$ s/m.).

However, in those cases where there is a region of the inspected plate with greater thickness, or there is a high-conductivity or/and high-permeability, or conductive material placed on the other side of the plate and quite close to it, then E decreases. At a smaller air-gap 108 condition, E increases. For example, at an air-gap 108 of 1/16" E increases by a factor of 6.1.

(c). At the normal condition for this particular design, detector phase varies in range of about 90° at full plate-thickness (e.g., the detector voltage phase could be at approximately 100° for no defect and range up to nearly 190° for a defect which goes nearly 100% through plate 109. The FIG. 9B graph Basic Characteristics of Model EZ42:1 gives the normal condition variation of the flux phase.

The phase variation increases with increase of $\sigma$, $\mu_r$ or/and thickness of the plate, as well as the excitation frequency. The following suggestions for a possible test set-up are a consequence of the above results:

(a). The probe uses a constant current power supply providing a constant ampere-turns I×N for the excitation. As I×N must be invariable with the coil impedance change, it is required that the power supply to provide a voltage V satisfying $V>K_V \times I \times X_{norm}$ (wherein, for this particular embodiment, $K_V=5.0$) and a resistance or reactance is needed to limit and adjust the excitation current I. $K_V$ can be greatly reduced by proper modification to the probe design.

(b). The phase meter to be working in the fill range of −180° to 180°, or a range with a total scale of 360°.

(c). The phase-meter to be able to pick up signals at 0.01 to 0.1 mV, or, a preamplifier of such level of sensitivity to be available to work with the phase-meter.

FIG. 52 shows a cross-section schematic showing an embodiment of the invention with the receiver unit placed at the center of the probe, while the primary coil 102 and its core 101 are placed close to the outer-most wall of the probe, and the auxiliary coil 103 is between surrounded by shield 106.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A remote-field eddy-current probe system for inspecting a conductive plate, the probe system comprising:
    an excitation unit, the excitation unit comprising:
        an excitation core;
        a primary excitation coil coupled to the excitation core which generates a magnetic field;
        an auxiliary unit coupled to the excitation core which guides the magnetic field into the conductive plate and minimizes the magnetic field not passing into the conductive plate; and
        a first shielding cover substantially surrounding the excitation core on substantially all sides except a probing face positioned towards the conductive plate; and
    at least one magnetic signal receiver unit,
    wherein the excitation unit is configured to guide the magnetic field into the conductive plate from a first side of the conductive plate and minimize the magnetic field not passing into the conductive plate in order to provide a remote-field eddy-current magnetic signal detected by the at at least one magnetic signal receiver unit that passaed through the plate twice to a location of the at least one magnetic signal receiver unit that is separated from the excitation coil and on the first side of the conductive plate.

2. A method for inspecting a plate, comprising the steps of:
    generating an alternating-current (AC) primary excitation electromagnetic field on a first side of the plate, the AC primary field having a periodic waveform, the periodic waveform having a frequency or time period;
    generating an AC auxiliary excitation electromagnetic field at said frequency or time period and at a magnitude and a phase angle or time shift relative to the primary electromagnetic field in order to generate a combined electromagnetic field and to force the combined electromagnetic field into the plate and to minimize directly-coupled field;
    shielding the combined excitation field on all sides except towards the plate; and
    detecting a result rernote-field eddy-current electromagnetic field signal of the combined electromagnetic field in a remote-field region on the first side of the plate such that the signal has passed through the plate twice wherein said result signal has a phase angle that is substantially proportional to a thickness of the metal plate.

3. The method according to claim 2, further comprising the step of comparing a phase angle of the detected result electromagnetic field with a phase angle of one of the excitation electromagnetic fields.

4. The method according to claim 2, wherein the step of detecting a result electromagnetic field includes detecting a differential signal.

5. The method according to claim 2, further comprising the step of detecting a phase angle change in the detected result electromagnetic field.

6. A method for inspecting a metal plate using a remote-field eddy-current effect, comprising:
    generating an alternating primary excitation magnetic field by driving a first signal into a first coil located on a first side of the metal plate, the alternating primary excitation magnetic field having a periodic waveform with a frequency determined by $$f=c/(\sigma \mu r_2)$$

where $\sigma$ is the conductivity of the conductive plate, (s/m); $\mu$ is its permeability, (T.m/A); $\tau$ is its thickness, (m); and c =0.03 to 3.0;

shielding the combined excitation field on all sides except towards the plate; and detecting a result magnetic field in a remote-field region wherein said result magnetic field has a phase angle that is substantially proportional to a thickness of the metal plate.

7. The method according to claim 6, further comprising:

comparing a phase angle of an electrical signal representative of the detected result magnetic field with a phase angle that is related to the excitation magnetic field.

8. A remote-field eddy-current probe system for inspecting a metal plate, the probe system comprising:

a magnetic signal receiver; and an excitation element, the excitation element comprising:
an excitation core;
a primary excitation coil coupled to the excitation core which generates an alternating primary excitation magnetic field with a frequency determined by $$f=c/(\sigma\mu\tau^2)$$

where $\sigma$ is the conductivity of the conductive plate, (s/m); $\mu$ is its permeability, (T.m/A); $\tau$ is its thickness, (m); and c=0.03 to 3.0; and a first shielding cover substantially surrounding the excitation core on substantially all sides except a probing face positioned towards the plate;

wherein the receiver is located in a remote-field region in order to detect an alternating magnetic signal that has passed through the plate twice and thus has a phase delay, relative to a corresponding phase of the primary excitation current, that is substantially proportional to a thickness of the metal plate.

9. The remote-field eddy-current probe system according to claim 8, further comprising an auxiliary unit coupled to the excitation core which guides the magnetic field into the conductive plate and minimizes the magnetic field not passing into the conductive plate.

10. The remote-field eddy-current probe system according to claim 9, wherein the auxiliary unit includes an auxiliary excitation coil.

11. The remote-field eddy-current probe system according to claim 10, in which the excitation core has a slot for the auxiliary coil which is placed at a substantially outer-most position of the excitation core.

12. The remote-field eddy-current probe system according to claim 11, in which the excitation core is designed following the relation: $(\delta_1/A_1)/(\delta_2/A_2)$ is greater than approximately 10, in which $A_1$ is an area substantially equal to a first portion of the excitation core which is within the primary excitation coil, $\delta_1$ is a thickness of an air gap between the first portion of the excitation core and the conductive plate, $A_2$ is an area substantially equal to a second portion of the excitation core which is within the secondary coil, and $\delta_2$ is a thickness of an air gap between the second portion of the excitation core and the conductive plate.

13. The remote-field eddy-current probe system according to claim 10, in which the primary excitation coil and the auxiliary excitation coil both serve as sources of an alternating current (AC) electromagnetic field as for probe operation, and where an AC signal is coupled to the primary excitation coil, an AC signal is coupled to the auxiliary excitation coil, and the AC signal coupled to the primary coil has a frequency or time period equal to a frequency or time period, respectively, of the AC signal coupled to the auxiliary excitation coil and the AC signal coupled to the primary coil is phase or time shifted relative to a corresponding phase or time of the AC signal coupled to the auxiliary excitation coil.

14. The remote-field eddy-current probe system according to claim 13, wherein the AC signal coupled to the primary excitation coil is a low-frequency AC signal having a periodic waveform, and wherein the primary-coil AC signal has a frequency in the range of approximately 10 Hz to 150 Hz for a case where the conductive plate is a carbon steel plate, the frequency determined by:

$$f=c/(\sigma\mu\tau^2)$$

where $\sigma$ is the conductivity of the conductive plate, (s/m); $\mu$ is its permeability, (T.m/A); $\tau$ is its thickness, (m); and c =0.03 to 3.0.

15. The remote-field eddy-current probe system according to claim 13, further comprising a source of low-frequency alternating current (AC) current for each of the primary excitation coil and auxiliary excitation coil, the AC current for the primary excitation coil and for the auxiliary excitation coil each having a periodic waveform, wherein the AC current for the auxiliary excitation coil has a current magnitude, $I_a$, and phase, $\theta_a$, which are determined experimentally under maximal expected value of $\delta_2$ in the inspection, and using the following equations:

$$I_a=V_{pt}/V_{at};$$

and $$\theta_a=\theta_{at}+180°\theta_{pt}+\theta_p.$$

16. The remote-field eddy-current probe system according to claim 2, wherein the shielding cover includes a layer of a highly conducting material with a minimum thickness of approximately 3/8".

17. The remote-field eddy-current probe system according to claim 2, in which the receiver unit comprises:

at least one ferromagnetic pick-up core;

at least one pick-up coil, each of the at least one pick-up coils coupled to one or more of the at least one ferromagnetic pick-up cores; and at least one pick-up shielding cover made of highly conducting material and having a minimum thickness of at least approximately 3/8" and covering the at least one ferromagnetic pick-up core except on a sensing face.

18. The remote-field eddy-current probe system according to claim 17, in which the receiver unit includes either a magnetoresistive element or a superconducting quantum interference device (SQUID).

19. The remote-field eddy-current probe system according to claim 18, in which the receiver unit detects a differential signal.

20. The remote-field eddy-current probe system according to claim 16, in which primarily one of three components of a flux density B, either $B_R$, $B_\Theta$ or $B_Z$, is detected by the receiver.

21. The remote-field eddy-current system according to claim 20, wherein magnitude and phase of detected signals are used for defect or anomaly identification.

22. The remote-field eddy-current system according to claim 17, wherein a voltage signal induced in the at least one pick-up coil is detected.

23. The remote-field eddy-current system according to claim 22, wherein magnitude and phase of detected signals are used for defect or anomaly identification.

24. The remote-field eddy-current probe system according to claim 9, wherein the excitation core is designed following the relation: $(\delta_1/A_1)/(\delta_2/A_2)$ is greater than approximately ten (10), in which $A_1$, is an area substantially equal to a first portion of the excitation core which is within the primary excitation coil, $\delta_1$ is a thickness of an air gap between the first portion of the excitation core and the conductive plate, $A_2$ is an area substantially equal to a second portion of the excitation core, and $\delta_2$ is a thickness of an air gap between the second portion of the excitation core and the conductive plate.

25. The remote-field eddy-current probe system according to claim 2, wherein the magnetic signal receiver detects a phase angle change in the detected electromagnetic field.

26. The remote-field eddy-current probe system according to claim 2, in which the magnetic signal receiver comprises:
   at least one ferromagnetic pick-up core;
   at least one pick-up coil, each of the at least one pick-up coils coupled to one or more of the at least one ferromagnetic pick-up cores; and
   at least one pick-up shielding cover made of highly conducting material and covering the at least one ferromagnetic pick-up core except on a sensing face.

27. The remote-field eddy-current probe system according to claim 8, in which the excitation core is made of ferromagnetic material that is either non-conducting, weakly conducting, or conducting.

28. The remote-field eddy-current probe system according to claim 8, in which the excitation core is made of ferromagnetic material that is conducting but having insulating joints which minimize eddy currents induced in the excitation core by signal from the primary excitation coil.

29. The remote-field eddy-current probe system according to claim 8, in which the excitation core is a substantially closed magnetic circuit of any shape but with an opening towards the conductive plate, and having a minimum cross-section area at a region surrounded by the primary excitation coil.

30. The remote-field eddy-current probe system according to claim 8, wherein the magnetic signal receiver includes one or more magnetoresistive element.

31. The remote-field eddy-current probe system according to claim 8, wherein the magnetic signal receiver includes one or more superconducting quantum interference device (SQUID).

32. The remote-field eddy-current probe system according to claim 8, wherein the magnetic signal receiver detects a differential signal.

33. The remote-field eddy-current probe system according to claim 8, wherein primarily one of three components of a flux density B, either $B_R$, $B_\Theta$ or $B_Z$ is detected by the receiver.

34. The remote-field eddy-current system according to claim 8, wherein a voltage signal induced in the magnetic signal receiver is detected.

35. The remote-field eddy-current system according to claim 34, wherein a magnitude and a phase of th detected voltagae signal are used for defect or anomaly identification.

36. The remote-field eddy-current probe system according to claim 8, wherein the excitation core is designed following the relation: $(\delta_1/A_1)/(\delta_2/A_2)$ is greater than approximately ten (10), in which $A_1$, is an area substantially equal to a first portion of the excitation core which is within the primary excitation coil, $\delta_1$ is a thickness of an air gap between the first portion of the excitation core and the conductive plate, $A_2$ is an area substantially equal to a second portion of the excitation core, and $\delta_2$ is a thickness of an air gap between the second portion of the plate excitation core and the conductive plate.

37. The remote-field eddy-current probe system according to claim 8, wherein the shielding cover includes a layer of a highly conducting material with a minimum thickness of approximately ⅜".

38. The remote-field eddy-current probe system according to claim 8, wherein the magnetic signal receiver includes a differential sensor.

39. The remote-field eddy-current probe system according to claim 8, wherein substantially all of the magnetic field to be detected has a phase delay, relative to a corresponding phase of the primary excitation current, that is substantially proportional to a thickness of the plate.

40. The remote-field eddy-current probe system according to claim 8, faurther comprising:
   an auxiliary excitation coil coupled to the excitation core which guides the magnetic field to pass through the plate and minimizes the magnetic field not passing through the plate; and
   an electrical driving circuit that drives a primary electrical signal to the primary excitation coil, and drives an auxiliary electrical signal to the auxiliary excitation coil such that a phase of the auxiliary electrical signal is shifted from a corresponding phase of the primary electrical signal.

41. The remote-field eddy-current probe system according to claim 40, wherein the alternating primary excitation magnetic field is shaped, at least in part, by generating an alternating auxiliary excitation magnetic field with a second coil at said frequency or time period and at a magnitude and a phase angle or time shift relative to the primary magnetic field in order to generate a combined electromagnetic field and to force the combined electromagnetic field to pass twice through the plate and thus to have a detectable phase delay, relative to a corresponding phase of the primary excitation current, that is substantially proportional to a thickness of the plate.

42. The remote-field eddy-current probe system according to claim 40, further comprising:
   a comparing element that compares a phase angle of an electrical signal generated by the receiver with a phase angle related to the primary or the auxiliary electrical signals.

43. The remote-field eddy-current probe system according to claim 8, further comprising:
   a comparing element that detects a phase angle change due to a defect in the plate.

44. The remote-field eddy-current probe system according to claim 8, wherein the maganetic signal receiver detects a phase angle change in the detected electromagnetic field.

45. The remote-field eddy-current probe system according to claim 8, in which the magnetic signal receiver comprises:
   at least one ferromagnetic pick-up core;
   at least one pick-up coil, each of the at least one pick-up coils coupled to one or more of the at least one ferromagnetic pick-up cores; and
   at least one pick-up shielding cover made of highly conducting material and covering the at least one ferromagnetic pick-up core except on a sensing face.

46. The remote-field eddy-current probe system according to claim 45, wherein the magnetic signal receiver detects a differential signal.

47. The remote-field eddy-current probe system according to claim 46, wherein primarily a $B_R$ component of a flux density B is detected by the receiver.

48. The remote-field eddy-current probe system according to claim 46, wherein primarily a $B_\Theta$ component of a flux density B is detected by the receiver.

49. The remote-field eddy-current probe system according to claim 46, wherein primarily a $B_Z$ component of a flux density B is detected by the receiver.

50. A remote-field eddy-current probe system for inspecting a metal plate, the probe system comprising:
 a magnetic signal receiver; and
 an excitation element, the excitation element comprising:
  an excitation core; and
  a primary excitation coil coupled to the excitation core which generates an alternating primary excitation magnetic field; and
 a first shielding cover substantially surrounding the magnetic signal receiver on substantially all sides except a probing face positioned towards the plate;
  wherein the receiver is located in a remote-field region in order to detect an alternating magnetic signal that has passed through the plate twice and thus has a phase delay, relative to a corresponding phase of the primary excitation current, that is substantially proportional to a thickness of the metal plate.

51. The remote-field eddy-current probe system according to claim 50, wherein the alternating primary excitation magnetic field has a periodic waveform with a frequency determined by:

$$f = c/(\sigma\mu\tau^2)$$

where $\sigma$ is the conductivity of the conductive plate, (s/m); $\mu$ is its permeability, (T.m/A); $\tau$ is its thickness, (m); and c =0.03 to 3.0.

52. The remote-field eddy-current probe system according to claim 50, wherein the receiver detects a differential electromagnetic signal.

53. The remote-field eddy-current probe system according to claim 52, wherein primarily a $B_R$ component of a flux density B is detected by the receiver.

54. The remote-field eddy-current probe system according to claim 52, wherein primarily a $B_\Theta$ component of a flux density B is detected by the receiver.

55. The remote-field eddy-current probe system according to claim 52, wherein primarily a $B_Z$ component of a flux density B is detected by the receiver.

* * * * *

UNITED STATES PATENT AND TRADEMARK OFFICE
CERTIFICATE OF CORRECTION

PATENT NO. : 6,002,251
DATED : December 14, 1999
INVENTOR(S) : Yu-shi Sun

It is certified that error appears in the above-identified patent and that said Letters Patent is hereby corrected as shown below:

Column 1,
Line 43, delete "spark, Nev.", and insert -- Spark, Nev. --, therefor.
Line 43, 46 and 51, delete "millon", and insert -- million --, therefor.
Line 63, delete "Acoatstic", and insert -- Acoustic --, therefor.
Line 64, delete "AE work well", and insert -- AE works well --, therefor.
Line 64, delete "does anaiot", and insert -- does not --, therefor.

Column 3,
Line 8, delete "in a least", and insert -- in at least --, therefor.
Line 55, delete "both, of the which penetrated", and insert -- both which penetrated --, therefor.

Column 5,
Line 13, delete "Epui-Phase-Plot", and insert -- Equi-Phase-Plot --, therefor.
Line 47, delete "s-0.7x10$^7$s", and insert -- s=0.7x10$^7$s --, therefor.

Column 9,
Line 3, delete "108", insert -- 109 --, therefor.

Column 10,
Line 29, delete "physics on, RFEC responses", and insert -- physics on RFEC responses --, therefor.
Line 63, delete "followanmg", and insert -- following --, therefor.

Column 12,
Line 17, delete "$A_5=\pi((r_3)^2-(r_2)^2)$", and insert -- $A_5=\pi((r_3)^2-(r_2)^2)$ --, therefor.
Line 46, delete "[T.m/A]", and insert -- [T•m/A] --, therefor.
Line 47, delete "c=0.03 - 3.0", and insert -- $c \cong 0.03 - 3.0$ --, therefor.
Line 54, delete "eliamninated", and insert -- eliminated --, therefor.

Column 13,
Line 12, delete "auxiliaray", and insert -- auxiliary --, therefor.

Column 14,
Line 15, delete "absolutely", and insert -- absolute --, therefor.

Column 15,
Line 49, delete "shifat", and insert -- shift --, therefor.

Column 17,
Line 56, delete "fatrther", and insert -- further --, therefor.

UNITED STATES PATENT AND TRADEMARK OFFICE
CERTIFICATE OF CORRECTION

PATENT NO. : 6,002,251
DATED : December 14, 1999
INVENTOR(S) : Yu-shi Sun

It is certified that error appears in the above-identified patent and that said Letters Patent is hereby corrected as shown below:

Column 18,
Line 26, delete "haave", and insert -- have --, therefor.
Line 66, delete "plate-atickness", and insert -- plate-thickness --, therefor.

Column 19,
Line 50, delete "ranage", and insert -- range --, therefor.

Column 20,
Line 22, delete "at at least", and insert -- at least --, therefor.
Line 23, delete "passaed", and insert -- passed --, therefor.
Line 28, delete "altermating", and insert -- alternating --, therefor.
Line 42, delete "rernote-field", and insert -- remote-field --, therefor.

Column 21,
Line 2, delete "[T.m/A]", and insert -- [T•m/A] --, therefor.
Lines 2 and 3, delete "c=0.03 to 3.0", and insert -- $c \geq 0.03$ to 3.0 --, therefor.
Line 26, delete "[T.m/A]", and insert -- [T•m/A] --, therefor.
Line 27, delete "c=0.03 to 3.0", and insert -- $c \geq 0.03$ to 3.0 --, therefor.
Line 63, delete "field as", and insert -- field signal --, therefor.

Column 22,
Line 16, delete "[T.m/A]", and insert -- [T•m/A] --, therefor.
Lines 16 and 17, delete "c=0.03 to 3.0", and insert -- $c \geq 0.03$ to 3.0 --, therefor.
Line 32, delete "$\Theta_a = \Theta_{at} + 180° \ \Theta_{pt} + \Theta_p$.", and insert -- $\Theta_a = \Theta_{at} + 180° - \Theta_{pt} + \Theta_p$, wherein a certain driving signal of AC current is applied to the excitation unit, having a magnitude designated as $I_p$ and phase designated as $\Theta_p$ and having a certain test frequency, and a resultant primary test pick-up probe signal is received having voltage magnitude designated $V_{pt}$ and phase designated $\Theta_{pt}$ (in which the phase difference between the driving signal and the pickup probe signal is recorded), then the same certain driving signal is applied to the auxiliary coil and the auxilary test pickup probe signal is received having a voltage magnitude designated as $V_{at}$ and phase designated $\Theta_{at}$ --, therefor.

Column 22,
Lines 34 and 38, delete "claim 2", and insert -- claim 9 --, therefor.
Line 56, delete "claim 16", and insert -- claim 19 --, therefor.

UNITED STATES PATENT AND TRADEMARK OFFICE
CERTIFICATE OF CORRECTION

PATENT NO. : 6,002,251
DATED : December 14, 1999
INVENTOR(S) : Yu-shi Sun

It is certified that error appears in the above-identified patent and that said Letters Patent is hereby corrected as shown below:

Column 23,
Lines 13 and 16, delete "claim 2", and insert -- claim 9 --, therefor.
Lines 57 and 58, delete "th detected voltagae", and insert -- the detected voltage --, therefor.

Column 24,
Line 16, delete "faurther", and insert -- further --, therefor.
Line 51, delete "maganetic", and insert -- magnetic --, therefor.

Column 26,
Line 9, delete "[T.m/A]", and insert -- [T•m/A] --, therefor.
Lines 9 and 10, delete "c=0.03 to 3.0", and insert -- c≈0.03 to 3.0 --, therefor.

Signed and Sealed this

Ninth Day of April, 2002

Attest:

JAMES E. ROGAN
Attesting Officer          *Director of the United States Patent and Trademark Office*